United States Patent
Morgan et al.

(10) Patent No.: US 8,513,257 B2
(45) Date of Patent: Aug. 20, 2013

(54) UREAS AND THEIR USE IN THE TREATMENT OF HEART FAILURE

(75) Inventors: Bradley Paul Morgan, Moraga, CA (US); Alex Muci, San Francisco, CA (US); Pu-Ping Lu, Foster City, CA (US); Erica Anne Kraynack, Belmont, CA (US); Todd Tochimoto, Foster City, CA (US); David J. Morgans, Jr., Los Altos, CA (US)

(73) Assignee: Cytokinetics, Incorporated, South San Francisco, CA (US)

( * ) Notice: Subject to any disclaimer, the term of this patent is extended or adjusted under 35 U.S.C. 154(b) by 0 days.

(21) Appl. No.: 13/341,413

(22) Filed: Dec. 30, 2011

(65) Prior Publication Data

US 2012/0172372 A1    Jul. 5, 2012

Related U.S. Application Data

(63) Continuation of application No. 11/630,062, filed as application No. PCT/US2005/021100 on Jun. 16, 2005, now Pat. No. 8,110,595.

(60) Provisional application No. 60/581,197, filed on Jun. 17, 2004.

(51) Int. Cl.
*A61K 31/497*    (2006.01)
*A61K 31/535*    (2006.01)

(52) U.S. Cl.
USPC ............. 514/253.01; 514/237.2; 514/254.04; 544/131; 544/360; 544/367

(58) Field of Classification Search
USPC ............ 514/253.01, 237.2, 254.04; 544/360, 544/367, 131
See application file for complete search history.

(56) References Cited

U.S. PATENT DOCUMENTS

| | | | |
|---|---|---|---|
| 3,786,058 A | 1/1974 | Edwards | |
| 3,907,782 A | 9/1975 | Edwards | |
| 3,939,169 A | 2/1976 | Edwards | |
| 4,672,066 A | 6/1987 | Carson et al. | |
| 4,787,931 A | 11/1988 | Henrie, II et al. | |
| 5,162,360 A | 11/1992 | Creswell et al. | |
| 5,547,966 A | 8/1996 | Atwal et al. | |
| 5,556,969 A | 9/1996 | Chambers et al. | |
| 5,624,937 A | 4/1997 | Reel et al. | |
| 5,739,144 A | 4/1998 | Warrellow et al. | |
| 5,919,811 A | 7/1999 | Conti et al. | |
| 5,962,455 A | 10/1999 | Blum et al. | |
| 5,962,483 A | 10/1999 | Warrellow et al. | |
| 5,972,975 A | 10/1999 | Esser et al. | |
| 5,994,368 A | 11/1999 | Oku et al. | |
| 6,001,860 A | 12/1999 | Hamanaka | |
| 6,005,008 A | 12/1999 | Widdowson et al. | |
| 6,174,905 B1 | 1/2001 | Suzuki et al. | |
| 6,207,809 B1 | 3/2001 | Nestler | |
| 6,262,083 B1 | 7/2001 | Moon et al. | |
| 6,329,395 B1 | 12/2001 | Dugar et al. | |
| 6,407,124 B1 | 6/2002 | Rawlins et al. | |
| 6,573,264 B1 | 6/2003 | Zablocki et al. | |
| 6,583,282 B1 | 6/2003 | Zhang et al. | |
| 6,635,641 B2 | 10/2003 | Bender et al. | |
| 6,645,990 B2 | 11/2003 | Askew et al. | |
| 6,656,971 B2 | 12/2003 | Wu et al. | |
| 6,670,376 B1 | 12/2003 | Moran et al. | |
| 6,696,576 B2 | 2/2004 | Baumann et al. | |
| 6,916,814 B2 | 7/2005 | Moss et al. | |
| 7,176,222 B2 | 2/2007 | Morgan et al. | |
| 7,371,871 B2 | 5/2008 | Schilling et al. | |
| 7,399,866 B2 | 7/2008 | Morgan et al. | |
| 7,491,826 B2 | 2/2009 | Morgan et al. | |
| 7,507,735 B2 | 3/2009 | Morgan et al. | |
| 7,538,223 B2 | 5/2009 | Morgan et al. | |
| 7,718,657 B2 | 5/2010 | Morgan et al. | |
| 2002/0165394 A1 | 11/2002 | Dumas et al. | |
| 2003/0008868 A1 | 1/2003 | Francesco Cirillo et al. | |
| 2003/0045552 A1 | 3/2003 | Robarge et al. | |
| 2003/0092702 A1 | 5/2003 | Cirillo et al. | |
| 2003/0096841 A1 | 5/2003 | Robarge et al. | |
| 2003/0130309 A1 | 7/2003 | Moss et al. | |
| 2003/0207872 A1 | 11/2003 | Riedl et al. | |
| 2003/0229066 A1 | 12/2003 | Hendrix et al. | |
| 2003/0236287 A1 | 12/2003 | Piotrowski et al. | |
| 2004/0019099 A1 | 1/2004 | Aslanian et al. | |
| 2004/0038962 A1 | 2/2004 | Ashworth et al. | |
| 2004/0097483 A1 | 5/2004 | Zeng et al. | |
| 2004/0102636 A1* | 5/2004 | Miller et al. ................. 546/306 |

(Continued)

FOREIGN PATENT DOCUMENTS

| DE | 3147879 | 6/1983 |
|---|---|---|
| EP | 27965 | 5/1981 |

(Continued)

OTHER PUBLICATIONS

International Search Report and Written Opinion mailed Jan. 14, 2005, for Application No. PCT/US04/01069, filed Jan. 14, 2004.
International Search Report and Written Opinion for International Application No. PCT/US05/21100, mailed Aug. 2, 2006, 10 pages.
Office Action mailed Jun. 22, 2006, for U.S. Appl. No. 11/032,227, filed Jan. 11, 2005.
Notice of Allowance and Notice of Allowability mailed Oct. 18, 2006, for U.S. Appl. No. 11/032,227, filed Jan. 11, 2005.
Office Action mailed May 29, 2007, for U.S. Appl. No. 10/890,829, filed Jul. 14, 2004.
Jeffcoat et al., STN Accession No. 1977:462295; Document No. 87:62295 (1977).
Kempter et al., STN Accession Number: 1984:510849; Document No. 101:110849 (1983).
El-Sharief et al., STN Accession No. 1987:549199; Document No. 107:14919 (1987).
Office Action mailed Sep. 13, 2007, for U.S. Appl. No. 10/890,829, filed Jul. 14, 2004.

(Continued)

*Primary Examiner* — James O Wilson
*Assistant Examiner* — Ebenezer O Sackey
(74) *Attorney, Agent, or Firm* — Finnegan, Henderson, Farabow, Garrett & Dunner LLP

(57) ABSTRACT

Certain substituted urea derivatives selectively modulate the cardiac sarcomere, for example by potentiating cardiac myosin, and are useful in the treatment of systolic heart failure including congestive heart failure.

32 Claims, No Drawings

(56) References Cited

U.S. PATENT DOCUMENTS

| | | |
|---|---|---|
| 2004/0224875 A1 | 11/2004 | Schilling et al. |
| 2004/0229937 A1 | 11/2004 | Dumas et al. |
| 2004/0235829 A1 | 11/2004 | Scott et al. |
| 2005/0032798 A1 | 2/2005 | Boyer et al. |
| 2005/0038031 A1 | 2/2005 | Dumas et al. |
| 2005/0059703 A1 | 3/2005 | Wilhelm et al. |
| 2005/0159416 A1 | 7/2005 | Morgan et al. |
| 2006/0014761 A1 | 1/2006 | Morgan et al. |
| 2006/0025470 A1 | 2/2006 | Morgan et al. |
| 2006/0241110 A1 | 10/2006 | Morgan et al. |
| 2007/0066626 A1 | 3/2007 | Morgan et al. |
| 2007/0161617 A1 | 7/2007 | Morgan et al. |
| 2007/0195704 A1 | 8/2007 | Gonzalez et al. |
| 2007/0197497 A1 | 8/2007 | Morgan et al. |
| 2007/0197504 A1 | 8/2007 | Morgan et al. |
| 2007/0197505 A1 | 8/2007 | Morgan et al. |
| 2007/0197507 A1 | 8/2007 | Morgan et al. |
| 2007/0208000 A1 | 9/2007 | Morgan et al. |
| 2009/0036447 A1 | 2/2009 | Morgan et al. |
| 2009/0099198 A1 | 4/2009 | Morgan et al. |
| 2009/0176307 A1 | 7/2009 | Morgan et al. |
| 2009/0247544 A1 | 10/2009 | Morgan et al. |
| 2009/0324511 A1 | 12/2009 | Morgan et al. |
| 2010/0029680 A1 | 2/2010 | Morgan et al. |

FOREIGN PATENT DOCUMENTS

| | | |
|---|---|---|
| EP | 81142 | 6/1983 |
| EP | 0634402 A1 | 1/1995 |
| EP | 0656350 A | 6/1995 |
| EP | 1104763 A1 | 6/2001 |
| GB | 921682 | 3/1963 |
| JP | 10-168079 | 6/1998 |
| JP | 11-302173 | 11/1999 |
| JP | 2000-256194 | 9/2000 |
| JP | 2002-220338 | 8/2002 |
| NZ | 240935 | 11/1994 |
| WO | WO 84/03884 A1 | 10/1984 |
| WO | WO 92/10468 | 6/1992 |
| WO | WO 93/14074 A1 | 7/1993 |
| WO | WO 96/10559 A1 | 4/1996 |
| WO | WO 96/39382 A1 | 12/1996 |
| WO | WO 98/35941 A1 | 8/1998 |
| WO | WO 98/41510 A1 | 9/1998 |
| WO | WO 98/50346 A2 | 11/1998 |
| WO | WO 98/52558 A1 | 11/1998 |
| WO | WO 98/52559 A1 | 11/1998 |
| WO | WO 99/32106 | 7/1999 |
| WO | WO 99/32111 | 7/1999 |
| WO | WO 99/32363 | 7/1999 |
| WO | WO 99/32436 A1 | 7/1999 |
| WO | WO 99/32463 A1 | 7/1999 |
| WO | WO 99/64394 A1 | 12/1999 |
| WO | WO 00/41698 | 7/2000 |
| WO | WO 01/07411 A1 | 2/2001 |
| WO | WO 01/25190 A1 | 4/2001 |
| WO | WO 01/36403 A1 | 5/2001 |
| WO | WO 01/53274 A1 | 7/2001 |
| WO | WO 01/98269 A2 | 12/2001 |
| WO | WO 02/00626 A1 | 1/2002 |
| WO | WO 02/00632 A1 | 1/2002 |
| WO | WO 02/06231 A1 | 1/2002 |
| WO | WO 02/06246 A1 | 1/2002 |
| WO | WO 02/14311 A2 | 2/2002 |
| WO | WO 02/059106 A1 | 8/2002 |
| WO | WO 02/062763 | 8/2002 |
| WO | WO 02/064576 A1 | 8/2002 |
| WO | WO 02/070462 A1 | 9/2002 |
| WO | WO 02/085857 A2 | 10/2002 |
| WO | WO 02/092576 A1 | 11/2002 |
| WO | WO 02/099388 A2 | 12/2002 |
| WO | WO 03/007942 A1 | 1/2003 |
| WO | WO 03/013523 A1 | 2/2003 |
| WO | WO 03/022820 A1 | 3/2003 |
| WO | WO 03/024933 A1 | 3/2003 |
| WO | WO 03/042164 A1 | 5/2003 |
| WO | WO 03/059258 | 7/2003 |
| WO | WO 03/062224 A1 | 7/2003 |
| WO | WO 03/062235 A1 | 7/2003 |
| WO | WO 03/068228 A1 | 8/2003 |
| WO | WO 03/072098 A1 | 9/2003 |
| WO | WO 03/074501 A1 | 9/2003 |
| WO | WO 03/082278 A1 | 10/2003 |
| WO | WO 03/082808 A1 | 10/2003 |
| WO | WO 03/082861 A2 | 10/2003 |
| WO | WO 03/088967 A1 | 10/2003 |
| WO | WO 03/091229 A1 | 11/2003 |
| WO | WO 03/093250 A2 | 11/2003 |
| WO | WO 03/097576 A2 | 11/2003 |
| WO | WO 03/099771 A2 | 12/2003 |
| WO | WO 2004/000831 A1 | 12/2003 |
| WO | WO 2004/002481 A1 | 1/2004 |
| WO | WO 2004/013102 A1 | 2/2004 |
| WO | WO 2004/013132 A1 | 2/2004 |
| WO | WO 2004/019958 A1 | 3/2004 |
| WO | WO 2004/022561 | 3/2004 |
| WO | WO 2004/024729 A1 | 3/2004 |
| WO | WO 2004/039306 A2 | 5/2004 |
| WO | WO 2004/101529 A1 | 11/2004 |
| WO | WO 2005/051366 A2 | 6/2005 |
| WO | WO 2005/080330 A1 | 9/2005 |
| WO | WO 2005/113494 A2 | 12/2005 |
| WO | WO 2006/009726 A2 | 1/2006 |
| WO | WO 2006/089871 A2 | 8/2006 |
| WO | WO 2007/070626 A2 | 6/2007 |
| WO | WO2007070626 A2 | 6/2007 |
| WO | WO 2007/078839 A2 | 7/2007 |

OTHER PUBLICATIONS

Office Action mailed Sep. 7, 2007, for U.S. Appl. No. 10/541,596, filed Apr. 25, 2006.

Notice of Allowance and Notice of Allowability mailed Jan. 15, 2008, for U.S. Appl. No. 10/890,829, filed Jul. 14, 2004.

Notice of Allowance mailed Dec. 21, 2007, for U.S. Appl. No. 10/541,596, filed Apr. 25, 2006.

Supplementary Partial European Search Report completed Aug. 13, 2007 for European Application No. 04702228.

Office Action mailed Mar. 20, 2008 for U.S. Appl. No. 11/498,986, filed Aug. 4, 2006.

Examiner Search Strategy and Results mailed Mar. 20, 2008 for U.S. Appl. No. 11/498,986, filed Aug. 4, 2006.

Office Action mailed Oct. 12, 2007 for U.S. Appl. No. 11/155,940, filed Jun. 16, 2005.

Jeffcoat et al., Drug Metabolism and Disposition 5(2):157-166.

Mizukura et al., STN Accession No. 113:106314; Original Reference No. 113:17823a,17826a (1990).

Office Action mailed May 22, 2008, for U.S. Appl. No. 10/890,829, filed Jul. 14, 2004.

Notice of Allowance mailed Aug. 11, 2008 for U.S. Appl. No. 11/155,940, filed Jun. 16, 2005.

Aslanian et al., 2002, "Identification of a Novel, Orally Bioavailable Histamine $H_3$ Receptor Antagonist Based on the 4-Benzyl-(1 H-imidazol-4-yl) Template," Bioorganic & Medicinal Chemistry Letters, 12(6): 937-941.

Di Fabio et al., 1999, "Substituted Analogues of GV150526 as Potent Glycine Binding Site Antagonists in Animal Models of Cerebral Ischemia," J. Med. Chem., 42(18): 3486-3493.

Fehr et al., 1974, "Antihypertensiv wirksame Harnstoffderivate des 8-Aminomethyl-6-methyl-ergolens, 78. Mitteilung über Mutterkornalkaloide (1)," Eur. J. Med. Chem.—Chimica Therapeutica, 9(6): 597-601.

Henrie II et al., 1988, "Activity Optimization of Pyridinyl N-Oxidase Urea Cytokinin Mimics," J. Agric. Food Chem., 36(3): 626-633.

Jones et al., 1968, "Amidines and Guanidines Related to Congocidin. Part IV. Thiophen, Pyridine, and Benzene Analogues," J. Chem. Soc. (C), (5): 550-554.

Koščí et al., 1987, "Synthesis and addition-nucleophilic reactions of 2-chloro- and 2,6-dimethyl-4-chloro-3-pyridyl isocyanates," Chem. Papers, 41(5): 683-691.

Kujundžić et al., 1991, "Synthesis of 8-Methyl-1,2,3,4-tetrahydropyrido-[3,4-d]pyrimidine-2,4-diones," Croatica Chemica Acta, 64(4): 599-606.

Mamouni et al., 2003, "A Facile Synthesis of New 3-Substituted-2,3-dihydropyrido[3,2-*d*]pyrimidine-2,4-diones," Synthetic Communications, 33(24): 4259-4268.

Patani et al. Chemical Reviews, 1996 41(8), 3147-76.

Schoene et al., 1976, "Protective Activity of Pyridinium Salts Against Soman Poisoning in Vivo and in Vitro," Biochemical Pharmacology, 25(17): 1955-1958.

Tanaka et al., Journal of Medicinal Chemistry, 1998, 41, 2390-2410.

Trivedi et al., Journal of Medicinal Chemistry, 1994, 37(11),1652-1659.

Vinkers et al., 2003, "Synopsis: SYNthesize and OPtimize System in Silico," J. med. Chem., 46(13): 2765-2773.

Registry Records Not Indexed in Chemical Abstracts (10 records total) (5 pages).

*Ex Parte* Quayle Action mailed Mar. 3, 2009 for U.S. Appl. No. 11/639,390, filed Dec. 13, 2006.

*Ex Parte* Quayle Action mailed Aug. 5, 2009 for U.S. Appl. No. 11/639,390, filed Dec. 13, 2006.

International Search Report and Written Opinion for International Application No. PCT/US06/047668, mailed Jan. 29, 2009.

International Search Report and Written Opinion for International Application No. PCT/US06/047672, mailed Feb. 27, 2008.

International Search Report and Written Opinion for International Application No. PCT/US06/047731, mailed Sep. 22, 2008.

International Search Report and Written Opinion for International Application No. PCT/US2006/047976 mailed Sep. 23, 2008 (10 pages).

International Search Report and Written Opinion for International Application No. PCT/US2006/047827 mailed Sep. 22, 2008 (10 pages).

International Search Report and Written Opinion for International Application No. PCT/US2006/047680 mailed Sep. 24, 2008 (10 pages).

Final Office Action mailed Jan. 6, 2009 for U.S. Appl. No. 11/640,438, filed Dec. 14, 2006.

Office Action mailed Jun. 10, 2010 for U.S. Appl. No. 12/469,603, filed May 20, 2009.

Office Action mailed Mar. 5, 2009 for U.S. Appl. No. 11/639,380, filed Dec. 13, 2006.

Office Action mailed Aug. 6, 2009 for U.S. Appl. No. 11/639,380, filed Dec. 13, 2006.

Office Action mailed May 20, 2008 for U.S. Appl. No. 11/155,940, filed Jun. 16, 2005.

Office Action mailed Jul. 10, 2008 for U.S. Appl. No. 11/640,438, filed Dec. 14, 2006.

Office Action mailed Aug. 28, 2008 for U.S. Appl. No. 11/498,986, filed Aug. 4, 2006.

Office Action mailed Oct. 15, 2008 for U.S. Appl. No. 11/639,400, filed Dec. 13, 2006.

Office Action mailed Sep. 4, 2008, for U.S. Appl. No. 11/639,390, filed Dec. 13, 2006.

Office Action mailed Oct. 15, 2008 for U.S. Appl. No. 11/639,398, filed Dec. 13, 200.

Office Action mailed Apr. 16, 2009 for U.S. Appl. No. 11/639,398, filed Dec. 13, 2006.

Office Action mailed Dec. 28, 2009 for U.S. Appl. No. 11/639,398, filed Dec. 13, 2006.

Office Action mailed Oct. 5, 2010 for U.S. Appl. No. 12/238,313, filed Sep. 25, 2008.

Notice of Abandonment mailed Feb. 19, 2010 for U.S. Appl. No. 11/639,380, filed Dec. 13, 2006.

Notice of Abandonment mailed May 5, 2009 for U.S. Appl. No. 11/639,400, filed Dec. 13, 2006.

Notice of Abandonment mailed Sep. 29, 2009 for U.S. Appl. No. 11/640,438, filed Dec. 14, 2006.

Notice of Abandonment mailed Oct. 22, 2007 for U.S. Appl. No. 11/643,015, filed Dec. 19, 2006.

Notice of Allowance mailed Sep. 29, 2008, for U.S. Appl. No. 10/890,829, filed Jul. 14, 2004.

Notice of Allowance mailed Nov. 28, 2008 for U.S. Appl. No. 11/498,986, filed Aug. 4, 2006.

Notice of Allowance mailed Jan. 27, 2009 for U.S. Appl. No. 11/498,986, filed Aug. 4, 2006.

Notice of Allowance mailed Jan. 8, 2010 for U.S. Appl. No. 11/639,390, filed Dec. 13, 2006.

Supplementary European Search Report, Communication regarding the transmission of the European Search Report, and European Search Opinion mailed Jul. 5, 2010 for EP Application No. 06 83 9401.

Notice of Allowance for U.S. Appl. No. 11/630,062 dated Sep. 30, 2011.

* cited by examiner

UREAS AND THEIR USE IN THE TREATMENT OF HEART FAILURE

This application is a continuation application of U.S. application Ser. No. 11/630,062 now U.S. Pat. No.8,110,595, with a 371(c) date of Sep. 8, 2008, which is the U.S. national stage of International Application No. PCT/US2005/021100 filed Jun. 16, 2005, published as International Publication No. WO 2006/009726, which claims the benefit of U.S. Provisional Patent Application No. 60/581,197, filed Jun. 17, 2004; each of which is incorporated herein by reference for all purposes.

The invention relates to substituted urea derivatives, particularly to chemical entities that selectively modulate the cardiac sarcomere, and specifically to chemical entities, pharmaceutical compositions and methods of treatment for heart disease.

The "sarcomere" is an elegantly organized cellular structure found in cardiac and skeletal muscle made up of interdigitating thin and thick filaments; it comprises nearly 60% of cardiac cell volume. The thick filaments are composed of "myosin," the protein responsible for transducing chemical energy (ATP hydrolysis) into force and directed movement. Myosin and its functionally related cousins are called motor proteins. The thin filaments are composed of a complex of proteins. One of these proteins, "actin" (a filamentous polymer) is the substrate upon which myosin pulls during force generation. Bound to actin are a set of regulatory proteins, the "troponin complex" and "tropomyosin," which make the actin-myosin interaction dependent on changes in intracellular $Ca^{2+}$ levels. With each heartbeat, $Ca^{2+}$ levels rise and fall, initiating cardiac muscle contraction and then cardiac muscle relaxation Each of the components of the sarcomere contributes to its contractile response.

Myosin is the most extensively studied of all the motor proteins. Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II consists of two globular head domains linked together by a long alpha-helical coiled-coiled tail that assembles with other myosin-IIs to form the core of the sarcomere's thick filament. The globular heads have a catalytic domain where the actin binding and ATP functions of myosin take place. Once bound to an actin filament, the release of phosphate (cf. ATP to ADP) leads to a change in structural conformation of the catalytic domain that in turn alters the orientation of the light-chain binding lever arm domain that extends from the globular head; this movement is termed the powerstroke. This change in orientation of the myosin head in relationship to actin causes the thick filament of which it is a part to move with respect to the thin actin filament to which it is bound. Un-binding of the globular head from the actin filament (also $Ca^{2+}$ modulated) coupled with return of the catalytic domain and light chain to their starting conformation/orientation completes the contraction and relaxation cycle.

Mammalian heart muscle consists of two forms of cardiac myosin, alpha and beta, and they are well characterized. The beta form is the predominant form (>90 percent) in adult human cardiac muscle. Both have been observed to be regulated in human heart failure conditions at both transcriptional and translational levels, with the alpha form being down-regulated in heart failure.

The sequences of all of the human skeletal, cardiac, and smooth muscle myosins have been determined. While the cardiac alpha and beta myosins are very similar (93% identity), they are both considerably different from human smooth muscle (42% identity) and more closely related to skeletal myosins (80% identity). Conveniently, cardiac muscle myosins are incredibly conserved across mammalian species. For example, both alpha and beta cardiac myosins are >96% conserved between humans and rats, and the available 250-residue sequence of porcine cardiac beta myosin is 100% conserved with the corresponding human cardiac beta myosin sequence. Such sequence conservation contributes to the predictability of studying myosin based therapeutics in animal based models of heart failure.

The components of the cardiac sarcomere present targets for the treatment of heart failure, for example by increasing contractility or facilitating complete relaxation to modulate systolic and diastolic function, respectively.

Congestive heart failure ("CHF") is not a specific disease, but rather a constellation of signs and symptoms, all of which are caused by an inability of the heart to adequately respond to exertion by increasing cardiac output. The dominant pathophysiology associated with CHF is systolic dysfunction, an impairment of cardiac contractility (with a consequent reduction in the amount of blood ejected with each heartbeat). Systolic dysfunction with compensatory dilation of the ventricular cavities results in the most common form of heart failure, "dilated cardiomyopathy," which is often considered to be one in the same as CHF. The counterpoint to systolic dysfunction is diastolic dysfunction, an impairment of the ability to fill the ventricles with blood, which can also result in heart failure even with preserved left ventricular function. Congestive heart failure is ultimately associated with improper function of the cardiac myocyte itself, involving a decrease in its ability to contract and relax.

Many of the same underlying conditions can give rise to systolic and/or diastolic dysfunction, such as atherosclerosis, hypertension, viral infection, valvular dysfunction, and genetic disorders. Patients with these conditions typically present with the same classical symptoms: shortness of breath, edema and overwhelming fatigue. In approximately half of the patients with dilated cardiomyopathy, the cause of their heart dysfunction is ischemic heart disease due to coronary atherosclerosis. These patients have had either a single myocardial infarction or multiple myocardial infarctions; here, the consequent scarring and remodeling results in the development of a dilated and hypocontractile heart. At times the causative agent cannot be identified, so the disease is referred to as "idiopathic dilated cardiomyopathy." Irrespective of ischemic or other origin, patients with dilated cardiomyopathy share an abysmal prognosis, excessive morbidity and high mortality.

The prevalence of CHF has grown to epidemic proportions as the population ages and as cardiologists have become more successful at reducing mortality from ischemic heart disease, the most common prelude to CHF. Roughly 4.6 million people in the United States have been diagnosed with CHF; the incidence of such diagnosis is approaching 10 per 1000 after 65 years of age. Hospitalization for CHF is usually the result of inadequate outpatient therapy. Hospital discharges for CHF rose from 377,000 (in 1979) to 970,000 (in 2002) making CHF the most common discharge diagnosis in people age 65 and over. The five-year mortality from CHF approaches 50%. Hence, while therapies for heart disease have greatly improved and life expectancies have extended over the last several years, new and better therapies continue to be sought, particularly for CHF.

"Acute" congestive heart failure (also known as acute "decompensated" heart failure) involves a precipitous drop in cardiac function resulting from a variety of causes. For example in a patient who already has congestive heart failure, a new myocardial infarction, discontinuation of medications, and dietary indiscretions may all lead to accumulation of edema fluid and metabolic insufficiency even in the resting state. A therapeutic agent that increases cardiac function during such an acute episode could assist in relieving this metabolic insufficiency and speeding the removal of edema, facilitating the return to the more stable "compensated" congestive heart failure state. Patients with very advanced congestive heart failure particularly those at the end stage of the disease also could benefit from a therapeutic agent that increases cardiac function, for example, for stabilization while waiting for a heart transplant. Other potential benefits could be provided to patients coming off a bypass pump, for example, by administration of an agent that assists the stopped or slowed heart in resuming normal function. Patients who have diastolic dysfunction (insufficient relaxation of the heart muscle) could benefit from a therapeutic agent that modulates relaxation.

Inotropes are drugs that increase the contractile ability of the heart. As a group, all current inotropes have failed to meet the gold standard for heart failure therapy, i.e., to prolong patient survival. In addition, current agents are poorly selective for cardiac tissue, in part leading to recognized adverse effects that limit their use. Despite this fact, intravenous inotropes continue to be widely used in acute heart failure (e.g., to allow for reinstitution of oral medications or to bridge patients to heart transplantation) whereas in chronic heart failure, orally given digoxin is used as an inotrope to relieve patient symptoms, improve the quality of life, and reduce hospital admissions.

Current inotropic therapies improve contractility by increasing the calcium transient via the adenylyl cyclase pathway, or by delaying cAMP degradation through inhibition of phosphodiesterase (PDE), which can be detrimental to patients with heart failure.

Given the limitations of current agents, new approaches are needed to improve cardiac function in congestive heart failure. The most recently approved short-term intravenous agent, milrinone, is more than fifteen years old. The only available oral drug, digoxin, is over 200 hundred years old. There remains a great need for agents that exploit new mechanisms of action and may have better outcomes in terms of relief of symptoms, safety, and patient mortality, both short-term and long-term. New agents with an improved therapeutic index over current agents will provide a means to achieve these clinical outcomes.

The selectivity of agents directed at the cardiac sarcomere (for example, by targeting cardiac beta myosin) has been identified as an important means to achieve this improved therapeutic index. The present invention provides such agents (particularly sarcomere activating agents) and methods for their identification and use.

Another approach may be to directly activate cardiac myosin without changing the calcium transient to improving cardiac contractility. The present invention provides such agents (particularly myosin activating agents) and methods for their identification and use.

Provided is at least one chemical entity chosen from compounds of Formula I

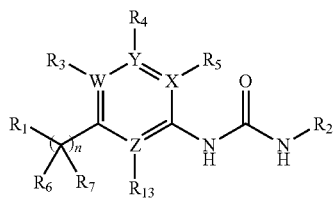

Formula I and pharmaceutically acceptable salts, chelates, non-covalent complexes, prodrugs, and mixtures thereof, wherein
W, X, Y, and Z are independently —C= or —N=, provided that no more than two of W, X, Y, and Z are —N=;
n is one, two, or three;
$R_1$ is optionally substituted amino or optionally substituted heterocycloalkyl;
$R_2$ is optionally substituted aryl, optionally substituted aralkyl; optionally substituted cycloalkyl, optionally substituted heteroaryl, optionally substituted heteroaralkyl or optionally substituted heterocycloalkyl,
$R_3$ is hydrogen, halo, cyano, optionally substituted alkyl, optionally substituted heterocycloalkyl, or optionally substituted heteroaryl when W is —C=, and $R_3$ is absent when W is —N=;
$R_4$ is hydrogen, halo, cyano, optionally substituted alkyl, optionally substituted heterocycloalkyl, or optionally substituted heteroaryl when Y is —C=, and $R_4$ is absent when Y is —N=; and
$R_5$ is hydrogen, halo, cyano, optionally substituted alkyl, optionally substituted heterocycloalkyl, or optionally substituted heteroaryl when X is —O=, and $R_5$ is absent when X is —N=;
$R_{13}$ is hydrogen, halo, cyano, hydroxyl, optionally substituted alkyl, optionally substituted heterocycloalkyl, or optionally substituted heteroaryl when Z is —C=, and $R_{13}$ is absent when Z is —N=; and;
$R_6$ and $R_7$ are independently hydrogen, aminocarbonyl, alkoxycarbonyl, optionally substituted alkyl or optionally substituted alkoxy, or $R_6$ and $R_7$, taken together with the carbon to which they are attached, form an optionally substituted 3- to 7-membered ring which optionally incorporates one or two additional heteroatoms, selected from N, O, and S in the ring.

Also provided is a pharmaceutical composition comprising a pharmaceutically acceptable excipient, carrier or adjuvant and at least one chemical entity described herein.

Also provided is a packaged pharmaceutical composition, comprising a pharmaceutical composition comprising a pharmaceutically acceptable excipient, carrier or adjuvant and at least one chemical entity described herein, and instructions for using the composition to treat a patient suffering from a heart disease.

Also provided is a method of treating heart disease in a mammal which method comprises administering to a mammal in need thereof a therapeutically effective amount of at least one chemical entity described herein or a pharmaceutical composition comprising a pharmaceutically acceptable excipient, carrier or adjuvant and at least one chemical entity described herein.

Also provided is a method for modulating the cardiac sarcomere in a mammal which method comprises administering to a mammal in need thereof a therapeutically effective amount of at least one chemical entity described herein or a pharmaceutical composition comprising a pharmaceutically acceptable excipient, carrier or adjuvant and at least one chemical entity described herein.

Also provided is a method for potentiating cardiac myosin in a mammal which method comprises administering to a mammal in need thereof a therapeutically effective amount of at least one chemical entity described herein or a pharmaceutical composition comprising a pharmaceutically acceptable excipient, carrier or adjuvant and at least one chemical entity described herein.

Also provided is the use, in the manufacture of a medicament for treating heart disease, of at least one chemical entity described herein.

Also provided is a method for method of preparing a compound of Formula I.

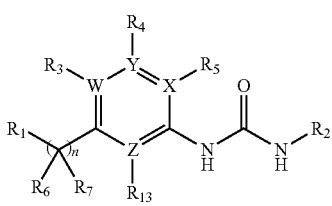

Formula I wherein $R^1$, $R^2$, $R^3$, $R^4$, $R^5$, and $R^{13}$ are as defined above, comprising the steps of
converting a compound of Formula 400

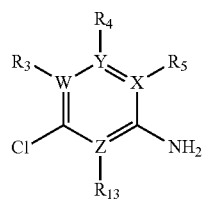

400 to a compound of Formula 401;

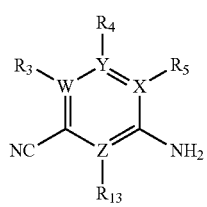

401 hydrolyzing the compound of Formula 401 to a compound of Formula 402

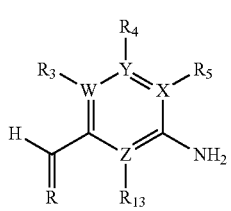

402 wherein R is chosen from O and NH;
contacting a compound of Formula 402 with a compound of formula $R_1$—H wherein $R_1$ is optionally substituted amino or optionally substituted heterocycloalkyl to form a compound of Formula 403; and

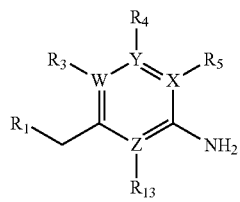

403 contacting a compound of Formula 403 with a compound of the formula $R_2$—NCO to yield a compound of Formula I.

Other aspects and embodiments will be apparent to those skilled in the art form the following detailed description.

As used in the present specification, the following words and phrases are generally intended to have the meanings as set forth below, except to the extent that the context in which they are used indicates otherwise. The following abbreviations and terms have the indicated meanings throughout:

| | |
|---|---|
| Ac = | acetyl |
| Boc = | t-butyloxy carbonyl |
| c- = | cyclo |
| CBZ = | carbobenzoxy = benzyloxycarbonyl |
| DCM = | dichloromethane = methylene chloride = $CH_2Cl_2$ |
| DIBAL-H = | Diisobutylaluminium hydride |
| DIEA or DIPEA = | N,N-diisopropylethylamine |
| DMF = | N,N-dimethylformamide |
| DMSO = | dimethyl sulfoxide |
| eq = | equivalent |
| Et = | ethyl |
| EtOAc = | ethyl acetate |
| EtOH = | ethanol |
| g = | gram |
| GC = | gas chromatography |
| h, hr, hrs = | hour or hours |
| Me = | methyl |
| min = | minute |
| ml = | milliliter |
| mmol = | millimole |
| Ph = | phenyl |
| PyBroP = | bromo-tris-pyrrolidinophosphonium hexafluorophosphate |
| RT = | room temperature |
| s- = | secondary |
| t- = | tertiary |
| TFA = | trifluoroacetic acid |
| THF = | tetrahydrofuran |
| TLC = | thin layer chromatography |
| Volume = | mL/g of material based on the limiting reagent unless specified otherwise |

As used in the present specification, the following words and phrases are generally intended to have the meanings as set forth below, except to the extent that the context in which they are used indicates otherwise.

As used herein, when any variable occurs more than one time in a chemical formula, its definition on each occurrence is independent of its definition at every other occurrence.

A dash ("—") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms. Alkyl groups generally are those of $C_{20}$ or below, such as $C_{13}$ or below, for example, $C_6$ or below. For example $C_1$-$C_6$alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to four carbons.

"Cycloalkyl" indicates a saturated hydrocarbon ring or fused bicyclic ring, having the specified number of carbon atoms, usually from 3 to 12 ring carbon atoms, more usually 3 to 10, or 3 to 7. Examples of cycloalkyl groups include cyclopropyl, cyclobutyl, cyclopentyl, and cyclohexyl as well as bridged and caged saturated ring groups such as norbornane. Examples of fused bicyclic rings include octahydro-1H-indene, octahydropentalene, 1,2,3,3a,4,5-hexahydropentalene, 1,2,4,5,6,7,7a-heptahydro-2H-indene, 4,5,6,7-tetrahydro-2H-indene and the like.

By "alkoxy" is meant an alkyl group attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. The alkyl group of an alkoxy group generally is of $C_{20}$ or below, such as $C_{13}$ or below, for example, $C_6$ or below. "Lower alkoxy" refers to alkoxy groups having one to four carbons.

By "cycloalkoxy" is meant a cycloalkyl group attached through an oxygen bridge such as, for example, cyclopropoxy, cyclobutoxy, cyclopentoxy, cyclohexoxy, cycloheptoxy, and the like. The cycloalkyl group of a cycloalkoxy group generally is of $C_{20}$ or below, such as $C_{13}$ or below, for example, $C_6$ or below.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —$NH_2$.

The term "aminocarbonyl" refers to the group —$CONR^b R^c$, where $R^b$ is chosen from hydrogen, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH (phenyl), —$NHSO_2$ ($C_1$-$C_4$ alkyl), —$NHSO_2$ (phenyl), and —$NHSO_2$($C_1$-$C_4$ haloalkyl).

"Aryl" encompasses: 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

In the term "arylalkyl" or "aralkyl", aryl and alkyl are as defined herein, and the point of attachment is on the alkyl group. This term encompasses, but is not limited to, benzyl, phenethyl, phenylvinyl, phenylallyl and the like.

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the hetero aromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Also included within the definition of heteroaryl are oxide derivatives, for example N-oxides of nitrogen containing aryl groups, such as pyridine-1-oxide, or >S(O) and >S(O)$_2$ derivatives of sulfur containing groups. Examples of heteroaryl groups include, but are not limited to, systems (as numbered from the linkage position assigned priority 1), such as 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In the term "heteroarylalkyl" or "heteroaralkyl", heteroaryl and alkyl are as defined herein, and the point of attachment is on the alkyl group. This term encompasses, but is not limited to, pyridylmethyl, thiophenylmethyl, and (pyrrolyl)1-ethyl.

By "heterocycloalkyl" is meant a cycloalkyl residue in which one to four of the carbon atoms are replaced by a heteroatom such as oxygen, nitrogen or sulfur. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperidyl, and 2,5-piperzinyl. Morpholinyl groups are also contemplated, including 2-morpholinyl and 3-morpholinyl (numbered wherein the oxygen is assigned priority 1).

As used herein, "modulation" refers to a change in myosin or sarcomere activity as a direct or indirect response to the presence of at least one chemical entity described herein, relative to the activity of the myosin or sarcomere in the absence of the compound. The change may be an increase in activity or a decrease in activity, and may be due to the direct interaction of the compound with myosin or the sarcomere, or due to the interaction of the compound with one or more other factors that in turn affect myosin or sarcomere activity.

The term "sulfanyl" includes the groups: —S-(optionally substituted alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

The term "sulfinyl" includes the groups: —S(O)—H, —S(O)-(optionally substituted alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S(O$_2$)—H, —S(O$_2$)-(optionally substituted alkyl), —S(O$_2$)-optionally substituted aryl), —S(O$_2$)-(optionally substituted heteroaryl), —S(O$_2$)-(optionally substituted heterocycloalkyl), —S(O$_2$)-(optionally substituted alkoxy), —S(O$_2$)-optionally substituted aryloxy), —S(O$_2$)-optionally substituted heteroaryloxy), —S(O$_2$)-(optionally substituted heterocycloalkyloxy); and —S(O$_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (up to 5, such as up to 3) hydrogen atoms are replaced by a substituent independently chosen from:

—$R^a$, —$OR^b$, —$O(C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCO^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from hydrogen, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substitutent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$ (phenyl), —SO$_2$(C$_1$-C$_4$ haloalkyl), —SO$_2$NH$_2$, —SO$_2$NH(C$_1$-C$_4$ alkyl), —SO$_2$NH (phenyl), —NHSO$_2$ (C$_1$-C$_4$ alkyl), —NHSO$_2$ (phenyl), and —NHSO$_2$(C$_1$-C$_4$ haloalkyl).

The terms "substituted" cycloalkyl, aryl, heterocycloalkyl, and heteroaryl also include oxo (=O) and oxide (—O$^-$) substituents, for example N-oxides of nitrogen containing aryl groups, such as pyridine-1-oxide, or >S(O) and >S(O)$_2$ derivatives of sulfur containing groups.

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (up to 5, such as up to 3) hydrogen atoms are replaced by a substituent independently chosen from:

—R$^a$, —OR$^b$, —O(C$_1$-C$_2$ alkyl)O— (e.g., methylene-dioxy-), —SR$^b$, guanidine, guanidine wherein one or more of the guanidine hydrogens are replaced with a lower-alkyl group, —NR$^b$R$^c$, halo, cyano, nitro, —COR$^b$, —CO$_2$R$^b$, —CONR$^b$R$^c$, —OCO$^b$, —OCO$_2$R$^a$, —OCONR$^b$R$^c$, —NR$^c$COR$^b$, —NR$^c$CO$_2$R$^a$, —NR$^c$CONR$^b$R$^c$, —CO$_2$R$^b$, —CONR$^b$R$^c$, —NR$^c$COR$^b$, —SOR$^a$, —SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted aryl, and optionally substituted heteroaryl;

R$^b$ is chosen from H, optionally substituted C$_1$-C$_6$ alkyl, optionally substituted aryl, and optionally substituted heteroaryl; and R$^c$ is chosen from hydrogen and optionally substituted C$_1$-C$_4$ alkyl; or R$^b$ and R$^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for cycloallyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$ (C$_1$-C$_4$ haloalkyl), —SO$_2$NH$_2$, —SO$_2$NH(C$_1$-C$_4$ alkyl), —SO$_2$NH (phenyl), —NHSO$_2$(C$_1$-C$_4$ alkyl), —NHSO$_2$(phenyl), and —NHSO$_2$(C$_1$-C$_4$ haloalkyl). One or more carbons in the substituted acyl residue may be replaced by nitrogen, oxygen or sulfur as long as the point of attachment to the parent remains at the carbonyl.

The term "substituted alkoxy" refers to alkoxy wherein the alkyl constituent is substituted (i.e., —O-(substituted alkyl)) wherein "substituted alkyl" refers to alkyl wherein one or more (up to 5, such as up to 3) hydrogen atoms are replaced by a substituent independently chosen from:

—R$^a$, —OR$^b$, —O(C$_1$-C$_2$ alkyl)O— (e.g., methylene-dioxy-), —SR$^b$, guanidine, guanidine wherein one or more of the guanidine hydrogens are replaced with a lower-alkyl group, —NR$^b$R$^c$, halo, cyano, nitro, —COR$^b$, —CO$_2$R$^b$, —CONR$^b$R$^c$, —OCO$^b$, —OCO$_2$R$^a$, —OCONR$^b$R$^c$, —NR$^c$COR$^b$, —NR$^c$CO$_2$R$^a$, —NR$^c$CONR$^b$R$^c$, —SOR$^a$, —SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted aryl, and optionally substituted heteroaryl;

R$^b$ is chosen from H, optionally substituted C$_1$-C$_6$ alkyl, optionally substituted aryl, and optionally substituted heteroaryl; and R$^c$ is chosen from hydrogen and optionally substituted C$_1$-C$_4$ alkyl; where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$—NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for cycloalkyl, heterocycloalkyl, or heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$ (phenyl), —SO$_2$(C$_1$-C$_4$ haloalkyl), —SO$_2$NH$_2$, —SO$_2$NH (C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$haloalkyl). In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

The term "substituted alkoxycarbonyl" refers to the group (substituted alkyl)-O—C(O)— wherein the group is attached to the parent structure through the carbonyl functionality and wherein substituted refers to alkyl wherein one or more (up to 5, such as up to 3) hydrogen atoms are replaced by a substituent independently chosen from:

—R$^a$, —OR$^b$, —O(C$_1$-C$_2$ alkyl)O— (e.g., methylene-dioxy-), —SR", guanidine, guanidine wherein one or more of the guanidine hydrogens are replaced with a lower-alkyl group, —NR$^b$R$^a$, halo, cyano, nitro, —COR$^b$, —CO$_2$R$^b$, —CONR$^b$R$^a$, —OCO$^b$, —OCO$_2$R$^a$, —OCONR$^b$R$^c$, —NR$^a$COR$^b$, —NR$^a$CO$_2$R$^a$, —NR$^a$CONR$^b$R$^a$, —CO$_2$R$^b$, —CONR$^b$R$^a$, —NR$^a$COR$^b$, —SOR$^a$, —SO$_2$R$^a$, —SO$_2$NR$^b$R$^a$, and —NR$^a$SO$_2$R$^a$, where R$^a$ is chosen from optionally substituted C$_1$-C$_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$—N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$—CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$ (phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" refers to the group —NHR$^d$ or —NR$^d$R$^d$ where each R$^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (up to 5, such as up to 3) hydrogen atoms are replaced by a substituent independently chosen from:

—R$^a$, —OR$^b$, —O($C_1$-$C_2$ alkyl)O— (e.g., methylenedioxy-), —SR$^b$, guanidine, guanidine wherein one or more of the guanidine hydrogens are replaced with a lower-alkyl group, —NR$^b$R$^c$, halo, cyano, nitro, —COR$^b$, —CO$_2$R$^b$, —CONR$^b$R$^c$, —OCO$^b$, —OCO$_2$R$^a$, —OCONR$^b$R$^c$, —NR$^c$COR$^b$, —NR$^c$CO$_2$R$^a$, —NR$^c$CONR$^b$R$^c$, —CO$_2$R$^b$, —CONR$^b$R$^c$, —NR$^c$COR$^b$, —SOR$^a$, —SO$_2$R$^c$, —SO$_2$NR$^b$R$^c$, and —NR$^c$SO$_2$R$^a$, where R$^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl; or $R^b$ and $R^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for cycloalkyl, heterocycloallyl, or heteroaryl), —CO$_2$H, —C(O)O$C_1$-$C_4$ alkyl, —CON($C_1$-$C_4$ alkyl)($C_1$-$C_4$—CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH (phenyl), —NHSO$_2$($C_1$-$C_4$ alkyl), —NHSO$_2$(phenyl), and —NHSO$_2$($C_1$-$C_4$ haloalkyl), and wherein optionally substituted acyl, alkoxycarbonyl, sulfonyl and sulfonyl are as defined herein.

Compounds of Formula I include, but are not limited to, optical isomers of compounds of Formula I, racemates, and other mixtures thereof. In addition, compounds of Formula I include Z- and E-forms (or cis- and trans-forms) of compounds with carbon-carbon double bonds. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. Where compounds of Formula I exists in various tautomeric forms, chemical entities of the present invention include all tautomeric forms of the compound.

Compounds of Formula I also include crystalline and amorphous forms of the compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Chemical entities of the present invention include, but are not limited to compounds of Formula I and all pharmaceutically acceptable forms thereof. Pharmaceutically acceptable forms of the compounds recited herein include pharmaceutically acceptable salts, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, chelates, non-covalent complexes, prodrugs, and mixtures.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—($CH_2$)$_n$—COOH where n is 0-4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I.

The term "solvate" refers to the chemical entity formed by the interaction of a solvent and a compound. Suitable solvates are pharmaceutically acceptable solvates, such as hydrates, including, for example, hemi-hydrates, monohydrates, dihydrates, trihydrates, etc.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility.

The term "therapeutically effective amount" of a chemical entity of this invention means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

By "significant" is meant any detectable change that is statistically significant in a standard parametric test of statistical significance such as Student's T-test, where p<0.05.

"Patient" refers to an animal, such as a mammal, for example a human, that has been or will be the object of treatment, observation or experiment. The methods of the invention can be useful in both human therapy and veterinary applications. In some embodiments, the patient is a mammal, and in some embodiments the patient is human.

"Treatment" or "treating" means any treatment of a disease in a patient, including:
  a) preventing the disease, that is, causing the clinical symptoms of the disease not to develop;
  b) inhibiting the disease;
  c) slowing or arresting the development of clinical symptoms; and/or
  d) relieving the disease, that is, causing the regression of clinical symptoms.

The compounds of Formula I can be named and numbered (e.g., using NamExpert™ available from Cheminnovation or the automatic naming feature of ChemDraw Ultra version 9.0 from Cambridge Soft Corporation) as described below. For example, the compound:

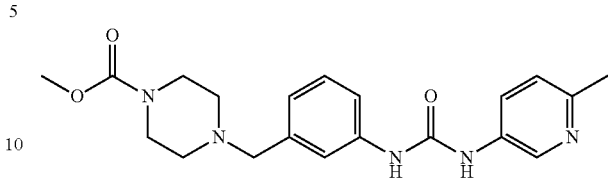

i.e., the compound according to Formula I where W, X, Y and Z are —C=, n is one, $R_1$ is substituted piperazinyl, $R_2$ is 6-methyl-pyridin-3-yl, $R_3$ is hydrogen, $R_4$ is hydrogen, $R_5$ is hydrogen, $R_6$ is hydrogen, $R_7$ is hydrogen and $R_{13}$ is hydrogen can be named methyl 4-[(3-{[(6-methyl-3-pyridyl)amino]carbonylamino}phenyl)methyl]piperazinecarboxylate. Likewise, the compound:

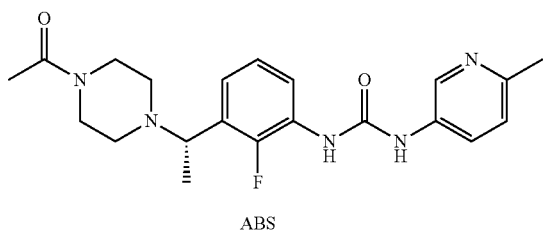

i.e., the compound according to Formula I where W, X, Y and Z are —C=, n is one, $R_1$ is substituted piperazinyl, $R_2$ is 6-methyl-pyridin-3-yl, $R_3$ is hydrogen, $R_4$ is hydrogen, $R_5$ is hydrogen, $R_6$ is hydrogen, $R_7$ is hydrogen and $R_{13}$ is fluoro can be named N-{3-[(1S)-1-(4-acetylpiperazinyl)ethyl]-2-fluorophenyl}[(6-methyl(3-pyridyl))amino]carboxamide.

Likewise, the compound

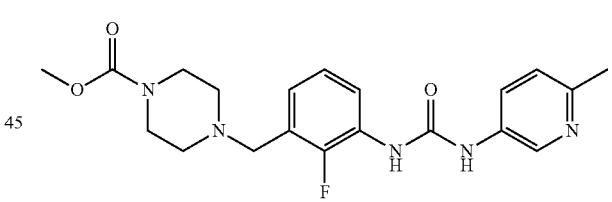

i.e., the compound according to Formula I where W, X, Y and Z are —C=, n is one, $R_1$ is substituted piperazinyl, $R_2$ is 6-methyl-pyridin-3-yl, $R_3$ is hydrogen, $R_4$ is hydrogen, $R_5$ is hydrogen, $R_6$ is hydrogen, $R_7$ is hydrogen and $R_{13}$ is fluoro can be named [3-fluoro-5-(3-pyridin-3-yl-ureido)-benzyl]-methyl-carbamic acid methyl ester or methyl 4-[(2-fluoro-3-{[(6-methyl(3-pyridyl))amino]carbonylamino}phenyl)methyl]piperazinecarboxylate.

The chemical entities described herein can be synthesized utilizing techniques well known in the art, e.g., as illustrated below with reference to the Reaction Schemes.

Unless specified to the contrary, the reactions described herein take place at atmospheric pressure, generally within a temperature range from −10° C. to 110° C. Further, except as employed in the Examples or as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

The terms "solvent", "organic solvent" or "inert solvent" each mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Many of the optionally substituted starting compounds 101, 103, 201, 301 and other reactants are commercially available, e.g., from Aldrich Chemical Company (Milwaukee, Wis.) or can be readily prepared by those skilled in the art using commonly employed synthetic methodology.

REACTION SCHEME 1

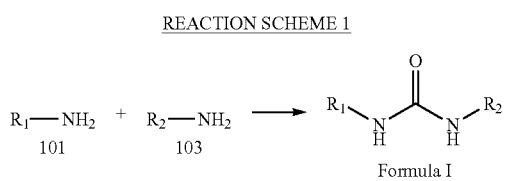

Formula I

Preparation of Compounds of Formula I Referring to Reaction Scheme 1, a flask equipped with a magnetic stirrer, reflux condenser and thermal well, under nitrogen, is charged with phosgene or a phosgene equivalent (typically triphosgene) and a nonpolar, aprotic solvent such as dichloromethane or tetrahydrofuran. A solution of a compound of Formula 101 in a nonpolar, aprotic solvent such as dichloromethane or tetrahydrofuran is added dropwise over about 10-60 minutes and the solution is allowed to stir between 1 to 15 hr. A compound of Formula 103 is added portionwise, and the solution is stirred for about 10-60 min. A base, such as DIEA, is added dropwise for about one hour, and the solution is allowed to stir for about 1-15 hr. The product, a compound of Formula 105, is isolated and purified.

REACTION SCHEME 2

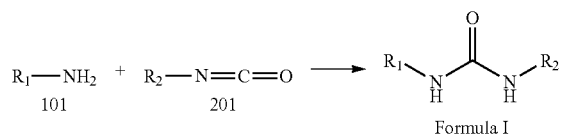

Preparation of Compounds of Formula I Reaction Scheme 2 illustrates an alternative synthesis of compounds of Formula I. The isocyanate of Formula 201 can be formed and isolated independently from either corresponding amine (i.e., $R_2$—$NH_2$) using phosgene or a phosgene equivalent or from the corresponding carboxylic acid (i.e., $R_2$—COOH) using a Curtius or Hoffman rearrangement. A mixture of compounds of Formula 101 and 201 in an aprotic solvent such as dichloromethane or tetrahydrofuran from −40° C. to 110° C. is allowed to stir for between 1 to 15 hr. The product, a compound of Formula I, is isolated and purified.

REACTION SCHEME 3

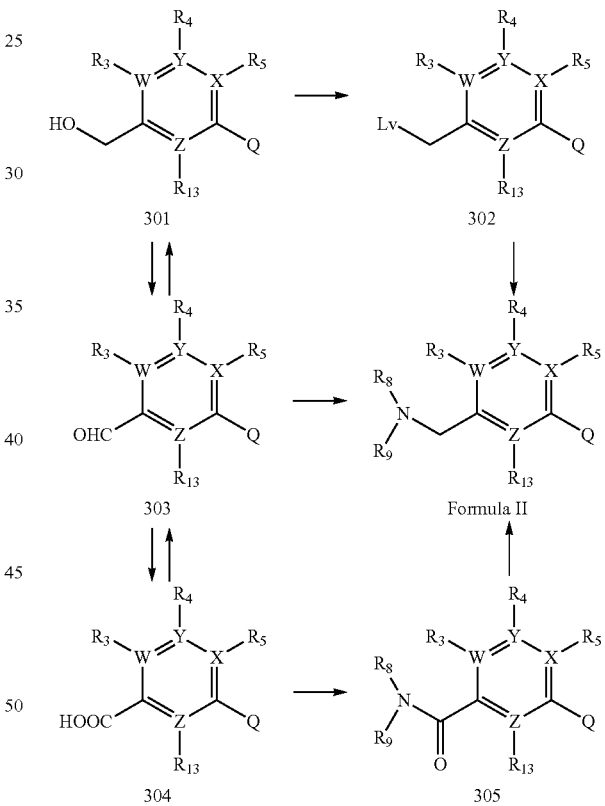

Preparation of Compounds of Formula II Referring to Reaction Scheme 3, the benzylic alcohol of Formula 301 is converted to a leaving group ("Lv" such as halo, mesylate or triflate), 302 using commonly employed synthetic methodology (for example. see: "Comprehensive Organic Transformation" LaRock, Richard C., 1989, VCH publishers, Inc. p. 353-365, which is incorporated herein by reference).

A mixture of a compound of Formula 302 and amine of formula $HNR_8R_9$ in an aprotic solvent such as dichloromethane or DMF from −40° C. to 110° C. is allowed to stir for between 1 to 15 hr. The product, a compound of Formula II, is isolated and purified.

Alternatively, the benzylic alcohol of Formula 301 is oxidized to the aldehyde of Formula 303 using commonly employed synthetic methodology (for example see: "Comprehensive Organic Transformation" LaRock, Richard C., 1989, VCH publishers, Inc. p. 604-615, which is incorporated herein by reference.).

A mixture of a compound of Formula 303 and amine of formula $HNR_8R_9$ in a solvent such as dichloromethane with a reducing agent such as triacetoxyborohidride with or without an acid such as acetic acid from −40° C. to 110° C. is allowed to stir for between 1 to 36 hr. The product, a compound of Formula II, is isolated and purified.

Alternatively, the carboxylic acid of Formula 304 is coupled to an amine to using commonly employed synthetic methodology (for example see: "Comprehensive Organic Transformation" LaRock, Richard C., 1989, VCH publishers, Inc. p. 972-976, which is incorporated herein by reference) to form amide 305. Amide 305 is reduced to a compound of Formula II using commonly employed synthetic methodology such as treating 305 with borane-dimethylsulfide in THF from −40° C. to reflux for 1 to 96 hr.

A compound of Formula II wherein Q is bromo, chloro, nitro, amino, or a protected amino can be conferred to a compound of Formula 101 using commonly employed synthetic methodology. For example, when Q is nitro, it may be reduced to the corresponding amine using hydrogen with a Pd/C catalyst.

Reaction Scheme 4

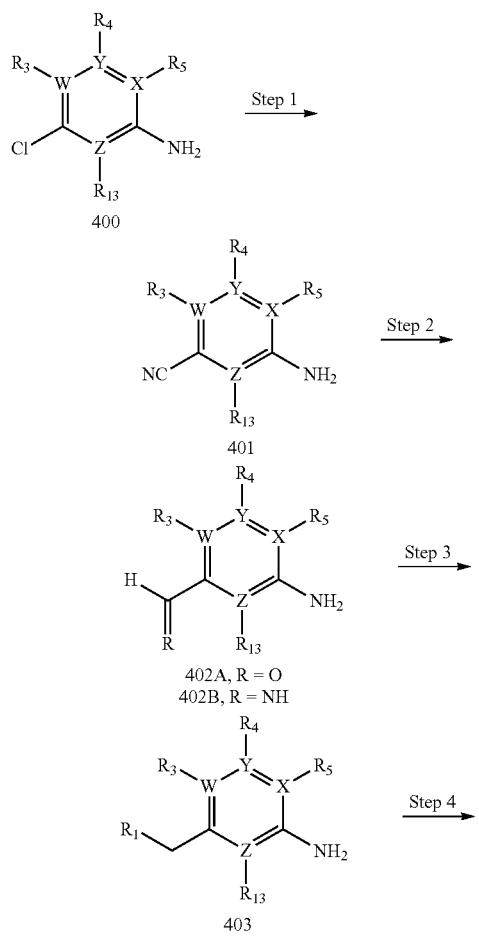

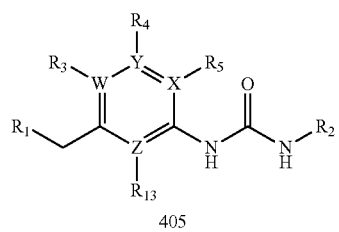

405

Referring to Reaction Scheme 4, Step 1, to a solution of a compound of Formula 400 in NMP is added an excess (such as about at least 2 equivalents) of sodium cyanide and an excess (such as at least 1 equivalent, for example, 1.35 equivalents) of nickel(II) bromide. Additional NMP is added, and the solution is gently warmed to about 200° C. and stirred for about 4 days. The product, a compound of Formula 401, is isolated and optionally purified.

To a ~0° C. solution of a compound of Formula 401 in an inert solvent such as dichloromethane is added an excess (such as two or more equivalents) of a reducing agent, such as DIBAL-H (such as a 1 M solution of DIBAL-H) dropwise over ~3.5 hours, maintaining an internal reaction temperature $\leqq 0°$ C. The product, a mixture of compounds of Formula 402A and 402B, is isolated and optionally purified.

Referring to Reaction Scheme 4, Step 3, to a solution of a mixture of compounds of Formula 402A and 402B in an inert solvent such as THF is added an excess (such as about 1.05 equivalents) of a compound of formula $R_1$—H wherein $R_1$ is optionally substituted amino or optionally substituted heterocycloalkyl and an excess (such as about 1.5 equivalents) of a reducing agent such as triacetoxyborohydride portionwise over ~40 min, maintaining an internal reaction temperature below about 45° C. The product, a compound of Formula 403, is isolated and optionally purified.

Referring to Reaction Scheme 4, Step 4, to a solution of a compound of Formula 403 in a solvent such as acetone is added about an equivalent of a compound of formula $R_2$—NCO dropwise. The reaction is stirred for about one hour and optionally, is warmed to reflux. The product, a compound of Formula 405, is isolated and optionally purified.

A racemic mixture is optionally placed on a chromatography column and separated into (R)- and (S)-enantiomers.

A compound of Formula I is optionally contacted with a pharmaceutically acceptable acid to form the corresponding acid addition salt.

A pharmaceutically acceptable acid addition salt of Formula I is optionally contacted with a base to form the corresponding free base of Formula I.

Certain embodiments of the invention include or employ the compounds of Formula I having the following combinations and permutations of substituent groups. These are presented to support other combinations and permutations of substituent groups, which for the sake of brevity have not been specifically described herein, but should be appreciated as encompassed within the teachings of the present disclosure.

In certain embodiments, the invention relates to at least one chemical entity chosen from compounds of Formula I

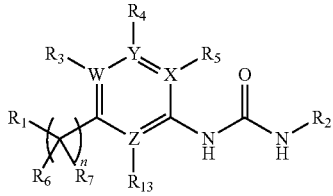

Formula I and pharmaceutically acceptable salts, chelates, non-covalent complexes, prodrugs, and mixtures thereof, wherein
W, X, Y, and Z are independently —C═ or —N═, provided that no more than two of W, X, Y, and Z are —N═;
n is one, two, or three;
$R_1$ is optionally substituted amino or optionally substituted heterocycloalkyl;
$R_2$ is optionally substituted aryl, optionally substituted aralkyl; optionally substituted cycloalkyl, optionally substituted heteroaryl, optionally substituted heteroaralkyl or optionally substituted heterocycloalkyl,
$R_3$ is hydrogen, halo, cyano, optionally substituted alkyl, optionally substituted heterocycloalkyl, or optionally substituted heteroaryl when W is —C═, and $R_3$ is absent when W is —N═;
$R_4$ is hydrogen, halo, cyano, optionally substituted alkyl, optionally substituted heterocycloalkyl, or optionally substituted heteroaryl when Y is —C═, and $R_4$ is absent when Y is —N═; and
$R_5$ is hydrogen, halo, cyano, optionally substituted alkyl, optionally substituted heterocycloalkyl, or optionally substituted heteroaryl when X is —C═, and $R_5$ is absent when X is —N═;
$R_{13}$ is hydrogen, halo, cyano, hydroxyl, optionally substituted alkyl, optionally substituted heterocycloalkyl, or optionally substituted heteroaryl when Z is —C═, and $R_{13}$ is absent when Z is —N═; and;
$R_6$ and $R_7$ are independently hydrogen, aminocarbonyl, alkoxycarbonyl, optionally substituted alkyl or optionally substituted alkoxy, or $R_6$ and $R_7$, taken together with the carbon to which they are attached, form an optionally substituted 3- to 7-membered ring which optionally incorporates one or two additional heteroatoms, selected from N, O, and S in the ring.

In certain embodiments one of W, X, Y and Z is —N═.
In certain embodiments, W, X, Y and Z are —C═.
In certain embodiments, $R_1$ is —$NR_8R_9$ wherein $R_8$ is lower alkyl and $R_9$ is optionally substituted alkyl, optionally substituted heterocycloalkyl, optionally substituted acyl or optionally substituted sulfonyl.

In certain embodiments, $R_8$ is methyl or ethyl.
In certain embodiments, $R_9$ is —(CO)$OR_{10}$ wherein $R_{10}$ is hydrogen or lower alkyl (such as methyl or ethyl). In certain embodiments, $R_{10}$ is hydrogen, methyl or ethyl.
In certain embodiments, $R_9$ is —(SO$_2$)—$R_{17}$ wherein $R_{17}$ is lower alkyl or —$NR_{11}R_{12}$ wherein $R_{11}$ and $R_{12}$ are independently hydrogen or lower alkyl (such as methyl or ethyl).
In certain embodiments, $R_9$ is alkyl optionally substituted with optionally substituted amino.
In certain embodiments, $R_9$ is optionally substituted heterocycloalkyl.
In certain embodiments, $R_1$ is selected from optionally substituted piperazinyl; optionally substituted 1,1-dioxo-1$\lambda^6$-[1,2,5]thiadiazolidin-2-yl; optionally substituted 3-oxo-tetrahydro-pyrrolo[1,2-c]oxazol-6-yl, optionally substituted 2-oxo-imidazolidin-1-yl; optionally substituted morpholinyl; optionally substituted 1,1-dioxo-1$\lambda^6$-thiomorpholin-4-yl; optionally substituted pyrrolidin-1-yl; optionally substituted piperidine-1-yl, optionally substituted azepanyl, optionally substituted 1,4-diazepanyl, optionally substituted 3-oxo-tetrahydro-1H-oxazolo[3,4-a]pyrazin-3(5H)-one, optionally substituted 5,6,7,8-tetrahydro-[1,2,4]triazolo[4,3-a]pyrazinyl, and

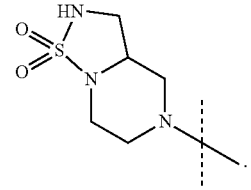

optionally substituted

In certain embodiments, $R_1$ is substituted piperazinyl; optionally substituted piperidine-1-yl, optionally substituted pyrrolidin-1-yl, optionally substituted azepanyl or optionally substituted 1,4-diazepanyl In certain embodiments, $R_1$ is optionally substituted piperazinyl. In certain embodiments, $R_1$ is optionally substituted piperidinyl.

In certain embodiments, $R_2$ is optionally substituted aryl or optionally substituted heteroaryl. In certain embodiments, $R_2$ is optionally substituted phenyl, optionally substituted naphthyl, optionally substituted pyrrolyl, optionally substituted thiazolyl, optionally substituted isooxazolyl, optionally substituted pyrazolyl, optionally substituted oxazolyl, optionally substituted 1,3,4-oxadiazolyl, optionally substituted pyridinyl, optionally substituted pyrazinyl, optionally substituted pyrimidinyl and optionally substituted pyridazinyl.

In certain embodiments, $R_2$ is chosen from pyridin-3-yl, pyridin-4-yl, pyridin-1-oxide, phenyl, pyrimidin-5-yl, and isoxazol-3-yl, wherein each pyridin-3-yl, pyridin-4-yl, pyridin-1-oxide, phenyl, pyrimidin-5-yl, and isoxazol-3-yl is optionally substituted with lower alkyl, lower alkoxy, halo (such as fluoro or chloro), cyano or acetyl. In certain embodiments, $R_2$ is pyridin-3-yl, which is optionally substituted with lower alkyl; $R_2$ is pyridin-4-yl which is optionally substituted with lower allyl; phenyl which is optionally substituted with halo; optionally substituted pyrimidin-5-yl; or optionally substituted isoxazol-3-yl. In certain embodiments, $R_2$ is pyridin-3-yl; 6-methyl-pyridin-3-yl; 6-cyano-pyridin-3-yl; 6-acetyl-pyridin-3-yl; 6-trifluoromethyl-pyridin-3-yl; pyridin-4-yl; 2-methyl-pyridin-4-yl; phenyl; 4-fluorophenyl; 4-chlorophenyl; or 5-methyl-isoxazol-3-yl In certain embodiments, n is one. In certain embodiments, n is two. In certain embodiments, n is three In certain embodiments, $R_6$ and $R_7$ are independently hydrogen, aminocarbonyl, alkoxycarbonyl, optionally substituted alkyl or optionally substituted alkoxy, or $R_6$ and $R_7$, taken together with the carbon to which they are attached, form an optionally substituted 3- to 7-membered ring which optionally incorporates one or two additional heteroatoms, selected from N, O, and S in the ring.

In certain embodiments, $R_6$ and $R_7$ are independently hydrogen or methyl. In certain embodiments, $R_6$ and $R_7$ are independently hydrogen. In certain embodiments, $R_6$ and $R_7$ are independently hydrogen or methyl. In certain embodiments, n is one and $R_6$ and $R_7$ are independently hydrogen or methyl. In certain embodiments, n is one and $R_6$ is methyl and $R_7$ is hydrogen. In certain embodiments, n is two and each $R_6$ and $R_7$ is hydrogen. In certain embodiments, n is three and each $R_6$ and $R_7$ is hydrogen.-methyl-isoxazol-3-yl.

In certain embodiments, $R_3$ is hydrogen, cyano, lower alkyl (such as methyl or ethyl) or halo (such as chloro or fluoro). In certain embodiments, $R_3$ is hydrogen or fluoro.

In certain embodiments, $R_4$ is hydrogen, pyridinyl, halo or optionally substituted lower alkyl. In certain embodiments, $R_4$ is hydrogen, pyridinyl, trifluoromethyl, or fluoro.

In certain embodiments, $R_5$ is hydrogen, pyridinyl, halo or optionally substituted lower alkyl. In certain embodiments, $R_5$ is hydrogen, chloro, fluoro, methyl, or trifluoromethyl.

In certain embodiments, $R_{13}$ is hydrogen, lower alkyl (such as methyl or ethyl), hydroxyl, or halo. hydrogen, halogen, hydroxyl, or lower alkyl In certain embodiments, $R_{13}$ is hydrogen or fluoro.

In certain embodiments, $R_3$, $R_4$, $R_5$, and $R_{13}$ are hydrogen. In certain embodiments, one of $R_3$, $R_4$, $R_5$, and $R_{13}$ is not hydrogen.

In certain embodiments, one of $R_3$, $R_4$, $R_5$, and $R_{13}$ is halo, optionally substituted lower alkyl, or cyano and the others are hydrogen. In certain embodiments one of $R_3$, $R_4$, $R_5$, and $R_{13}$ is halo, methyl or cyano and the others are hydrogen. In certain embodiments two of $R_3$, $R_4$, $R_5$, and $R_{13}$ are halo or cyano and the others are hydrogen.

In certain embodiments, one of $R_3$, $R_4$, $R_5$, and $R_{13}$ is fluoro and the others are hydrogen. In certain embodiments, one of $R_3$, $R_4$, $R_5$, and $R_{13}$ is cyano and the others are hydrogen. In certain embodiments, two of $R_3$, $R_4$, $R_5$, and $R_{13}$ are not hydrogen. In certain embodiments, two of $R_3$, $R_4$, $R_5$, and $R_u$ are halo and the others are hydrogen. In certain embodiments, two of $R_3$, $R_4$, $R_5$, and $R_u$ are fluoro and the others are hydrogen.

In certain embodiments, the chemical entity of Formula I is chosen from a chemical entity of Formula Ib

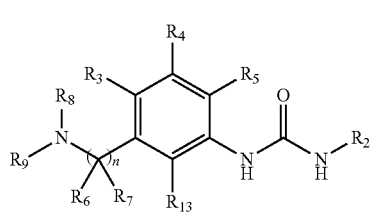

Formula Ib wherein $R_2$, $R_3$, $R_4$, $R_5$, $R_6$, $R_7$, $R_8$, $R_9$, $R_{13}$, and n are as described for compounds of Formula 1.

In certain embodiments, the chemical entity of Formula I is chosen from a chemical entity of Formula Ic

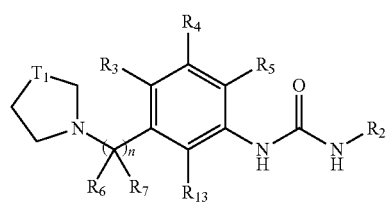

Formula Ic wherein $R_2$, $R_3$, $R_4$, $R_5$, $R_6$, $R_7$, $R_{13}$, and n are as described for compounds of Formula I and wherein $T_1$ is —$CHR_{14}$—, —$NR_{15}CHR_{14}$—, —$CHR_{14}NR_{15}$—, or —$CHR_{14}CHR_{14}$—; and each $R_{14}$ and $R_{15}$ is independently selected from hydrogen, optionally substituted alkyl, optionally substituted acyl, carboxy, optionally substituted lower alkoxycarbonyl, optionally substituted aminocarbonyl, optionally substituted alkoxy, optionally substituted cycloalkoxy, optionally substituted sulfonyl, optionally substituted amino, optionally substituted cycloalkyl, and optionally substituted heterocycloalkyl.

In certain embodiments, $T_1$ is —$NR_{15}CHR_{14}$—, i.e., $R_1$ is a piperazinyl ring substituted with $R_{14}$ and $R_{15}$. In certain embodiments, Ti is —$CHR_{14}$—$CHR_{14}$—.

In certain embodiments, $R_{14}$ and $R_{15}$ are independently selected from hydrogen, methyl, carboxy, methoxycarbonyl, ethoxycarbonyl, propoxycarbonyl, isopropoxycarbonyl, tert-butoxycarbonyl, benzyloxy carbonyl, N,N-dimethylcarbamoyl, acetyl, propionyl, isobutyryl, propoxy, methoxy, cyclohexylmethyloxy, methylsulfonyl, ethylsulfonyl, n-propylsulfonyl, isopropylsulfonyl, azetidin-1-ylsulfonyl, dimethylamino sulfonyl, methanesulfonamido, N-methyl-methanesulfonamido, ethanesulfonamido, N-methyl-ethanesulfonamido, N-methoxycarbonyl-N-methylamino, N-ethoxycarbonyl-N-methylamino, N-isopropoxycarbonyl-N-methylamino, N-tert-butoxycarbonyl-N-methylamino, acetamido, N-methylacetamido, N-methylpropionamido, N-methylisobutyramido, amino, methylamino, dimethylamino, N-methyl-(dimethylamino sulfonyl)amino, and piperidin-1-yl.

In certain embodiments, $R_{14}$ is chosen from hydrogen, methyl, and methoxymethyl.

In certain embodiments, $R_{15}$ is chosen from optionally substituted acyl, optionally substituted lower alkoxycarbonyl, and optionally substituted sulfonyl. In certain embodiments, $R_{15}$ is chosen from lower alkoxycarbonyl, lower alkylsulfonyl, and optionally substituted aminosulfonyl.

In certain embodiments the chemical entity of Formula I is a chemical entity of Formula Id:

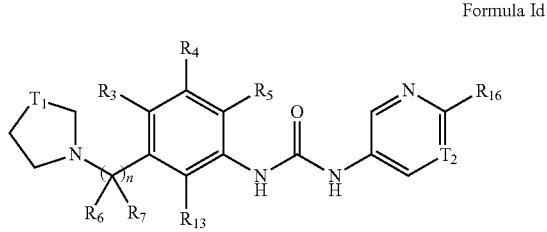

Formula Id wherein $T_1$, $R_3$, $R_4$, $R_5$, $R_6$, $R_7$, $R_{13}$, and n are as described for compounds of Formula Ic and wherein $T_2$ is —C= or —N=; and $R_{16}$ is selected from hydrogen, halo, cyano, optionally substituted acyl, optionally substituted alkyl, and optionally substituted alkoxy.

In certain embodiments, $T_2$ is —C=.

In certain embodiments, $T_2$ is —N=.

In certain embodiments, $R_{16}$ is selected from hydrogen, methyl, fluoro, cyano, methoxy, and acetyl. In certain embodiments, $R_{16}$ is hydrogen or methyl.

In certain embodiments,

W, X, Y and Z are —C=;

n is one, two, or three;

$R_1$ is —$NR_8R_9$ wherein $R_8$ is lower alkyl and $R_9$ is optionally substituted acyl or optionally substituted sulfonyl;

$R_2$ is pyridin-3-yl which is optionally substituted with lower alkyl; phenyl which is optionally substituted with halo (such as fluoro); optionally substituted pyrimidin-5-yl; or optionally substituted isoxazol-3-yl;
$R_3$ is hydrogen or fluoro;
$R_4$ is hydrogen, pyridinyl or fluoro;
$R_5$ is hydrogen or fluoro;
$R_6$ and $R_7$ are independently hydrogen or methyl; and
$R_{13}$ is hydrogen or fluoro.
In certain embodiments,
W, X, Y and Z are —C═;
n is one, two, or three;
$R_1$ is —$NR_8R_9$ wherein $R_8$ is lower alkyl and $R_9$ is optionally substituted acyl or optionally substituted sulfonyl;
$R_2$ is pyridin-3-yl which is optionally substituted with lower alkyl; phenyl which is optionally substituted with halo (such as fluoro); optionally substituted pyrimidin-5-yl; or optionally substituted isoxazol-3-yl;
$R_3$ is hydrogen or fluoro;
$R_4$ is hydrogen, pyridinyl or fluoro;
$R_5$ is hydrogen or fluoro;
$R_6$ and $R_7$ are independently hydrogen or methyl; and
$R_{13}$ is hydrogen or fluoro
wherein
one of $R_3$, $R_4$, and $R_5$ is not hydrogen
In certain embodiments,
W, X, Y and Z are —C═;
n is one, two, or three;
$R_1$ is an optionally substituted 5- to 7-membered nitrogen containing heterocycle which optionally includes an additional oxygen, nitrogen or sulfur in the heterocyclic ring;
$R_2$ is pyridin-3-yl which is optionally substituted with lower alkyl; phenyl which is optionally substituted with halo (such as fluoro); optionally substituted pyrimidin-5-yl; or optionally substituted isoxazol-3-yl.
$R_3$ is hydrogen or fluoro;
$R_4$ is hydrogen, pyridinyl or fluoro;
$R_5$ is hydrogen or fluoro;
$R_6$ and $R_7$ are independently hydrogen or methyl; and
$R_{13}$ is hydrogen or fluoro.
In certain embodiments,
W, X, Y and Z are —C═;
n is one, two, or three;
$R_1$ is an optionally substituted 5- to 7-membered nitrogen containing heterocycle which optionally includes an additional oxygen, nitrogen or sulfur in the heterocyclic ring;
$R_2$ is pyridin-3-yl which is optionally substituted with lower alkyl; phenyl which is optionally substituted with halo (such as fluoro); optionally substituted pyrimidin-5-yl; or optionally substituted isoxazol-3-yl.
$R_3$ is hydrogen or fluoro;
$R_4$ is hydrogen, pyridinyl or fluoro;
$R_5$ is hydrogen or fluoro;
$R_6$ and $R_7$ are independently hydrogen or methyl; and
$R_{13}$ is hydrogen or fluoro, wherein
one of $R_3$, $R_4$, and $R_5$ is not hydrogen.
In certain embodiments, the compound of Formula I is:
methyl 4-[(2-fluoro-3-{[(6-methyl(3-pyridyl))amino]carbonylamino}phenyl)methyl]piperazinecarboxylate;
N-({3-fluoro-5-[(3-pyridylamino)carbonylamino]phenyl}methyl)methoxy-N-methylcarboxamide;
N-[(3-fluoro-5-{[(6-methyl(3-pyridyl))amino]carbonylamino}phenyl)methyl]methoxy-N-methylcarboxamide;
N-[3-({[(dimethylamino)sulfonyl]methylamino}methyl)-5-fluorophenyl](3-pyridylamino)carboxamide;
N-[3-({[(dimethylamino)sulfonyl]methylamino]methyl}-5-fluorophenyl)[(6-methyl(3-pyridyl))amino]carboxamide;
N-(3-{[(ethylsulfonyl)methylamino]methyl}-5-fluorophenyl)[(6-methyl(3-pyridyl))amino]carboxamide;
methyl 4-({3-fluoro-5-[(3-pyridylamino)carbonylamino]phenyl}methyl)piperazinecarboxylate;
N-(3-{[4-(ethylsulfonyl)piperazinyl]methyl}-5-fluorophenyl)(3-pyridylamino)carboxamide;
methyl 4-[(3-fluoro-5-{[(6-methyl(3-pyridyl))amino]carbonylamino}phenyl)methyl]piperazinecarboxylate;
N-(3-{[4-(ethylsulfonyl)piperazinyl]methyl]-5-fluorophenyl)[(6-methyl(3-pyridyl))amino]carboxamide;
N-[3-({4-[(dimethylamino)sulfonyl]piperazinyl}methyl)-5-fluorophenyl][(6-methyl(3-pyridyl))amino]carboxamide;
N-[3-({4-[(dimethylamino)sulfonyl]piperazinyl}methyl)-5-fluorophenyl](3-pyridylamino)carboxamide;
N-[3-({4-[(dimethylamino)sulfonyl]piperazinyl}methyl)-5-fluorophenyl][(4-fluorophenyl)amino]carboxamide;
methyl 4-[(3-fluoro-5-{[(4-fluorophenyl)amino]carbonylamino}phenyl)methyl]piperazinecarboxylate;
N-(3-{[4-(ethylsulfonyl)piperazinyl]methyl}-5-fluorophenyl)[(4-fluorophenyl)amino]carboxamide;
methyl 4-({4-fluoro-3-[(3-pyridylamino)carbonylamino]phenyl}methyl)piperazinecarboxylate;
N-[5-({-4-[(dimethylamino)sulfonyl]piperazinyl}methyl)-2-fluorophenyl](3-pyridylamino)carboxamide;
N-(5-{[4-(ethylsulfonyl)piperazinyl]methyl}-2-fluorophenyl)[(6-methyl(3-pyridyl))amino]carboxamide;
N-(5-{[4-(ethylsulfonyl)piperazinyl]methyl}-2-fluorophenyl)(3-pyridylamino)carboxamide;
N-[5-({-4-[(dimethylamino)sulfonyl]piperazinyl}methyl)-2-fluorophenyl][(6-methyl(3-pyridyl))amino]carboxamide;
methyl 4-[(4-fluoro-3-{[(6-methyl(3-pyridyl))amino]carbonylamino}phenyl)methyl]piperazinecarboxylate;
N-{3-[(4-acetylpiperazinyl)methyl]-5-fluorophenyl}[(6-methyl(3-pyridyl))amino]carboxamide;
N-(5-fluoro-3-{[4-(methylsulfonyl)piperazinyl]methyl}phenyl)[(6-methyl(3-pyridyl))amino]carboxamide;
N-[5-fluoro-3-({4-[(methylethyl)sulfonyl]piperazinyl}methyl)phenyl][(6-methyl(3-pyridyl))amino]carboxamide;
N-(5-fluoro-3-{[4-(2-methoxyacetyl)piperazinyl]methyl}phenyl)[(6-methyl(3-pyridyl))amino]carboxamide;
N-(5-fluoro-3-{[4-(propylsulfonyl)piperazinyl]methyl}phenyl)[(6-methyl(3-pyridyl))amino]carboxamide;
N-[3-({4-[(1E)-1-(dimethylamino)-2-cyano-2-azavinyl]piperazinyl}methyl)-5-fluorophenyl][(6-methyl(3-pyridyl))amino]carboxamide;
N-{5-fluoro-3-[(5-methyl-1,1-dioxo(1,2,5-thiadiazolidin-2-yl))methyl]phenyl}(3-pyridylamino)carboxamide;
N-{5-fluoro-3-[(5-methyl-1,1-dioxo(1,2,5-thiadiazolidin-2-yl))methyl]phenyl}[(6-methyl(3-pyridyl))amino]carboxamide;
N-{5-fluoro-3-[(5-methyl-1,1-dioxo(1,2,5-thiadiazolidin-2-yl))methyl]phenyl}[(4-fluorophenyl)amino]carboxamide;
methyl 4-[(2-fluoro-5-{[(6-methyl(3-pyridyl))amino]carbonylamino}phenyl)methyl]piperazinecarboxylate;
N-(3-{[4-(ethylsulfonyl)piperazinyl]methyl}-4-fluorophenyl)[(6-methyl(3-pyridyl))amino]carboxamide;
N-[3-({4-[(dimethylamino)sulfonyl]piperazinyl}methyl)-4-fluorophenyl][(6-methyl(3-pyridyl))amino]carboxamide;
methyl 4-({2-fluoro-5-[(3-pyridylamino)carbonylamino]phenyl}methyl)piperazinecarboxylate;

N-(3-{[4-(ethylsulfonyl)piperazinyl]methyl}-4-fluorophenyl)(3-pyridylamino)carboxamide;

N-[3-({4-[(dimethylamino)sulfonyl]piperazinyl}methyl)-4-fluorophenyl](3-pyridylamino)carboxamide;

methyl 4-({3-[(3-pyridylamino)carbonylamino]phenyl}methyl)piperazinecarboxylate;

N-(3-{[4-(ethylsulfonyl)piperazinyl]methyl}phenyl)(3-pyridylamino)carboxamide;

N-(3-{[4-(ethylsulfonyl)piperazinyl]methyl}phenyl)[(6-methyl(3-pyridyl))amino]carboxamide;

methyl 4-[(3-{[((6-methyl-3-pyridyl))amino]carbonylamino}phenyl)methyl]piperazinecarboxylate;

N-[3-({4-[(dimethylamino)sulfonyl]piperazinyl}methyl)phenyl](3-pyridylamino)carboxamide;

N-[3-({4-[(dimethylamino)sulfonyl]piperazinyl}methyl)phenyl][(6-methyl(3-pyridyl))amino]carboxamide;

N-{5-fluoro-3-[(3-methyl-2-oxoimidazolidinyl)methyl]phenyl}(3-pyridylamino)carboxamide;

N-{5-fluoro-3-[(3-methyl-2-oxoimidazolidinyl)methyl]phenyl}[(6-methyl(3-pyridyl))amino]carboxamide;

N-{5-fluoro-3-[(4-methyl-3-oxopiperazinyl)methyl]phenyl}(3-pyridylamino)carboxamide;

N-[3-fluoro-5-(piperidylmethyl)phenyl][(6-methyl(3-pyridyl))amino]carboxamide;

N-[3-fluoro-5-(piperidylmethyl)phenyl](3-pyridylamino)carboxamide;

N-[3-({(3S)-4-[(dimethylamino)sulfonyl]-3-(methoxymethyl)piperazinyl}methyl)-5-fluorophenyl](3-pyridylamino)carboxamide;

N-(3-{[(3S)-4-(ethylsulfonyl)-3-(methoxymethyl)piperazinyl]methyl}-5-fluorophenyl)(3-pyridylamino)carboxamide;

methyl(2S)-4-({5-fluoro-3-[(3-pyridylamino)carbonylamino]phenyl}methyl)-2-(methoxymethyl)piperazinecarboxylate;

N-[3-({(3S)-4-[(dimethylamino)sulfonyl]-3-(methoxymethyl)piperazinyl}methyl)-5-fluorophenyl][(6-methyl(3-pyridyl))amino]carboxamide;

N-(3-{[(3S)-4-(ethylsulfonyl)-3-(methoxymethyl)piperazinyl]methyl}-5-fluorophenyl)[(6-methyl(3-pyridyl))amino]carboxamide;

methyl(2S)-4-[(5-fluoro-3-{[(6-methyl(3-pyridyl))amino]carbonylamino}phenyl)methyl]-2-(methoxymethyl)piperazinecarboxylate;

N-[5-fluoro-3-(morpholin-4-ylmethyl)phenyl][(6-methyl(3-pyridyl))amino]carboxamide;

N-[5-fluoro-3-(morpholin-4-ylmethyl)phenyl]-pyridylamino)carboxamide;

N-{3-[(1,1-dioxo(1,4-thiazaperhydroin-4-yl))methyl]-5-fluorophenyl}[(6-methyl(3-pyridyl))amino]carboxamide;

N-{3-[(1,1-dioxo(1,4-thiazaperhydroin-4-yl))methyl]-5-fluorophenyl}(3-pyridylamino)carboxamide;

N-{5-fluoro-3-[(4-methylpiperazinyl)methyl]phenyl}[(6-methyl(3-pyridyl))amino]carboxamide;

N-{5-fluoro-3-[(4-methylpiperazinyl)methyl]phenyl}(3-pyridylamino)carboxamide;

N-{3-[((3S)-3-{[(dimethylamino)sulfonyl]methylamino}pyrrolidinyl)methyl]-5-fluorophenyl}(3-pyridylamino)carboxamide;

N-[3-({(3S)-3-[(ethylsulfonyl)methylamino]pyrrolidinyl}methyl)-5-fluorophenyl](3-pyridylamino)carboxamide;

N-[(3S)-1-({3-fluoro-5-[(3-pyridylamino)carbonylamino]phenyl}methyl)pyrrolidin-3-yl]methoxy-N-methylcarboxamide;

N-{3-[((3S)-3-{[(dimethylamino)sulfonyl]methylamino}pyrrolidinyl)methyl]-5-fluorophenyl}[(6-methyl(3-pyridyl))amino]carboxamide;

N-[3-({(3S)-3-[(ethylsulfonyl)methylamino]pyrrolidinyl}methyl)-5-fluorophenyl][(6-methyl(3-pyridyl))amino]carboxamide;

N-{(3S)-1-[(3-fluoro-5-{[(6-methyl(3-pyridyl))amino]carbonylamino}phenyl)methyl]pyrrolidin-3-yl}methoxy-N-methylcarboxamide;

N-(5-fluoro-3-{[4-(methylsulfonyl)piperidyl]methyl}phenyl)[(6-methyl(3-pyridyl))amino]carboxamide;

N-(5-fluoro-3-{[4-(methylsulfonyl)piperidyl]methyl}phenyl)(3-pyridylamino)carboxamide;

N-(3-{[4-(ethylsulfonyl)piperazinyl]methyl}-5-fluorophenyl)(pyrimidin-5-ylamino)carboxamide;

N-[3-({4-[(dimethylamino)sulfonyl]piperazinyl}methyl)-5-fluorophenyl] (pyrimidin-5-ylamino)carboxamide;

methyl 1-[(3-fluoro-5-{[(6-methyl(3-pyridyl))amino]carbonylamino}phenyl)methyl]piperidine-4-carboxylate;

methyl 1-({3-fluoro-5-[(3-pyridylamino)carbonylamino]phenyl}methyl)piperidine-4-carboxylate;

methyl 4-[(3-fluoro-5-{[(5-methylisoxazol-3-yl)amino]carbonylamino}phenyl)methyl]piperazinecarboxylate;

N-[3-({4-[(dimethylamino)sulfonyl]piperazinyl}methyl)-5-fluorophenyl][(5-methylisoxazol-3-yl)amino]carboxamide;

N-(3-{[4-(ethylsulfonyl)piperazinyl]methyl}-5-fluorophenyl)[(5-methylisoxazol-3-yl)amino]carboxamide;

({5-[((3R)-3-{-[(dimethylamino)sulfonyl]methylamino}piperidyl)methyl]-3-fluorophenyl}amino)-N-(3-pyridyl)carboxamide;

{[5-({(3R)-3-[(ethylsulfonyl)methylamino]piperidyl}methyl)-3-fluorophenyl]amino}-N-(3-pyridyl)carboxamide;

N-[(3R)-1-({5-fluoro-3-[(N-(3-pyridyl)carbamoyl)amino]phenyl}methyl)(3-piperidyl)]methoxy-N-methylcarboxamide;

({5-[((3R)-3-{[(dimethylamino)sulfonyl]methylamino}piperidyl)methyl]-3-fluorophenyl}amino)-N-(6-methyl(3-pyridyl))carboxamide;

{[5-({(3R)-3-[(ethylsulfonyl)methylamino]piperidyl}methyl)-3-fluorophenyl]amino}-N-(6-methyl(3-pyridyl))carboxamide;

N-{(3R)-1-[(5-fluoro-3-{[N-(6-methyl(3-pyridyl))carbamoyl]amino}phenyl)methyl](3-piperidyl)}methoxy-N-methylcarboxamide;

methyl 4-({3-fluoro-5-[(isoxazol-3-ylamino)carbonylamino]phenyl}methyl)piperazinecarboxylate;

N-(3-{[4-(ethylsulfonyl)piperazinyl]methyl}-5-fluorophenyl)(isoxazol-3-ylamino)carboxamide;

N-[3-({4-[(dimethylamino)sulfonyl]piperazinyl}methyl)-5-fluorophenyl](isoxazol-3-ylamino)carboxamide;

N-[5-fluoro-3-({4-[methyl(methylsulfonyl)amino]piperidyl}methyl)phenyl][(6-methyl(3-pyridyl))amino]carboxamide;

N-[3-({4-[(ethylsulfonyl)methylamino]piperidyl}methyl)-5-fluorophenyl][(6-methyl(3-pyridyl))amino]carboxamide;

N-{3-[(4-{[(dimethylamino)sulfonyl]methylamino}piperidyl)methyl]-5-fluorophenyl}[(6-methyl(3-pyridyl))amino]carboxamide;

N-{1-[(3-fluoro-5-{[(6-methyl(3-pyridyl))amino]carbonylamino}phenyl)methyl] (4-piperidyl)}methoxy-N-methylcarboxamide;

N-{1-[(3-fluoro-5-{[(6-methyl(3-pyridyl))amino]carbonylamino}phenyl)methyl] (4-piperidyl)}-N-methylacetamide;
methyl 4-[(3-fluoro-5-{[(2-methylpyrimidin-5-yl)amino]carbonylamino}phenyl)methyl]piperazinecarboxylate;
N-[5-fluoro-3-({4-[methyl(methylsulfonyl)amino]piperidyl}methyl)phenyl](3-pyridylamino)carboxamide;
N-[3-({4-[(ethylsulfonyl)methylamino]piperidyl}methyl)-5-fluorophenyl](3-pyridylamino)carboxamide;
N-{3-[(4-{[(dimethylamino)sulfonyl]methylamino}piperidyl)methyl]-5-fluorophenyl}(3-pyridylamino)carboxamide;
N-[1-({3-fluoro-5-[(3-pyridylamino)carbonylamino]phenyl}methyl)(4-piperidyl)]methoxy-N-methylcarboxamide;
N-[1-({3-fluoro-5-[(3-pyridylamino)carbonylamino]phenyl}methyl)(4-piperidyl)]-N-methylacetamide;
N-[5-fluoro-3-({4-[methyl(methylsulfonyl)amino]piperidyl}methyl)phenyl][(4-fluorophenyl)amino]carboxamide;
N-[3-({4-[(ethylsulfonyl)methylamino]piperidyl}methyl)-5-fluorophenyl][(4-fluorophenyl)amino]carboxamide;
N-{3-[(4-{[(dimethylamino)sulfonyl]methylamino}piperidyl)methyl]-5-fluorophenyl}[(4-fluorophenyl)amino]carboxamide;
N-{1-[(3-fluoro-5-{[(4-fluorophenyl)amino]carbonylamino}phenyl)methyl](4-piperidyl)}methoxy-N-methylcarboxamide;
N-{1-[(3-fluoro-5-{[(4-fluorophenyl)amino]carbonylamino}phenyl)methyl] (4-piperidyl)}-N-methylacetamide;
(tert-butoxy)-N-{1-[(3-fluoro-5-{[(6-methyl(3-pyridyl))amino]carbonylamino}phenyl)methyl] (4-piperidyl)}-N-methylcarboxamide;
(tert-butoxy)-N-[1-({3-fluoro-5-[(3-pyridylamino)carbonylamino]phenyl}methyl)(4-piperidyl)]-N-methylcarboxamide;
(tert-butoxy)-N-{1-[(3-fluoro-5-{[(4-fluorophenyl)amino]carbonylamino}phenyl)methyl] (4-piperidyl)}-N-methylcarboxamide;
N-(5-fluoro-3-{[4-(methylamino)piperidyl]methyl}phenyl)[(6-methyl(3-pyridyl))amino]carboxamide;
N-(5-fluoro-3-{[4-(methylamino)piperidyl]methyl}phenyl)(3-pyridylamino)carboxamide;
methyl 4-({4-fluoro-3-[(1,3-oxazol-2-ylamino)carbonylamino]phenyl}methyl)piperazinecarboxylate;
methyl 4-[(4-fluoro-3-{[(5-methylisoxazol-3-yl)amino]carbonylamino}phenyl)methyl]piperazinecarboxylate;
methyl 4-[(4-fluoro-3-{[(2-methylpyrimidin-5-yl)amino]carbonylamino}phenyl)methyl]piperazinecarboxylate;
methyl 4-[(4-fluoro-3-{[(1-methylpyrazol-3-yl)amino]carbonylamino}phenyl)methyl]piperazinecarboxylate;
1-[(3-fluoro-5-{[(6-methyl(3-pyridyl))amino]carbonylamino}phenyl)methyl]piperidine-4-carboxylic acid;
1-({3-fluoro-5-[(3-pyridylamino)carbonylamino]phenyl}methyl)piperidine-4-carboxylic acid;
N-[2-fluoro-5-(morpholin-4-ylmethyl)phenyl][(6-methyl(3-pyridyl))amino]carboxamide;
methyl 4-({4-fluoro-3-[(pyrimidin-5-ylamino)carbonylamino]phenyl}methyl)piperazinecarboxylate;
N-{(3R)-1-[(4-fluoro-3-{[N-(6-methyl(3-pyridyl))carbamoyl]amino}phenyl)methyl](3-piperidyl)}methoxy-N-methylcarboxamide;
N-{(3R)-1-[(4-fluoro-3-{[N-(6-methyl(3-pyridyl))carbamoyl]amino}phenyl)methyl](3-piperidyl)}ethoxy-N-methylcarboxamide;
N-{(3R)-1-[(4-fluoro-3-{[N-(6-methyl(3-pyridyl))carbamoyl]amino}phenyl)methyl](3-piperidyl)}-N-methyl(methylethoxy)carboxamide;
N-{(3R)-1-[(4-fluoro-3-{[N-(6-methyl(3-pyridyl))carbamoyl]amino}phenyl)methyl](3-piperidyl)}-N-methylacetamide;
N-{(3R)-1-[(4-fluoro-3-{[N-(6-methyl(3-pyridyl))carbamoyl]amino}phenyl)methyl](3-piperidyl)}-N-methylpropanamide;
N-{(3R)-1-[(4-fluoro-3-{[N-(6-methyl(3-pyridyl))carbamoyl]amino}phenyl)methyl](3-piperidyl)}-2-methyl-N-methylpropanamide;
methyl 4-[(4-fluoro-3-{[(5-methyl(1,3,4-oxadiazol-2-yl))amino]carbonylamino}phenyl)methyl]piperazinecarboxylate;
methyl 4-[(4-fluoro-3-[{(4-methyl(1,3-oxazol-2-yl))amino}carbonylamino}phenyl)methyl]piperazinecarboxylate;
methyl 4-[(4-chloro-3-{[(6-methyl(3-pyridyl))amino]carbonylamino}phenyl)methyl]piperazinecarboxylate;
ethyl 4-[(4-fluoro-3-{[(6-methyl(3-pyridyl))amino]carbonylamino}phenyl)methyl]piperazinecarboxylate;
methylethyl 4-[(4-fluoro-3-{[(6-methyl(3-pyridyl))amino]carbonylamino}phenyl)methyl]piperazinecarboxylate;
N-{5-[(4-acetylpiperazinyl)methyl]-2-fluorophenyl}[(6-methyl(3-pyridyl))amino]carboxamide;
N-{2-fluoro-5-[(4-propanoylpiperazinyl)methyl]phenyl}[(6-methyl(3-pyridyl))amino]carboxamide;
N-(2-fluoro-5-{[4-(2-methylpropanoyl)piperazinyl]methyl}phenyl)[(6-methyl(3-pyridyl))amino]carboxamide;
N-[5-({(3R)-3-[(tert-butoxy)-N-methylcarbonylamino]pyrrolidinyl}methyl)-2-fluorophenyl][(6-methyl(3-pyridyl))amino]carboxamide;
N-(5-{[(3R)-3-(methylamino)pyrrolidinyl]methyl}-2-fluorophenyl)[(6-methyl(3-pyridyl))amino]carboxamide;
N-(5-{[(3R)-3-(methoxy-N-methylcarbonylamino)pyrrolidinyl]methyl}-2-fluorophenyl)[(6-methyl(3-pyridyl))amino]carboxamide;
N-(5-{[(3R)-3-(ethoxy-N-methylcarbonylamino)pyrrolidinyl]methyl}-2-fluorophenyl)[(6-methyl(3-pyridyl))amino]carboxamide;
N-[5-({(3R)-3-[N-methyl(methylethoxy)carboxamino]pyrrolidinyl}methyl)-2-fluorophenyl][(6-methyl(3-pyridyl))amino]carboxamide;
N-{(3R)-1-[(4-fluoro-3-{[(6-methyl(3-pyridyl))amino]carbonylamino}phenyl)methyl]pyrrolidin-3-yl}-N-methylacetamide;
N-(5-{[4-(N,N-dimethylcarbamoyl)piperidyl]methyl}-3-fluorophenyl)[(6-methyl(3-pyridyl))amino]carboxamide;
N-(3-fluoro-5-{[4-(N-methylcarbamoyl)piperidyl]methyl}phenyl)[(6-methyl(3-pyridyl))amino]carboxamide;
N-{(3S)-1-[(4-fluoro-3-{[(6-methyl(3-pyridyl))amino]carbonylamino}phenyl)methyl](3-piperidyl)}(tert-butoxy)-N-methylcarboxamide;
N-{2-fluoro-5-[(5-propanoyl-2,5-diazabicyclo[2.2.1]hept-2-yl)methyl]phenyl}[(6-methyl(3-pyridyl))amino]carboxamide;
methyl 4-[(4-methyl-3-{[(6-methyl(3-pyridyl))amino]carbonylamino}phenyl)methyl]piperazinecarboxylate;
tert-butyl(2S)-4-[(4-fluoro-3-{[(6-methyl(3-pyridyl))amino]carbonylamino}phenyl)methyl]-2-(methoxymethyl)piperazinecarboxylate;
methyl(2S)-4-[(4-fluoro-3-{[(6-methyl(3-pyridyl))amino]carbonylamino}phenyl)methyl]-2-(methoxymethyl)piperazinecarboxylate;

ethyl(2S)-4-[(4-fluoro-3-{[(6-methyl(3-pyridyl))amino]carbonylamino}phenyl)methyl]-2-(methoxymethyl)piperazinecarboxylate;

methylethyl(2S)-4-[(4-fluoro-3-{[(6-methyl(3-pyridyl))amino]carbonylamino}phenyl)methyl]-2-(methoxymethyl)piperazinecarboxylate;

N-(5-{[(3S)-4-acetyl-3-(methoxymethyl)piperazinyl]methyl}-2-fluorophenyl)[(6-methyl(3-pyridyl))amino]carboxamide;

N-(5-{[(3S)-3-(methoxymethyl)-4-propanoylpiperazinyl]methyl}-2-fluorophenyl)[(6-methyl(3-pyridyl))amino]carboxamide;

N-(5-{[(3S)-3-(methoxymethyl)-4-(2-methylpropanoyl)piperazinyl]methyl}-2-fluorophenyl)[(6-methyl(3-pyridyl))amino]carboxamide;

N-(5-{[(3S)-3-(methoxy-N-methylcarbonylamino)pyrrolidinyl]methyl}-2-fluorophenyl)[(6-methyl(3-pyridyl))amino]carboxamide;

N-(5-{[(3S)-3-(ethoxy-N-methylcarbonylamino)pyrrolidinyl]methyl}-2-fluorophenyl)[(6-methyl(3-pyridyl))amino]carboxamide;

N-[5-({(3S)-3[N-methyl(methylethoxy)carbonylamino]pyrrolidinyl}methyl)-2-fluorophenyl][(6-methyl(3-pyridyl))amino]carboxamide;

N-{(3S)-1-[(4-fluoro-3-{[(6-methyl(3-pyridyl))amino]carbonylamino}phenyl)methyl]pyrrolidin-3-yl}-N-methylacetamide;

N-{(3S)-1-[(4-fluoro-3-{[(6-methyl(3-pyridyl))amino]carbonylamino}phenyl)methyl]pyrrolidin-3-yl}-N-methylpropanamide;

N-{(3S)-1-[(4-fluoro-3-{[(6-methyl(3-pyridyl))amino]carbonylamino}phenyl)methyl]pyrrolidin-3-yl}-2-methyl-N-methylpropanamide;

N-(2-fluoro-5-{[4-(methoxy-N-methylcarbonylamino)piperidyl]methyl}phenyl)[(6-methyl(3-pyridyl))amino]carboxamide;

N-(5-{[4-(ethoxy-N-methylcarbonylamino)piperidyl]methyl}-2-fluorophenyl)[(6-methyl(3-pyridyl))amino]carboxamide;

N-[2-fluoro-5-({4-[N-methyl(methylethoxy)carbonylamino]piperidyl}methyl)phenyl][(6-methyl(3-pyridyl))amino]carboxamide;

N-{1-[(4-fluoro-3-{[(6-methyl(3-pyridyl))amino]carbonylamino}phenyl)methyl] (4-piperidyl)}-N-methylacetamide;

N-{1-[(4-fluoro-3-{[(6-methyl(3-pyridyl))amino]carbonylamino}phenyl)methyl](4-piperidyl)}-N-methylpropanamide;

N-{1-[(4-fluoro-3-{[(6-methyl(3-pyridyl))amino]carbonylamino}phenyl)methyl](4-piperidyl)}-2-methyl-N-methylpropanamide;

N-{(3R)-1-[(4-fluoro-3-{[(6-methyl(3-pyridyl))amino]carbonylamino}phenyl)methyl]pyrrolidin-3-yl}-N-methylpropanamide;

N-{(3R)-1-[(4-fluoro-3-{[(6-methyl(3-pyridyl))amino]carbonylamino}phenyl)methyl]pyrrolidin-3-yl}-2-methyl-N-methylpropanamide;

N-{5-[((3S,5R)-3,5-dimethylmorpholin-4-yl)methyl]-2-fluorophenyl}[(6-methyl(3-pyridyl))amino]carboxamide;

N-{5-[((1S,4S)-5-oxa-2-azabicyclo[2.2.1]hept-2-yl)methyl]-2-fluorophenyl}[(6-methyl(3-pyridyl))amino]carboxamide;

N-{(3S)-1-[(4-fluoro-3-{[(6-methyl(3-pyridyl))amino]carbonylamino}phenyl)methyl](3-piperidyl)}methoxy-N-methylcarboxamide;

N-{(3S)-1-[(4-fluoro-3-{[(6-methyl(3-pyridyl))amino]carbonylamino}phenyl)methyl](3-piperidyl)}ethoxy-N-methylcarboxamide;

N-{(3S)-1-[(4-fluoro-3-{[(6-methyl(3-pyridyl))amino]carbonylamino}phenyl)methyl](3-piperidyl)}-N-methyl(methylethoxy)carboxamide;

tert-butyl 4-[(4-fluoro-3-{[(6-methyl(3-pyridyl))amino]carbonylamino}phenyl)methyl]piperazinecarboxylate;

N-{(3S)-1-[(4-fluoro-3-{[(6-methyl(3-pyridyl))amino]carbonylamino}phenyl)methyl](3-piperidyl)}-N-methylacetamide;

N-[2-fluoro-5-(piperazinylmethyl)phenyl][(6-methyl(3-pyridyl))amino]carboxamide;

methyl(2R)-4-[(4-fluoro-3-{[(6-methyl(3-pyridyl))amino]carbonylamino}phenyl)methyl]-2-(methoxymethyl)piperazinecarboxylate;

N-(5-{[(3R)-4-acetyl-3-(methoxymethyl)piperazinyl]methyl}-2-fluorophenyl)[(6-methyl(3-pyridyl))amino]carboxamide;

ethyl(2R)-4-[(4-fluoro-3-{[(6-methyl(3-pyridyl))amino]carbonylamino}phenyl)methyl]-2-(methoxymethyl)piperazinecarboxylate;

methylethyl(2R)-4-[(4-fluoro-3-{[(6-methyl(3-pyridyl))amino]carbonylamino}phenyl)methyl]-2-(methoxymethyl)piperazinecarboxylate;

N-(5-{[(3S)-3-(methoxymethyl)-4-(methylsulfonyl)piperazinyl]methyl}-2-fluorophenyl)[(6-methyl(3-pyridyl))amino]carboxamide;

N-(5-{[(3S)-3-(methylamino)piperidyl]methyl}-2-fluorophenyl)[(6-methyl(3-pyridyl))amino]carboxamide;

N-{(3S)-1-[(4-fluoro-3-{[(6-methyl(3-pyridyl))amino]carbonylamino}phenyl)methyl](3-piperidyl)}-N-methylpropanamide;

N-{(3S)-1-[(4-fluoro-3-{[(6-methyl(3-pyridyl))amino]carbonylamino}phenyl)methyl](3-piperidyl)}-2-methyl-N-methylpropanamide;

tert-butyl 4-[(4-fluoro-3-{[(6-methyl(3-pyridyl))amino]carbonylamino}phenyl)methyl]-1,4-diazaperhydroepinecarboxylate;

N-(3-{[4-(N,N-dimethylcarbamoyl)piperidyl]methyl}-5-fluorophenyl)(3-pyridylamino)carboxamide;

methyl 4-({4-fluoro-3-[(pyridazin-4-ylamino)carbonylamino]phenyl}methyl)piperazinecarboxylate;

N-(5-{[(3R)-4-(ethylsulfonyl)-3-(methoxymethyl)piperazinyl]methyl}-2-fluorophenyl)[(6-methyl(3-pyridyl))amino]carboxamide;

N-(5-fluoro-3-{[4-(N-methylcarbamoyl)piperidyl]methyl}phenyl)(3-pyridylamino)carboxamide;

methyl 4-({4-fluoro-3-[(isoxazol-3-ylamino)carbonylamino]phenyl}methyl)piperazinecarboxylate;

N-{3-[((1S)-7-oxo-8-oxa-3,6-diazabicyclo[4.3.0]non-3-yl)methyl]-5-fluorophenyl}[(6-methyl(3-pyridyl))amino]carboxamide;

N-{5-[((1S)-7-oxo-8-oxa-3,6-diazabicyclo[4.3.0]non-3-yl)methyl]-2-fluorophenyl}[(6-methyl(3-pyridyl))amino]carboxamide;

methyl 4-[(5-fluoro-3-{[(6-methyl(3-pyridyl))amino]carbonylamino}phenyl)ethyl]piperazinecarboxylate;

ethyl 4-[(5-fluoro-3-{[(6-methyl(3-pyridyl))amino]carbonylamino}phenyl)ethyl]piperazinecarboxylate;

N-{3-[(4-acetylpiperazinyl)ethyl]-5-fluorophenyl}[(6-methyl(3-pyridyl))amino]carboxamide;

N-[5-(1,4-diazaperhydroepinylmethyl)-2-fluorophenyl][(6-methyl(3-pyridyl))amino]carboxamide;

methyl 4-[(4-fluoro-3-{[(6-methyl(3-pyridyl))amino]carbonylamino}phenyl)methyl]-1,4-diazaperhydroepinecarboxylate;

ethyl 4-[(4-fluoro-3-{[(6-methyl(3-pyridyl))amino]carbonylamino}phenyl)methyl]-1,4-diazaperhydroepinecarboxylate;
methylethyl 4-[(4-fluoro-3-{[(6-methyl(3-pyridyl))amino]carbonylamino}phenyl)methyl]-1,4-diazaperhydroepinecarboxylate;
N-{5-[(4-acetyl(1,4-diazaperhydroepinyl))methyl]-2-fluorophenyl}[(6-methyl(3-pyridyl))amino]carboxamide;
N-{5-[(1,4-dioxa-8-azaspiro[4.5]dec-8-yl)methyl]-2-fluorophenyl}[(6-methyl(3-pyridyl))amino]carboxamide;
N-{2-fluoro-5-[(4-methoxypiperidyl)methyl]phenyl}[(6-methyl(3-pyridyl))amino]carboxamide;
N-[5-(azaperhydroepinylmethyl)-2-fluorophenyl][(6-methyl(3-pyridyl))amino]carboxamide;
N-{2-fluoro-5-[(4-piperidylpiperidyl)methyl]phenyl}[(6-methyl(3-pyridyl))amino]carboxamide;
N-(5-{[4-(cyclohexylmethoxy)piperidyl]methyl}-2-fluorophenyl)[(6-methyl(3-pyridyl))amino]carboxamide;
N-(2-fluoro-5-{[2-(hydroxymethyl)morpholin-4-yl]methyl}phenyl)[(6-methyl(3-pyridyl))amino]carboxamide;
N-(2-fluoro-5-{[2-(methoxymethyl)morpholin-4-yl]methyl}phenyl)[(6-methyl(3-pyridyl))amino]carboxamide;
methyl 4-[(2,4-difluoro-5-{[(6-methyl(3-pyridyl))amino]carbonylamino}phenyl)methyl]piperazinecarboxylate;
N-{2-fluoro-5-[(4-propoxypiperidyl)methyl]phenyl}[(6-methyl(3-pyridyl))amino]carboxamide;
N-{2-fluoro-5-[(4-methylpiperidyl)methyl]phenyl}[(6-methyl(3-pyridyl))amino]carboxamide;
N-[5-({4-[(dimethylamino)sulfonyl](1,4-diazaperhydroepinyl)}methyl)-2-fluorophenyl][(6-methyl(3-pyridyl))amino]carboxamide;
propyl 4-[(4-fluoro-3-{[(6-methyl(3-pyridyl))amino]carbonylamino}phenyl)methyl]-1,4-diazaperhydroepinecarboxylate;
N-{3-[((1R)-7-oxo-8-oxa-3,6-diazabicyclo[4.3.0]non-3-yl)methyl]-5-fluorophenyl}[(6-methyl(3-pyridyl))amino]carboxamide;
N-(2-fluoro-5-{[4-(methylsulfonyl)(1,4-diazaperhydroepinyl)]methyl}phenyl)[(6-methyl(3-pyridyl))amino]carboxamide;
N-{3-[((1R)-8-methyl-7,7-dioxo-7-thia-3,6,8-triazabicyclo[4.3.0]non-3-yl)methyl]-5-fluorophenyl}[(6-methyl(3-pyridyl))amino]carboxamide;
N-(5-{[4-(ethylsulfonyl)(1,4-diazaperhydroepinyl)]methyl}-2-fluorophenyl)[(6-methyl(3-pyridyl))amino]carboxamide;
N-{5-[((1R)-8-methyl-7,7-dioxo-7-thia-3,6,8-triazabicyclo[4.3.0]non-3-yl)methyl]-2-fluorophenyl}[(6-methyl(3-pyridyl))amino]carboxamide;
N-[2-fluoro-5-({4-[(methylethyl)sulfonyl](1,4-diazaperhydroepinyl)}methyl)phenyl][(6-methyl(3-pyridyl))amino]carboxamide;
N-{3-[((1S)-8-methyl-7,7-dioxo-7-thia-3,6,8-triazabicyclo[4.3.0]non-3-yl)methyl]-5-fluorophenyl}[(6-methyl(3-pyridyl))amino]carboxamide;
N-{5-[((1S)-8-methyl-7,7-dioxo-7-thia-3,6,8-triazabicyclo[4.3.0]non-3-yl)methyl]-2-fluorophenyl}[(6-methyl(3-pyridyl))amino]carboxamide;
N-{5-[((1R)-7-oxo-8-oxa-3,6-diazabicyclo[4.3.0]non-3-yl)methyl]-2-fluorophenyl}[(6-methyl(3-pyridyl))amino]carboxamide;
methyl 4-[(4-fluoro-3-{[(6-methoxy(3-pyridyl))amino]carbonylamino}phenyl)methyl]piperazinecarboxylate;
methyl 4-[(2,4,5-trifluoro-3-{[(6-methyl(3-pyridyl))amino]carbonylamino}phenyl)methyl]piperazinecarboxylate;
N-[2-fluoro-5-({4-[methyl(methylsulfonyl)amino]piperidyl}methyl)phenyl][(6-methyl(3-pyridyl))amino]carboxamide;
N-{3-[3-(4-acetylpiperazinyl)propyl]-5-fluorophenyl}[(6-methyl(3-pyridyl))amino]carboxamide;
methyl 4-[3-(3-fluoro-5-{[(6-methyl(3-pyridyl))amino]carbonylamino}phenyl)propyl]piperazinecarboxylate;
(tert-butoxy)-N-{1-[(4-fluoro-3-{[(4-fluorophenyl)amino]carbonylamino}phenyl)methyl] (4-piperidyl)}-N-methylcarboxamide;
N-(2-fluoro-5-{[4-(methylamino)piperidyl]methyl}phenyl)[(4-fluorophenyl)amino]carboxamide
methyl 4-[(3-{[(6-cyano(3-pyridyl))amino]carbonylamino}-5-fluorophenyl)methyl]piperazinecarboxylate;
ethyl 4-[(3-{[(6-cyano(3-pyridyl))amino]carbonylamino}-5-fluorophenyl)methyl]piperazinecarboxylate;
methylethyl 4-[(3-{[(6-cyano(3-pyridyl))amino]carbonylamino}-5-fluorophenyl)methyl]piperazinecarboxylate;
N-{3-[(4-acetylpiperazinyl)methyl]-5-fluorophenyl}[(6-cyano(3-pyridyl))amino]carboxamide;
N-[3-({4-[(dimethylamino)sulfonyl]piperazinyl}methyl)-5-fluorophenyl][(6-cyano(3-pyridyl))amino]carboxamide;
[(6-cyano(3-pyridyl))amino]-N-(3-{[4-(ethylsulfonyl)piperazinyl]methyl}-5-fluorophenyl)carboxamide;
N-[2-fluoro-5-({4-[methyl(methylsulfonyl)amino]piperidyl}methyl)phenyl][(4-fluorophenyl)amino]carboxamide;
N-[5-({4-[(ethylsulfonyl)methylamino]piperidyl}methyl)-2-fluorophenyl][(4-fluorophenyl)amino]carboxamide;
tert-butyl(3S)-3-{[(4-fluoro-3-{[(6-methyl(3-pyridyl))amino]carbonylamino}phenyl)methyl]methylamino}pyrrolidinecarboxylate;
methyl(3S)-3-{[(4-fluoro-3-{[(6-methyl(3-pyridyl))amino]carbonylamino}phenyl)methyl]methylamino}pyrrolidinecarboxylate;
methyl(3R)-3-{[(4-fluoro-3-{[(6-methyl(3-pyridyl))amino]carbonylamino}phenyl)methyl]methylamino}pyrrolidinecarboxylate;
methyl 4-[(2-methyl-3-{[(6-methyl(3-pyridyl))amino]carbonylamino}phenyl)methyl]piperazinecarboxylate;
methyl 4-[(2-chloro-5-{[(6-methyl(3-pyridyl))amino]carbonylamino}phenyl)methyl]piperazinecarboxylate;
2-{4-[(3-fluoro-5-{[(6-methyl(3-pyridyl))amino]carbonylamino}phenyl)methyl]piperazinyl}-N,N-dimethylacetamide;
ethyl 4-[(3-{[(6-acetyl(3-pyridyl))amino]carbonylamino}-5-fluorophenyl)methyl]piperazinecarboxylate;
N-{3-[3-(4-acetylpiperazinyl)propyl]-5-fluorophenyl}(3-pyridylamino)carboxamide;
methyl 4-(3-{3-fluoro-5-[(3-pyridylamino)carbonylamino]phenyl}propyl)piperazinecarboxylate;
N-(3-{3-[4-(ethylsulfonyl)piperazinyl]propyl}-5-fluorophenyl)(3-pyridylamino)carboxamide;
ethyl 4-[3-(3-fluoro-5-{[(6-methyl(3-pyridyl))amino]carbonylamino}phenyl)propyl]piperazinecarboxylate;
methylethyl 4-[3-(3-fluoro-5-{[(6-methyl(3-pyridyl))amino]carbonylamino}phenyl)propyl]piperazinecarboxylate;
N-(3-{3-[4-(ethylsulfonyl)piperazinyl]propyl}-5-fluorophenyl)[(6-methyl(3-pyridyl))amino]carboxamide;
N-[3-(3-{4-[(dimethylamino)sulfonyl]piperazinyl}propyl)-5-fluorophenyl][(6-methyl(3-pyridyl))amino]carboxamide;
N-{3-[3-(4-acetylpiperazinyl)propyl]-5-fluorophenyl}[(6-methoxy(3-pyridyl))amino]carboxamide;
methyl 4-[3-(3-fluoro-5-{[(6-methoxy(3-pyridyl))amino]carbonylamino}phenyl)propyl]piperazinecarboxylate;

N-(3-{3-[4-(ethylsulfonyl)piperazinyl]propyl}-5-fluorophenyl)[(6-methoxy(3-pyridyl))amino]carboxamide;
methyl 4-[(3-{[(6-acetyl(3-pyridyl))amino]carbonylamino}-5-fluorophenyl)methyl]piperazinecarboxylate;
N-(5-{[((3S)pyrrolidin-3-yl)methylamino]methyl}-2-fluorophenyl)[(6-methyl(3-pyridyl))amino]carboxamide;
tert-butyl(3R)-3-{[(4-fluoro-3-{[(6-methyl(3-pyridyl))amino]carbonylamino}phenyl)methyl]methylamino}pyrrolidinecarboxylate;
N-(5-{[((3R)pyrrolidin-3-yl)methylamino]methyl}-2-fluorophenyl)[(6-methyl(3-pyridyl))amino]carboxamide;
N-ethyl-N-{1-[(4-fluoro-3-{[(6-methyl(3-pyridyl))amino]carbonylamino}phenyl)methyl] (4-piperidyl)}methoxycarboxamide;
ethoxy-N-ethyl-N-{1-[(4-fluoro-3-{[(6-methyl(3-pyridyl))amino]carbonylamino}phenyl)methyl] (4-piperidyl)}carboxamide;
N-[5-({4-[ethyl(ethylsulfonyl)amino]piperidyl}methyl)-2-fluorophenyl][(6-methyl(3-pyridyl))amino]carboxamide;
N-ethyl-N-{-1-[(4-fluoro-3-{[(6-methyl(3-pyridyl))amino]carbonylamino}phenyl)methyl] (4-piperidyl)}acetamide;
methyl 4-[(3-{[(6-cyano(3-pyridyl))amino]carbonylamino}-4-fluorophenyl)methyl]piperazinecarboxylate;
ethyl 4-[(3-{[(6-cyano(3-pyridyl))amino]carbonylamino}-4-fluorophenyl)methyl]piperazinecarboxylate;
methylethyl 4-[(3-{[(6-cyano(3-pyridyl))amino]carbonylamino}-4-fluorophenyl)methyl]piperazinecarboxylate;
N-{5-[(4-acetylpiperazinyl)methyl]-2-fluorophenyl}[(6-cyano(3-pyridyl))amino]carboxamide;
methyl 4-[(3-{[(6-methyl(3-pyridyl))amino]carbonylamino}-5-(trifluoromethyl)phenyl)methyl]piperazinecarboxylate;
methyl 4-[(2-methyl-5-{[(6-methyl(3-pyridyl))amino]carbonylamino}phenyl)methyl]piperazinecarboxylate;
methyl 4-[(2,6-difluoro-3-{[(6-methyl(3-pyridyl))amino]carbonylamino}phenyl)methyl]piperazinecarboxylate;
methyl 4-[(4-chloro-2-fluoro-5-{[(6-methyl(3-pyridyl))amino]carbonylamino}phenyl)methyl]piperazinecarboxylate;
tert-butyl 4-[(1R)-1-(5-fluoro-3-{[(6-methyl(3-pyridyl))amino]carbonylamino}phenyl)ethyl]piperazinecarboxylate;
methyl 4-[(1R)-1-(5-fluoro-3-{[(6-methyl(3-pyridyl))amino]carbonylamino}phenyl)ethyl]piperazinecarboxylate;
ethyl 4-[(1R)-1-(5-fluoro-3-{[(6-methyl(3-pyridyl))amino]carbonylamino}phenyl)ethyl]piperazinecarboxylate;
ethyl 4-[(3-{[(6-acetyl(3-pyridyl))amino]carbonylamino}-4-fluorophenyl)methyl]piperazinecarboxylate;
methylethyl 4-[(3-{[(6-acetyl(3-pyridyl))amino]carbonylamino}-4-fluorophenyl)methyl]piperazinecarboxylate;
[(6-acetyl(3-pyridyl))amino]-N-{5-[(4-acetylpiperazinyl)methyl]-2-fluorophenyl}carboxamide;
methyl 4-{[(4-fluoro-3-{[(6-methyl(3-pyridyl))amino]carbonylamino}phenyl)methyl]methylamino}piperidinecarboxylate;
N-(5-{[(1-acetyl(4-piperidyl))methylamino]methyl}-2-fluorophenyl)[(6-methyl(3-pyridyl))amino]carboxamide;
N-[5-({[1-(ethylsulfonyl)(4-piperidyl)]methylamino}methyl)-2-fluorophenyl][(6-methyl(3-pyridyl))amino]carboxamide;
N-{5-[({2-[(tert-butoxy)-N-methylcarbonylamino]ethyl}methylamino)methyl]-2-fluorophenyl}[(6-methyl(3-pyridyl))amino]carboxamide;
N-{5-[({2-[(tert-butoxy)-N-methylcarbonylamino]ethyl}methylamino)methyl]-2-fluorophenyl}[(4-fluorophenyl)amino]carboxamide;
methyl 4-[(2-chloro-3-{[(6-methyl(3-pyridyl))amino]carbonylamino}phenyl)methyl]piperazinecarboxylate;
methyl 4-[(3-{[(6-methyl(3-pyridyl))amino]carbonylamino}-4-(trifluoromethyl)phenyl)methyl]piperazinecarboxylate;
tert-butyl 4-[(1S)-1-(5-fluoro-3-{[(6-methyl(3-pyridyl))amino]carbonylamino}phenyl)ethyl]piperazinecarboxylate;
methyl 4-[(1S)-1-(5-fluoro-3-{[(6-methyl(3-pyridyl))amino]carbonylamino}phenyl)ethyl]piperazinecarboxylate;
ethyl 4-[(1S)-1-(5-fluoro-3-{[(6-methyl(3-pyridyl))amino]carbonylamino}phenyl)ethyl]piperazinecarboxylate;
methyl 4-[(3-{[(6-acetyl(3-pyridyl))amino]carbonylamino}-4-fluorophenyl)methyl]piperazinecarboxylate;
N-[2-fluoro-5-(morpholin-4-ylmethyl)phenyl][(4-fluorophenyl)amino]carboxamide;
N-[2-fluoro-5-({methyl[2-(methylamino)ethyl]amino}methyl)phenyl][(6-methyl(3-pyridyl))amino]carboxamide;
N-[2-fluoro-5-({methyl [2-(methylamino)ethyl]amino}methyl)phenyl][(4-fluorophenyl)amino]carboxamide;
N-(2-{[(4-fluoro-3-{[(4-fluorophenyl)amino]carbonylamino}phenyl)methyl]methylamino}ethyl)methoxy-N-methylcarboxamide;
N-(2-{[(4-fluoro-3-{[(4-fluorophenyl)amino]carbonylamino}phenyl)methyl]methylamino}ethyl)-N-methylacetamide;
methyl 4-[(2-cyano-5-{[(6-methyl(3-pyridyl))amino]carbonylamino}phenyl)methyl]piperazinecarboxylate;
methyl 4-[(3,4-difluoro-5-{[(6-methyl(3-pyridyl))amino]carbonylamino}phenyl)methyl]piperazinecarboxylate;
N-{2-fluoro-5-[(methyl {2-[methyl(methylsulfonyl)amino]ethyl}amino)methyl]phenyl}[(4-fluorophenyl)amino]carboxamide;
N-{5-[({2-[(ethylsulfonyl)methylamino]ethyl}methylamino)methyl]-2-fluorophenyl}[(4-fluorophenyl)amino]carboxamide;
N-[5-fluoro-3-(morpholin-4-ylmethyl)phenyl][(4-fluorophenyl)amino]carboxamide;
N-(2-{[(4-fluoro-3-{[(6-methyl(3-pyridyl))amino]carbonylamino}phenyl)methyl]methylamino}ethyl)methoxy-N-methylcarboxamide;
N-(2-{[(4-fluoro-3-{[(6-methyl(3-pyridyl))amino]carbonylamino}phenyl)methyl]methylamino}ethyl)-N-methylacetamide;
tert-butyl 4-[(1S)-1-(3-{[(6-methyl(3-pyridyl))amino]carbonylamino}phenyl)ethyl]piperazinecarboxylate;
N-[3-((1S)-1-piperazinylethyl)phenyl][(6-methyl(3-pyridyl))amino]carboxamide;
methyl 4-[(1S)-1-(3-{[(6-methyl(3-pyridyl))amino]carbonylamino}phenyl)ethyl]piperazinecarboxylate;
ethyl 4-[(1S)-1-(3-{[(6-methyl(3-pyridyl))amino]carbonylamino}phenyl)ethyl]piperazinecarboxylate;
N-{3-((1S)-1-[4-(ethylsulfonyl)piperazinyl]ethyl}phenyl)[(6-methyl(3-pyridyl))amino]carboxamide;
N-{3-[(1S)-1-(4-acetylpiperazinyl)ethyl]phenyl}[(6-methyl(3-pyridyl))amino]carboxamide;
N-{2-fluoro-5-[(methyl {2-[methyl(methylsulfonyl)amino]ethyl}amino)methyl]phenyl}[(6-methyl(3-pyridyl))amino]carboxamide;
N-{5-[({2-[(ethylsulfonyl)methylamino]ethyl}methylamino)methyl]-2-fluorophenyl}[(6-methyl(3-pyridyl))amino]carboxamide;
methyl 4-[(1R)-1-(3-{[(6-methyl(3-pyridyl))amino]carbonylamino}phenyl)ethyl]piperazinecarboxylate;

ethyl 4-[(1R)-1-(3-{[(6-methyl(3-pyridyl))amino]carbonylamino}phenyl)ethyl]piperazinecarboxylate;
methyl 4-(5-{[(6-methyl-3-pyridyl)amino]carbonylamino}-1,2,3,4-tetrahydronaphthyl)piperazinecarboxylate;
methyl 4-[(1S)-1-(2-fluoro-3-{[(6-methyl(3-pyridyl))amino]carbonylamino}phenyl)ethyl]piperazinecarboxylate;
ethyl 4-[(1S)-1-(2-fluoro-3-{[(6-methyl(3-pyridyl))amino]carbonylamino}phenyl)ethyl]piperazinecarboxylate;
N-{3-[(1S)-1-(4-acetylpiperazinyl)ethyl]-2-fluorophenyl}[(6-methyl(3-pyridyl))amino]carboxamide;
methyl(3R)-4-methyl-3-[(3-{[(6-methyl(3-pyridyl))amino]carbonylamino}phenyl)methyl]piperazinecarboxylate;
methyl(3S)-4-methyl-3-[(3-{[(6-methyl(3-pyridyl))amino]carbonylamino}phenyl)methyl]piperazinecarboxylate;
methyl 4-[(2,4-difluoro-3-{[(6-methyl(3-pyridyl))amino]carbonylamino}phenyl)methyl]piperazinecarboxylate;
(tert-butoxy)-N-[2-(5-{[(6-methyl(3-pyridyl))amino]carbonylamino}(2-1,2,3,4-tetrahydroisoquinolyl))ethyl]carboxamide;
N-[2-(2-amino ethyl)(5-1,2,3,4-tetrahydroisoquinolyl)][(6-methyl(3-pyridyl))amino]carboxamide;
methyl 4-[(2,5-difluoro-3-{[(6-methyl(3-pyridyl))amino]carbonylamino}phenyl)methyl]piperazinecarboxylate;
methoxy-N-[2-(5-{[(6-methyl(3-pyridyl))amino]carbonylamino}(2-1,2,3,4-tetrahydroisoquinolyl))ethyl]carboxamide;
methyl {methoxy-N-[2-(5-{[(6-methyl(3-pyridyl))amino]carbonylamino}(2-1,2,3,4-tetrahydroisoquinolyl))ethyl]carbonylamino}formate;
(tert-butoxy)-N-methyl-N-[2-(5-{[(6-methyl(3-pyridyl))amino]carbonylamino}(2-1,2,3,4-tetrahydroisoquinolyl))ethyl]carboxamide;
[(6-methyl(3-pyridyl))amino]-N-{2-[2-(methylamino)ethyl](5-1,2,3,4-tetrahydroisoquinolyl)}carboxamide;
methyl 4-[2-(3-{[(6-methyl-3-pyridyl)amino]carbonylamino}phenyl)ethyl]piperazinecarboxylate;
ethyl 4-[2-(3-{[(6-methyl-3-pyridyl)amino]carbonylamino}phenyl)ethyl]piperazinecarboxylate;
N-(3-{2-[4-(ethylsulfonyl)piperazinyl]ethyl}phenyl)[(6-methyl(3-pyridyl))amino]carboxamide;
N-[2-(5-{[(6-methyl-3-pyridyl)amino]carbonylamino}-2-1,2,3,4-tetrahydroisoquinolyl)ethyl]acetamide;
N-[2-(2-{[(dimethylamino)sulfonyl]amino}ethyl)(5-1,2,3,4-tetrahydroisoquinolyl)][(6-methyl(3-pyridyl))amino]carboxamide;
N-(2-{2-[(dimethylamino)carbonylamino]ethyl}(5-1,2,3,4-tetrahydroisoquinolyl))[(6-methyl(3-pyridyl))amino]carboxamide;
methyl 4-[3-(2-fluoro-3-{[(6-methyl(3-pyridyl))amino]carbonylamino}phenyl)propyl]piperazinecarboxylate;
methyl 4-(4-{[(6-methyl-3-pyridyl)amino]carbonylamino}indanyl)piperazinecarboxylate;
tert-butyl 4-[3-(2-fluoro-3-{[(6-methyl(3-pyridyl))amino]carbonylamino}phenyl)propyl]piperazinecarboxylate;
methoxy-N-methyl-N-[2-(5-{[(6-methyl(3-pyridyl))amino]carbonylamino}(2-1,2,3,4-tetrahydroisoquinolyl))ethyl]carboxamide;
N-(2-{2-[(ethylsulfonyl)methylamino]ethyl}(5-1,2,3,4-tetrahydroisoquinolyl))[(6-methyl(3-pyridyl))amino]carboxamide;
N-[2-(2-{[(dimethylamino)sulfonyl]methylamino}ethyl)(5-1,2,3,4-tetrahydroisoquinolyl)][(6-methyl(3-pyridyl))amino]carboxamide;
(dimethylamino)-N-methyl-N-[2-(5-{[(6-methyl(3-pyridyl))amino]carbonylamino}(2-1,2,3,4-tetrahydroisoquinolyl)) ethyl]carboxamide;
N-methyl-N-[2-(5-{[(6-methyl(3-pyridyl))amino]carbonylamino}(2-1,2,3,4-tetrahydroisoquinolyl))ethyl]acetamide;
[(6-methyl(3-pyridyl))amino]-N-(2-{3-[(phenylmethoxy)carbonylamino]propyl}(5-1,2,3,4-tetrahydroisoquinolyl))carboxamide;
N-{2-[2-(diethylamino)ethyl](5-1,2,3,4-tetrahydroisoquinolyl)}[(6-methyl(3-pyridyl))amino]carboxamide;
N-[2-(3-{[(dimethylamino)sulfonyl]amino}propyl)(5-1,2,3,4-tetrahydro isoquinolyl)][(6-methyl(3-pyridyl))amino]carboxamide;
N-(2-{3-[(ethylsulfonyl)amino]propyl}(5-1,2,3,4-tetrahydroisoquinolyl))[(6-methyl(3-pyridyl))amino]carboxamide;
methyl 4-[(2-hydroxy-3-{[(6-methyl(3-pyridyl))amino]carbonylamino}phenyl)methyl]piperazinecarboxylate;
N-(3-{[4-(ethylsulfonyl)piperazinyl]methyl}-2-hydroxyphenyl)[(6-methyl(3-pyridyl))amino]carboxamide;
N-(3-{2-[4-(N,N-dimethylcarbamoyl)piperazinyl]ethyl}phenyl)[(6-methyl(3-pyridyl))amino]carboxamide;
N-[3-(2-{4-[(dimethylamino)sulfonyl]piperazinyl}ethyl)phenyl][(6-methyl(3-pyridyl))amino]carboxamide;
[(6-methyl(3-pyridyl))amino]-N-(3-{2-[4-(methylsulfonyl)piperazinyl]ethyl}phenyl)carboxamide;
ethyl 4-[(2-hydroxy-3-{[(6-methyl(3-pyridyl))amino]carbonylamino}phenyl)methyl]piperazinecarboxylate;
N-(2-hydroxy-3-{[4-(methylsulfonyl)piperazinyl]methyl}phenyl)[(6-methyl(3-pyridyl))amino]carboxamide;
N-{3-[2-(4-acetylpiperazinyl)ethyl]phenyl}[(6-methyl(3-pyridyl))amino]carboxamide;
N-[2-fluoro-3-(3-piperazinylpropyl)phenyl][(6-methyl(3-pyridyl))amino]carboxamide;
N-(3-{3-[4-(ethylsulfonyl)piperazinyl]propyl}-2-fluorophenyl)[(6-methyl(3-pyridyl))amino]carboxamide;
N-{3-[3-(4-acetylpiperazinyl)propyl]-2-fluorophenyl}[(6-methyl(3-pyridyl))amino]carboxamide;
ethyl 4-[3-(2-fluoro-3-{[(6-methyl(3-pyridyl))amino]carbonylamino}phenyl)propyl]piperazinecarboxylate;
methyl 4-[(3-{[(1-hydroxy-6-methyl-3-pyridyl)amino]carbonylamino}phenyl)methyl]piperazinecarboxylate;
methyl 4-[(2-fluoro-3-{[(1-hydroxy-6-methyl(3-pyridyl))amino]carbonylamino}phenyl)methyl]piperazinecarboxylate;
phenylmethyl(2S,6R)-4-[(2-fluoro-3-{[(6-methyl(3-pyridyl))amino]carbonylamino}phenyl)methyl]-2,6-dimethylpiperazinecarboxylate;
N-{3-[((3S,5R)-4-acetyl-3,5-dimethylpiperazinyl)methyl]-2-fluorophenyl}[(6-methyl(3-pyridyl))amino]carboxamide;
tert-butyl 4-[(2-fluoro-3-{[N-(6-methyl(3-pyridyl))carbamoyl]amino}phenyl)methyl]piperazinecarboxylate;
ethyl 4-[(2-fluoro-3-{[N-(6-methyl(3-pyridyl))carbamoyl]amino}phenyl)methyl]piperazinecarboxylate;
({3-[(4-acetylpiperazinyl)methyl]-2-fluorophenyl}amino)-N-(6-methyl(3-pyridyl))carboxamide;
{[3-({4-[(dimethylamino)sulfonyl]piperazinyl}methyl)-2-fluorophenyl]amino}-N-(6-methyl(3-pyridyl))carboxamide;
[(3-{[4-(N,N-dimethylcarbamoyl)piperazinyl]methyl}-2-fluorophenyl)amino]-N-(6-methyl(3-pyridyl))carboxamide;
[(3-{[4-(ethylsulfonyl)piperazinyl]methyl}-2-fluorophenyl)amino]-N-(6-methyl(3-pyridyl))carboxamide;
[(2-fluoro-3-{[4-(methylsulfonyl)piperazinyl]methyl}phenyl)amino]-N-(6-methyl(3-pyridyl))carboxamide;

methyl(2S,6R)-4-[(2-fluoro-3-{[(6-methyl(3-pyridyl))amino]carbonylamino}phenyl)methyl]-2,6-dimethylpiperazinecarboxylate;
N-{3-[((3S,5R)-3,5-dimethylpiperazinyl)methyl]-2-fluorophenyl}[(6-methyl(3-pyridyl))amino]carboxamide;
methyl 4-[(2-fluoro-3-{[(5-methylisoxazol-3-yl)amino]carbonylamino}phenyl)methyl]piperazinecarboxylate;
methyl 4-[(2-fluoro-3-{[(4-fluorophenyl)amino]carbonylamino}phenyl)methyl]piperazinecarboxylate;
tert-butyl 4-(4-{[(6-methyl-3-pyridyl)amino]carbonylamino} indanyl)piperazinecarboxylate;
methyl 4-[(3-{[N-(6-cyano(3-pyridyl))carbamoyl]amino}-2-fluorophenyl)methyl]piperazinecarboxylate;
methyl 4-[(3-[N-(6-acetyl(3-pyridyl))carbamoyl]amino-2-fluorophenyl)methyl]piperazinecarboxylate;
methyl 4-{[2-fluoro-3-({N-[6-(trifluoromethyl)(3-pyridyl)]carbamoyl}amino)phenyl]methyl}piperazinecarboxylate;
methyl 4-({2-fluoro-3-[(N-(4-pyridyl)carbamoyl)amino]phenyl}methyl)piperazinecarboxylate;
[(3-{[4-(azetidinylsulfonyl)piperazinyl]methyl}-2-fluorophenyl)amino]-N-(6-methyl(3-pyridyl))carboxamide;
[(6-methyl(3-pyridyl))amino]-N-(1-piperazinylindan-4-yl)carboxamide;
N-[1-(4-acetylpiperazinyl)indan-4-yl][(6-methyl(3-pyridyl))amino]carboxamide;
N-{1-[4-(N,N-dimethylcarbamoyl)piperazinyl] indan-4-yl}[(6-methyl(3-pyridyl))amino]carboxamide;
[(6-methyl(3-pyridyl))amino]-N-{1-[4-(methylsulfonyl)piperazinyl]indan-4-yl}carboxamide;
tert-butyl 4-[(4-{[(6-methyl-3-pyridyl)amino]carbonylamino} indan-2-yl)methyl]piperazinecarboxylate;
methyl 4-[(4-{[(6-methyl-3-pyridyl)amino]carbonylamino}indan-2-yl)methyl]piperazinecarboxylate;
ethyl 4-[(4-{[(6-methyl-3-pyridyl)amino]carbonylamino}indan-2-yl)methyl]piperazinecarboxylate;
N-{2-[(4-acetylpiperazinyl)methyl]indan-4-yl}[(6-methyl(3-pyridyl))amino]carboxamide;
N-(2-{[4-(N,N-dimethylcarbamoyl)piperazinyl]methyl}indan-4-yl)[(6-methyl(3-pyridyl))amino]carboxamide;
N-(2-{[4-(ethylsulfonyl)piperazinyl]methyl} indan-4-yl)[(6-methyl(3-pyridyl))amino]carboxamide;
N-[2-({4-[(dimethylamino)sulfonyl]piperazinyl}methyl)indan-4-yl][(6-methyl(3-pyridyl))amino]carboxamide;
tert-butyl(5S,3R)-4-[(2-fluoro-3-{[N-(6-methyl(3-pyridyl))carbamoyl]amino}phenyl)methyl]-3,5-dimethylpiperazinecarboxylate;
methyl(5S,3R)-4-[(2-fluoro-3-{[N-(6-methyl(3-pyridyl))carbamoyl]amino}phenyl)methyl]-3,5-dimethylpiperazinecarboxylate;
({3-[((6S,2R)-4-acetyl-2,6-dimethylpiperazinyl)methyl]-2-fluorophenyl}amino)-N-(6-methyl(3-pyridyl))carboxamide;
{(5S,3R)-4-[(2-fluoro-3-{[N-(6-methyl(3-pyridyl))carbamoyl]amino}phenyl)methyl]-3,5-dimethylpiperazinyl}-N,N-dimethylcarboxamide;
[(3-{[((6S,2R)-4-(ethylsulfonyl)-2,6-dimethylpiperazinyl]methyl}-2-fluorophenyl)amino]-N-(6-methyl(3-pyridyl))carboxamide;
{[3-({(6S,2R)-4-[(dimethylamino)sulfonyl]-2,6-dimethylpiperazinyl}methyl)-2-fluorophenyl]amino}-N-(6-methyl(3-pyridyl))carboxamide;
N-[2-fluoro-3-(1,2,4-triazolo[3,4-c]piperazin-7-ylmethyl)phenyl][(6-methyl(3-pyridyl))amino]carboxamide;
2-fluoro-3-{[(6-methyl(3-pyridyl))amino]carbonylamino}benzoic acid;
N-{2-fluoro-3-[(3-methyl(1,2,4-triazolo[3,4-c]piperazin-7-yl))methyl]phenyl}[(6-methyl(3-pyridyl))amino]carboxamide;
N-{3-[(3-ethyl(1,2,4-triazolo[3,4-c]piperazin-7-yl))methyl]-2-fluorophenyl}[(6-methyl(3-pyridyl))amino]carboxamide;
N-(2-fluoro-3-{[4-(methylsulfonyl)piperazinyl]methyl}phenyl)(4-pyridylamino)carboxamide;
N-(3-{[4-(ethylsulfonyl)piperazinyl]methyl}-2-fluorophenyl)(4-pyridylamino)carboxamide;
ethyl 4-(2-fluoro-3-(3-(pyridin-3-yl)ureido)$_b$ enzyl)piperazine-1-carboxylate;
1-(3-((4-acetylpiperazin-1-yl)methyl)-2-fluorophenyl)-3-(pyridin-3-yl)urea;
methyl 4-(2-fluoro-3-(3-(pyridin-3-yl)ureido)benzyl)piperazine-1-carboxylate;
methyl 4-(2-fluoro-3-(3-(6-fluoropyridin-3-yl)ureido)benzyl)piperazine-1-carboxylate;
methyl 4-(2-fluoro-3-(3-(6-methylpyridin-3-yl)ureido)benzyl)piperazine-1-carboxylate;
(3R,5S)-tert-butyl 4-(2-fluoro-3-(3-(pyridin-3-yl)ureido)benzyl)-3,5-dimethylpiperazine-1-carboxylate;
1-(3-(((2R,6S)-4-acetyl-2,6-dimethylpiperazin-1-yl)methyl)-2-fluorophenyl)-3-(pyridin-3-yl)urea;
(3R,5S)-4-(2-fluoro-3-(3-(pyridin-3-yl)ureido)benzyl)-N,N,3,5-tetramethylpiperazine-1-carboxamide;
(2S,6R)-benzyl 4-(2-fluoro-3-(3-(pyridin-3-yl)ureido)benzyl)-2,6-dimethylpiperazine-1-carboxylate;
1-(3-(((3S,5R)-3,5-dimethylpiperazin-1-yl)methyl)-2-fluorophenyl)-3-(pyridin-3-yl)urea;
tert-butyl 4-(2-fluoro-3-(3-(pyridin-3-yl)ureido)benzyl)piperazine-1-carboxylate;
(3R,5S)-methyl 4-(2-fluoro-3-(3-(pyridin-3-yl)ureido)benzyl)-3,5-dimethylpiperazine-1-carboxylate;
methyl 4-(2-fluoro-3-(3-pyridin-3-ylureido)benzyl)piperazine-1-carboxylate
(2S,6R)-methyl 4-(2-fluoro-3-(3-(pyridin-3-yl)ureido)benzyl)-2,6-dimethylpiperazine-1-carboxylate;
4-(2-fluoro-3-(3-(pyridin-3-yl)ureido)benzyl)-N,N-dimethylpiperazine-1-carboxamide;
4-(2-fluoro-3-(3-(pyridin-3-yl)ureido)benzyl)-N,N-dimethylpiperazine-1-sulfonamide;
1-(3((4-(ethylsulfonyl)piperazin-1-yl)methyl)-2-fluorophenyl)-3-(pyridin-3-yl)urea;
1-(3-((4-(methylsulfonyl)piperazin-1-yl)methyl)phenyl)-3-(pyridin-3-yl)urea;
1-(3-((4-(azetidin-1-ylsulfonyl)piperazin-1-yl)methyl)-2-fluorophenyl)-3-(pyridin-3-yl)urea;
1-(3-(((2R,6S)-4-(ethylsulfonyl)-2,6-dimethylpiperazin-1-yl)methyl)-2-fluorophenyl)-3-(pyridin-3-yl)urea;
(3R,5S)-4-(2-fluoro-3-(3-(pyridin-3-yl)ureido)benzyl)-N,N,3,5-tetramethylpiperazine-1-sulfonamide;
methyl 4-(2-fluoro-3-(3-(isoxazol-3-yl)ureido)benzyl)piperazine-1-carboxylate;
ethyl 4-(4-fluoro-3-(3-(pyridin-3-yl)ureido)benzyl)piperazine-1-carboxylate;
methyl 4-(2-fluoro-3-(3-(pyridin-3-yl)ureido)benzyl)piperazine-1-carboxylate;
methyl 4-(2,6-difluoro-3-(3-(pyridin-3-yl)ureido)benzyl)piperazine-1-carboxylate;
methyl 4-(3,4-difluoro-5-(3-(pyridin-3-yl)ureido)benzyl)piperazine-1-carboxylate;
(S)-ethyl 4-(1-(2-fluoro-3-(3-(pyridin-3-yl)ureido)phenyl)ethyl)piperazine-1-carboxylate;
(S)-methyl 4-(1-(2-fluoro-3-(3-(6-pyridin-3-yl)ureido)phenyl)ethyl)piperazine-1-carboxylate;

methyl 4-(2,5-difluoro-3-(3-(pyridin-3-yl)ureido)benzyl)piperazine-1-carboxylate;
methyl 4-(3-(2-fluoro-3-(3-(pyridin-3-yl)ureido)phenyl)propyl)piperazine-1-carboxylate;
ethyl 4-(3-(2-fluoro-3-(3-(pyridin-3-yl)ureido)phenyl)propyl)piperazine-1-carboxylate;
methyl 4-(3-(3-fluoro-5-(3-(pyridin-3-yl)ureido)phenyl)propyl)piperazine-1-carboxylate;
Ethanesulfonic acid {3-fluoro-5-[3-(6-methyl-pyridin-3-yl)-ureido]-benzyl}-methyl-amide;
Ethanesulfonic acid {3-fluoro-5-[3-(pyridin-3-yl)-ureido]-benzyl}-methyl-amide;
1-[3-(4-Acetyl-piperazin-1-ylmethyl)-5-fluoro-phenyl]-3-(pyridin-3-yl)-urea;
1-[3-Fluoro-5-(4-methanesulfonyl-piperazin-1-ylmethyl)-phenyl]-3-(pyridin-3-yl)-urea;
1-{3-Fluoro-5-[4-(2-methoxy-acetyl)-piperazin-1-ylmethyl]-phenyl}-3-(pyridin-3-yl)-urea;
1-{3-Fluoro-5-[4-(propane-2-sulfonyl)-piperazin-1-ylmethyl]-phenyl}-3-(pyridin-3-yl)-urea;
1-{3-Fluoro-5-[4-(propane-1-sulfonyl)-piperazin-1-ylmethyl]-phenyl}-3-(pyridin-3-yl)-urea;
1-[3-(4-Ethanesulfonyl-piperazin-1-ylmethyl)-5-fluoro-phenyl]-3-(2-methyl-pyrimidin-5-yl)-urea;
4-{3-Fluoro-5-[3-(2-methyl-pyrimidin-5-yl)-ureido]-benzyl}-piperazine-1-sulfonic acid dimethylamide;
4-{3-Fluoro-5-[3-(pyrimidin-5-yl)-ureido]-benzyl}-piperazine-1-carboxylic acid methyl ester;
(S)—N-(1-(3-fluoro-5-(3-(6-methylpyridin-3-yl)ureido)benzyl)piperidin-3-yl)-N-methyl-(N',N'-dimethylamino)sulfonamide;
(S)—N-(1-(3-fluoro-5-(3-pyridin-3-ylureido)benzyl)piperidin-3-yl)-N-methyl-(N',N'-dimethylamino)sulfonamide;
(E)-N'-cyano-4-(3-fluoro-5-(3-pyridin-3-ylureido)benzyl)-N,N-dimethylpiperazine-1-carboximidamide; or
(S)-1-(3-(1-(4-acetylpiperazin-1-yl)ethyl)phenyl)-3-(6-methylpyridin-3-yl)urea.

In certain embodiments, the compound of Formula I is chosen from
methyl 4-[(3-fluoro-5-{[(6-methyl(3-pyridyl))aminocarbonylamino}phenyl)methyl]piperazinecarboxylate;
N-(3-{[4-(ethylsulfonyl)piperazinyl]methyl}-5-fluorophenyl)[(6-methyl(3-pyridyl))amino]carboxamide;
N-[5-({4-[(dimethylamino)sulfonyl]piperazinyl}methyl)-2-fluorophenyl][(6-methyl(3-pyridyl))amino]carboxamide;
methyl 4-[(4-fluoro-3-{[(6-methyl(3-pyridyl))aminocarbonylamino}phenyl)methyl]piperazinecarboxylate;
methyl 4-[(3-{[(6-methyl-3-pyridyl)aminocarbonylamino}phenyl)methyl]piperazinecarboxylate;
N-[3-({-4-[(dimethylamino)sulfonyl]piperazinyl}methyl)phenyl][(6-methyl(3-pyridyl))amino]carboxamide;
methyl(2S)-4-[(5-fluoro-3-{[(6-methyl(3-pyridyl))aminocarbonylamino}phenyl)methyl]-2-(methoxymethyl)piperazinecarboxylate;
N-[5-fluoro-3-({4-[methyl(methylsulfonyl)amino]piperidyl}methyl)phenyl][(4-fluorophenyl)amino]carboxamide;
ethyl 4-[(4-fluoro-3-{[(6-methyl(3-pyridyl))aminocarbonylamino}phenyl)methyl]piperazinecarboxylate;
methyl(2S)-4-[(4-fluoro-3-{[(6-methyl(3-pyridyl))aminocarbonylamino}phenyl)methyl]-2-(methoxymethyl)piperazinecarboxylate;
methyl 4-[(2-fluoro-3-{[(6-methyl(3-pyridyl))aminocarbonylamino}phenyl)methyl]piperazinecarboxylate;
[(6-cyano(3-pyridyl))amino]-N-(3-{[4-(ethylsulfonyl)piperazinyl]methyl}-5-fluorophenyl)carboxamide;
methyl 4-[(2,6-difluoro-3-{[(6-methyl(3-pyridyl))aminocarbonylamino}phenyl)methyl]piperazinecarboxylate;
methyl 4-[(1S)-1-(5-fluoro-3-{[(6-methyl(3-pyridyl))amino]carbonylamino}phenyl)ethyl]piperazinecarboxylate;
ethyl 4-[(1S)-1-(5-fluoro-3-{[(6-methyl(3-pyridyl))aminocarbonylamino}phenyl)ethyl]piperazinecarboxylate;
methyl 4-[(3,4-difluoro-5-{[(6-methyl(3-pyridyl))aminocarbonylamino}phenyl)methyl]piperazinecarboxylate;
methyl 4-[(1S)-1-(3-{[(6-methyl(3-pyridyl))aminocarbonylamino}phenyl)ethyl]piperazinecarboxylate;
methyl 4-[(1S)-1-(2-fluoro-3-{[(6-methyl(3-pyridyl))amino]carbonylamino}phenyl)ethyl]piperazinecarboxylate;
ethyl 4-[(1S)-1-(2-fluoro-3-[{(6-methyl(3-pyridyl))aminocarbonylamino}phenyl)ethyl]piperazinecarboxylate;
methyl 4-[(2,4-difluoro-3-{[(6-methyl(3-Pyridyl))aminocarbonylamino}phenyl)methyl]piperazinecarboxylate;
methyl 4-[(2,5-difluoro-3-{[(6-methyl(3-pyridyl))aminocarbonylamino}phenyl)methyl]piperazinecarboxylate;
methyl 4-[3-(2-fluoro-3-{[(6-methyl(3-pyridyl))aminocarbonylamino}phenyl)propyl]piperazinecarboxylate;
ethyl 4-[3-(2-fluoro-3-{[(6-methyl(3-pyridyl))aminocarbonylamino}phenyl)propyl]piperazinecarboxylate;
ethyl 4-[(2-fluoro-3-{[N-(6-methyl(3-pyridyl))carbamoyl]amino}phenyl)methyl]piperazinecarboxylate;
{[3-({4-[(dimethylamino)sulfonyl]piperazinyl}methyl)-2-fluorophenyl]amino}-N-(6-methyl(3-pyridyl))carboxamide;
[(3-{[4-(N,N-dimethylcarbamoyl)piperazinyl]methyl}-2-fluorophenyl)amino]-N-(6-methyl(3-pyridyl))carboxamide;
[(3-{[4-(ethylsulfonyl)piperazinyl]methyl}-2-fluorophenyl)amino]-N-(6-methyl(3-pyridyl))carboxamide;
methyl(2S,6R)-4-[(2-fluoro-3-{[(6-methyl(3-pyridyl))amino]carbonylamino}phenyl)methyl]-2,6-dimethylpiperazinecarboxylate;
methyl 4-[(2-fluoro-3-{[(5-methylisoxazol-3-yl)amino]carbonylamino}phenyl)methyl]piperazinecarboxylate;
methyl 4-[(2-fluoro-3-[(4-fluorophenyl)amino]carbonylamino phenyl)methyl]piperazinecarboxylate;
methyl 4-[(3-{[N-(6-cyano(3-pyridyl))carbamoyl]amino}-2-fluorophenyl)methyl]piperazinecarboxylate;
methyl 4-[(3-{[N-(6-acetyl(3-pyridyl))carbamoyl]amino}-2-fluorophenyl)methyl]piperazinecarboxylate;
methyl 4-{[2-fluoro-3-({N-[6-(trifluoromethyl)(3-pyridyl)]carbamoyl}amino)phenyl]methyl}piperazinecarboxylate;
methyl 4-({2-fluoro-3-[(N-(4-pyridyl)carbamoyl)amino]phenyl}methyl)piperazinecarboxylate; and
N-(2-fluoro-3-{[4-(methylsulfonyl)piperazinyl]methyl}phenyl)(4-pyridylamino)carboxamide.

The chemical entities described herein are selective for and modulate the cardiac sarcomere, and are useful to bind to and/or potentiate the activity of cardiac myosin, increasing the rate at which myosin hydrolyzes ATP. As used in this context, "modulate" means either increasing or decreasing myosin activity, whereas "potentiate" means to increase activity. It has also been determined in testing representative compounds of the invention, that their administration can also increase the contractile force in cardiac muscle fiber.

The chemical entities, pharmaceutical compositions and methods of the invention are used to treat heart disease, including but not limited to: acute (or decompensated) congestive heart failure, and chronic congestive heart failure; particularly diseases associated with systolic heart dysfunction. Additional therapeutic utilities include administration to stabilize cardiac function in patients awaiting a heart transplant, and to assist a stopped or slowed heart in resuming normal function following use of a bypass pump.

ATP hydrolysis is employed by myosin in the sarcomere to produce force. Therefore, an increase in ATP hydrolysis would correspond to an increase in the force or velocity of muscle contraction. In the presence of actin, myosin ATPase activity is stimulated >100 fold. Thus, ATP hydrolysis not only measures myosin enzymatic activity but also its interaction with the actin filament. A compound that modulates the cardiac sarcomere can be identified by an increase or decrease in the rate of ATP hydrolysis by myosin, in certain embodiments, exhibiting a 1.4 fold increase at concentrations less than 10 µM (such as less than 1 µM). Assays for such activity can employ myosin from a human source, although myosin from other organisms is usually used. Systems that model the regulatory role of calcium in myosin binding to the decorated thin filament are also used.

Alternatively, a biochemically functional sarcomere preparation can be used to determine in vitro ATPase activity, for example, as described in U.S. Ser. No. 09/539,164, filed Mar. 29, 2000. The functional biochemical behavior of the sarcomere, including calcium sensitivity of ATPase hydrolysis, can be reconstituted by combining its purified individual components (particularly including its regulatory components and myosin). Another functional preparation is the in vitro motility assay. It can be performed by adding test compound to a myosin-bound slide and observing the velocity of actin filaments sliding over the myosin covered glass surface (Kron S J. (1991) Methods Enzymol. 196:399-416).

The in vitro rate of ATP hydrolysis correlates to myosin potentiating activity, which can be determined by monitoring the production of either ADP or phosphate, for example as described in Ser. No. 09/314,464, filed May 18, 1999. ADP production can also be monitored by coupling the ADP production to NADH oxidation (using the enzymes pyruvate kinase and lactate dehydrogenase) and monitoring the NADH level either by absorbance or fluorescence (Greengard, P., *Nature* 178 (Part 4534): 632-634 (1956); *Mol Pharmacol* 1970 Jan; 6(1):31-40). Phosphate production can be monitored using purine nucleoside phosphorylase to couple phosphate production to the cleavage of a purine analog, which results in either a change in absorbance (*Prot Natl Acad Sci USA* 1992 Jun. 1; 89(11):4884-7) or fluorescence (*Biochem J* 1990 Mar. 1; 266(2):611-4). While a single measurement can be employed, generally multiple measurements of the same sample at different times will be taken to determine the absolute rate of the protein activity; such measurements have higher specificity particularly in the presence of test compounds that have similar absorbance or fluorescence properties with those of the enzymatic readout.

Test compounds can be assayed in a highly parallel fashion using multiwell plates by placing the compounds either individually in wells or testing them in mixtures. Assay components including the target protein complex, coupling enzymes and substrates, and ATP can then be added to the wells and the absorbance or fluorescence of each well of the plate can be measured with a plate reader.

A method uses a 384 well plate format and a 25 µL reaction volume. A pyruvate kinase/lactate dehydrogenase coupled enzyme system (Huang T G and Hackney DD. (1994) J Biol Chem 269(23):16493-16501) is used to measure the rate of ATP hydrolysis in each well. As will be appreciated by those in the art, the assay components are added in buffers and reagents. Since the methods outlined herein allow kinetic measurements, incubation periods are optimized to give adequate detection signals over the background. The assay is done in real time giving the kinetics of ATP hydrolysis, which increases the signal to noise ratio of the assay.

Modulation of cardiac muscle fiber ATPase and/or contractile force can also be measured using detergent permeabilized cardiac fibers (also referred to as skinned cardiac fibers) or myofibrils (subcellular muscle fragments), for example, as described by Haikala H, et al (1995) J Cardiovasc Pharmacol 25(5):794-801. Skinned cardiac fibers retain their intrinsic sarcomeric organization, but do not retain all aspects of cellular calcium cycling, this model offers two advantages: first, the cellular membrane is not a barrier to compound penetration, and second, calcium concentration is controlled. Therefore, any increase in ATPase or contractile force is a direct measure of the test compound's effect on sarcomeric proteins. ATPase measurements are made using methods as described above. Tension measurements are made by mounting one end of the muscle fiber to a stationary post and the other end to a transducer that can measure force. After stretching the fiber to remove slack, the force transducer records increased tension as the fiber begins to contract. This measurement is called the isometric tension, since the fiber is not allowed to shorten. Activation of the penneabilized muscle fiber is accomplished by placing it in a buffered calcium solution, followed by addition of test compound or control. When tested in this manner, chemical entities described herein caused an increase in force at calcium concentrations associated with physiologic contractile activity, but very little augmentation of force in relaxing buffer at low calcium concentrations or in the absence of calcium (the EGTA data point).

Selectivity for the cardiac sarcomere and cardiac myosin can be determined by substituting non-cardiac sarcomere components and myosin in one or more of the above-described assays and comparing the results obtained against those obtained using the cardiac equivalents.

A chemical entity's ability to increase observed ATPase rate in an in vitro reconstituted sarcomere assay or myofibril could result from the increased turnover rate of S1-myosin or, alternatively, increased sensitivity of a decorated actin filament to $Ca^{++}$-activation. To distinguish between these two possible modes of action, the effect of the chemical entity on ATPase activity of S1 with undecorated actin filaments is initially measured. If an increase of activity is observed, the chemical entity's effect on the Ca-responsive regulatory apparatus could be disproved. A second, more sensitive assay, can be employed to identify chemical entities whose activating effect on S1-myosin is enhanced in the presence of a decorated actin (compared to pure actin filaments). In this second assay activities of cardiac-S1 and skeletal-S1 on cardiac and skeletal regulated actin filaments (in all 4 permutations) are compared.

Initial evaluation of in vivo activity can be determined in cellular models of myocyte contractility, e.g., as described by Popping S, et al ((1996) Am. J. Physiol. 271: H357-H364) and Wolska B M, et al ((1996) Am. J. Physiol. 39:H24-H32). One advantage of the myocyte model is that the component systems that result in changes in contractility can be isolated and the major site(s) of action determined. Chemical entities with cellular activity (for example, selecting chemical entities having the following profile: >120% increase in fractional shortening over basal at 2 µM, or result in changes in diastolic length (<5% change)) can then be assessed in whole organ models, such as such as the Isolated Heart (Langendorffl) model of cardiac function, in vivo using echocardiography or invasive hemodynamic measures, and in animal-based heart failure models, such as the Rat Left Coronary Artery Occlusion model. Ultimately, activity for treating heart disease is demonstrated in blinded, placebo-controlled, human clinical trials.

The chemical entities described herein are administered at a therapeutically effective dosage, e.g., a dosage sufficient to provide treatment for the disease states previously described. While human dosage levels have yet to be optimized for the chemical entities described herein, generally, a daily dose is from about 0.05 to 100 mg/kg of body weight; in certain embodiments, about 0.10 to 10.0 mg/kg of body weight, and in certain embodiments, about 0.15 to 1.0 mg/kg of body weight. Thus, for administration to a 70 kg person, in certain embodiments, the dosage range would be about 3.5 to 7000 mg per day; in certain embodiments, about 7.0 to 700.0 mg per day, and in certain embodiments, about 10.0 to 100.0 mg per day. The amount of chemical entity administered will, of course, be dependent on the subject and disease state being treated, the severity of the affliction, the manner and schedule of administration and the judgment of the prescribing physician; for example, a likely dose range for oral administration would be about 70 to 700 mg per day, whereas for intravenous administration a likely dose range would be about 70 to 700 mg per day depending on compound pharmacokinetics.

Administration of the chemical entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. Oral and parenteral administration are customary in treating the indications that are the subject of the present invention.

Pharmaceutically acceptable compositions include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In addition, the chemical entities described herein can be co-administered with, and the pharmaceutical compositions can include, other medicinal agents, pharmaceutical agents, adjuvants, and the like. Suitable additional active agents include, for example: therapies that retard the progression of heart failure by down-regulating neurohormonal stimulation of the heart and attempt to prevent cardiac remodeling (e.g., ACE inhibitors or β-blockers); therapies that improve cardiac function by stimulating cardiac contractility (e.g., positive inotropic agents, such as the (3-adrenergic agonist dobutamine or the phosphodiesterase inhibitor milrinone); and therapies that reduce cardiac preload (e.g., diuretics, such as furosemide). Other suitable additional active agents include vasodilators, digitoxin, anticoagulants, mineralocorticoid antagonists, angiotensin receptor blockers, nitroglycerin, other inotropes, and any other therapy used in the treatment of heart failure.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise 0.2-2% of the active agent in solution.

Pharmaceutical compositions of the chemical entities described herein may also be administered to the respiratory tract as an aerosol or solution for a nebulizer, or as a microtine powder for insufflation, alone or in combination with an inert carrier such as lactose. In such a case, the particles of the pharmaceutical composition have diameters of less than 50 microns, in certain embodiments, less than 10 microns.

Generally, to employ the chemical entities described herein in a method of screening for myosin binding, myosin is bound to a support and a compound of the invention is added to the assay. Alternatively, the chemical entities described herein can be bound to the support and the myosin added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like. See, e.g., U.S. Pat. No. 6,495,337, incorporated herein by reference.

The following examples serve to more fully describe the manner of using the above-described invention. It is understood that these examples in no way serve to limit the true scope of this invention, but rather are presented for illustrative purposes. All references cited herein are incorporated by reference in their entirety.

EXAMPLE 1

Step 1

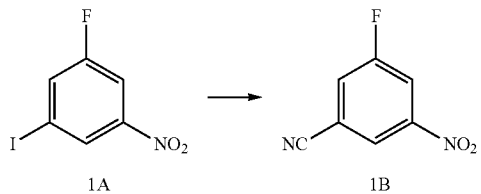 [SMILES: O=[N+]([O-])c1cc(F)cc(I)c1 ; N#Cc1cc(F)cc([N+](=O)[O-])c1]

To a solution of 1.0 eq 1A in dry DMF (0.37 M) was added $Zn(CN)_2$ (0.92 eq) and $Pd(PPh_3)_4$ (0.058 eq). The reaction mixture was purged with nitrogen and heated to 80° C. overnight. An additional 0.023 eq of $Pd(PPh_3)_4$ was then added and the reaction was heated for another 6 hrs. The reaction mixture was then cooled to RT, diluted with 15 volumes of EtOAc (based on 1A) and the organic layer was washed 3 times with water and once with brine. The organic layer was dried over sodium sulfate, filtered and concentrated. Purification by chromatography over silica gel using 10% $Et_2O$/hexane as the eluant provided 1B as a solid (90%).

EXAMPLE 1

Step 2

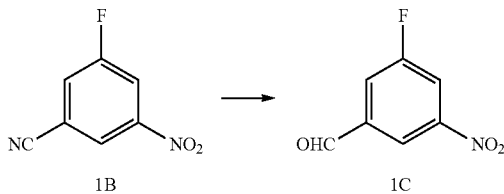 [SMILES: N#Cc1cc(F)cc([N+](=O)[O-])c1 ; O=Cc1cc(F)cc([N+](=O)[O-])c1]

To solution of 1.0 eq 1B in dry $Et_2O$ (0.06 M) at 0° C. was added dropwise a solution of diisobutyllithiumaluminum hydride (1.1 eq, 1.0 M in hexanes) by syringe. The resulting solution was kept at 0° C. overnight. The reaction mixture was added to a mixture of ice and glacial acetic acid. The reaction mixture was then diluted with ethyl acetate, and the aqueous layer was extracted with ethyl acetate two additional times. The combined organic layers were washed twice with saturated sodium bicarbonate, and once with brine. The organic layers were then dried over sodium sulfate, filtered and concentrated in vacuo. Purification over silica gel using 10% EtOAc/hexanes as the eluant afforded a yellow solid (100%) as an 80:20 mixture of 1C:1B.

EXAMPLE 1

Step 3

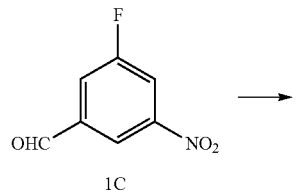

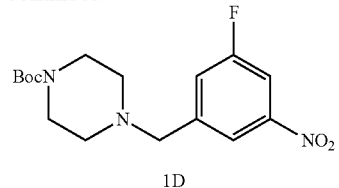

To cooled (0° C.) slurry of an 80:20 mixture of 1C:1B (1.0 eq) and boc-piperazine (about 2 eq) in a mixture of HOAc and DCM (4.8 M boc-piperazine in 1:1.4 v/v HOAc/DCM) was added sodium triacetoxyborohydride as a solid over about 5 minutes. The reaction was allowed to warm to RT and stirred for two hours. The reaction mixture was quenched with saturated sodium bicarbonate and diluted with ethyl acetate. The layers were separated and the aqueous layer was washed three times with ethyl acetate. The organic layers were combined and washed with brine, dried over sodium sulfate, and concentrated in vacuo. Purification by chromatography over silica gel using 50% ethyl acetate/hexanes as the eluant provided 1D (67.7%) as a yellow oil.

EXAMPLE 1

Step 4

A mixture of 1.0 eq of 1D, and a catalytic amount of 10% Pd/C (approximately 10 wt/wt %) in MeOH (about 0.6 M 1D in MeOH) was stirred over an atmosphere of 50 psi H2 for 45 min. After replacement of the $H_2$ atmosphere with $N_2$, the reaction mixture was filtered through diatomaceous earth and the diatomaceous earth washed with MeOH. Concentration of the MeOH resulted in the isolation of 1E.

EXAMPLE 1

Step 5

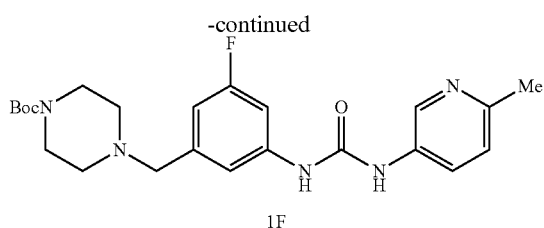

1F

To a solution of aniline 1E (1.0 eq) in dry DCM (about 0.1 M 1E in DCM) at RT under N2 atmosphere was added the 2-methyl-5-isocyanatopyridine (slight excess, about 1.2 eq) by syringe. The mixture was stirred for 1 hour. To the reaction mixture was added sequentially saturated aqueous sodium bicarbonate and ethyl acetate. The layers were separated and the organic layer was washed twice with sat. NaHCO$_3$ and once with brine. The organic layer was dried over sodium sulfate, filtered and concentrated in vacuo. Purification by chromatography over silica gel using 5% methanol/DCM as the eluant provided 1F.

EXAMPLE 1

Steps 6 and 7

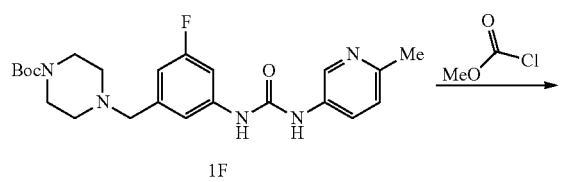

1F

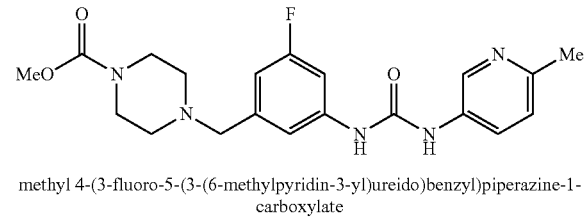

methyl 4-(3-fluoro-5-(3-(6-methylpyridin-3-yl)ureido)benzyl)piperazine-1-carboxylate

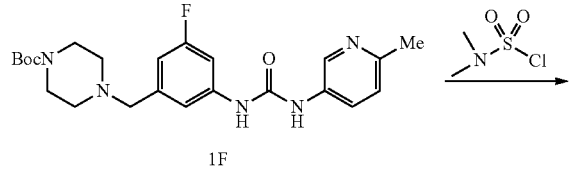

1F

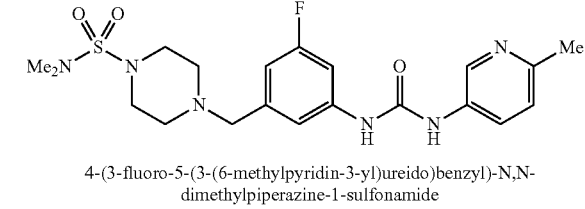

4-(3-fluoro-5-(3-(6-methylpyridin-3-yl)ureido)benzyl)-N,N-dimethylpiperazine-1-sulfonamide To a solution of 1.0 eq of 1F in CH$_2$Cl$_2$ (about 0.14 M 1F in DCM) was added approximately 200 eq of trifluoroacetic acid (TFA). The reaction mixture was stirred for 30 min and concentrated. The resultant residue was dissolved in EtOAc (about 1.6 times the volume of the reaction mixture) and washed sequentially with 3N NaOH (2 times) and brine. The organic layer was dried (NaSO4) and concentrated to provided the desired free base that was used without further purification.

To a solution of the free base above (1.0 eq) and DIPEA (1.2 eq) in dry THF (about 0.2 M free base in THF) was added methyl chloroformate (1.1 eq) by syringe and the resultant mixture stirred for 1 h. To the mixture was added aqueous sodium bicarbonate followed by ethyl acetate. The organic layer was separated and washed twice with aqueous sodium bicarbonate and once with brine. The combined aqueous layers were extracted once with ethyl acetate. The combined organic layers were dried over sodium sulfate, filtered and concentrated in vacuo. Purification by chromatography over silica gel using 5% MeOH/DCM as the eluant provided methyl 4-(3-fluoro-5-(3-(6-methylpyridin-3-yl)ureido)benzyl)-piperazine-1-carboxylate. MS 402 (M+H).

To a solution of the free base above (1.0 eq) and DIPEA (1.2 eq) in dry THF (about 0.2 M free base in THF) was added dimethylsulfamoyl chloride (1.1 eq) by syringe. After a few hours, the reaction was complete. The mixture was quenched with aqueous sodium bicarbonate, diluted with ethyl acetate, and washed twice with bicarb and once with brine. The combined aqueous layers were extracted once with ethyl acetate, and the combined organic layers were dried over sodium sulfate, filtered and concentrated in vacuo. Purification by chromatography over silica gell using 5% MeOH/DCM as the eluant provided 4-(3-fluoro-5-(3-(6-methylpyridin-3-yl)ureido)benzyl)-N,N-dimethylpiperazine-1-sulfonamide. MS 451 (M+H).

EXAMPLE 2

Step 1

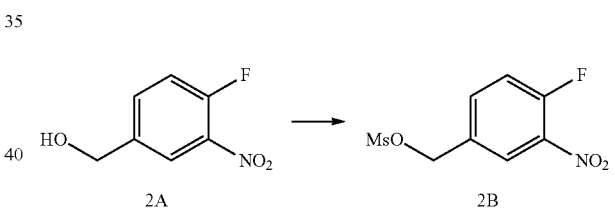

2A          2B

To 1.0 eq of (4-fluoro-3-nitro-phenyl)-methanol (2A) in THF (about 1 M 2A in THF) and (about 1.1 eq) of pyridine was added approximately 1.1 eq of methanesulfonyl chloride. The mixture was stirred overnight at room temperature then concentrated. The residue was purified using by flash chromatography over silica with 10%-50% EtOAc/hexanes as the eluant to yield of methanesulfonic acid 4-fluoro-3-nitro-benzyl ester (2B) (57%).

EXAMPLE 2

Step 2

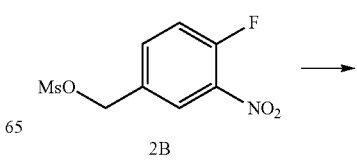

2B

-continued

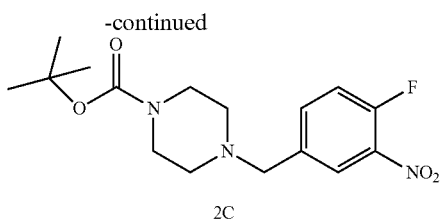

2C

To 1.0 eq of methanesulfonic acid 4-fluoro-3-nitro-benzyl ester (2B) in DMF (about 0.6 M 2B in DMF) was added about 1.05 eq of TEA and about 1.0 eq of t-butyl piperazine-1-carboxylate. The mixture was stirred for 30 min at room temperature, diluted with EtOAc, washed with NH$_4$Cl solution, dried (Na$_2$SO$_4$) and evaporated. Purification by flash chromatography over silica with 50% EtOAc/hexanes as the eluant afforded 4-(4-fluoro-3-nitro-benzyl)-piperazine-1-carboxylic acid tert-butyl ester (2C).

EXAMPLE 2

Step 3

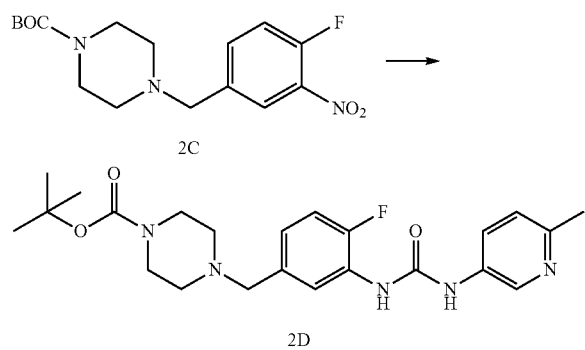

4-(4-Fluoro-3-nitro-benzyl)-piperazine-1-carboxylic acid text-butyl ester (2C, 1.0 eq) in methanol (about 0.2 M 2C in MeOH) was treated with catalytic Pd(OH)$_2$/C under hydrogen at 60 psi overnight. The mixture was filtered through diatomatious earth and concentrated to an oil. This oil was dissolved in THF and treated with approximately 1.05 eq of 6-methylpyridine-3-isocyanate. After stirring at 50° C. for 30 min the mixture was concentrated. The residue was purified by reversed phase HPLC to yield 4-{4-fluoro-3-[3-(6-methyl-pyridin-3-yl)-ureido]-benzyl}-piperazine-1-carboxylic acid tert-butyl ester (2D).

EXAMPLE 2

Steps 4 and 5

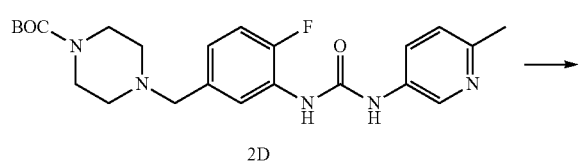

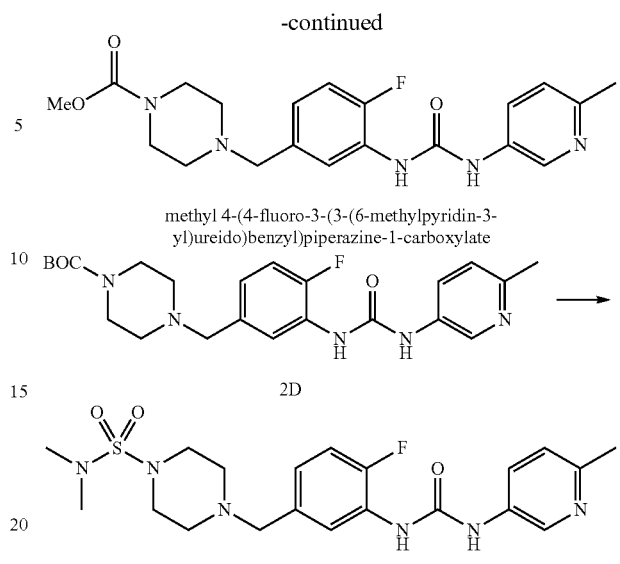

methyl 4-(4-fluoro-3-(3-(6-methylpyridin-3-yl)ureido)benzyl)piperazine-1-carboxylate 4-(4-fluoro-3-(3-(6-methylpyridin-3-yl)ureido)benzyl)-N,N-dimethylpiperazine-1-sulfonamide To 1.0 eq of 4-{4-fluoro-3-[3-(6-methyl-pyridin-3-yl)-ureido]-benzyl}-piperazine-1-carboxylic acid tert-butyl ester (2D) in MeOH (about 0.1 M 2D in MeOH) was added 2 volumes of HCl in dioxane (4 N) and the reaction mixture stirred at 50° C. for 15 min and evaporated to a solid. The solid was combined with DCM and treated with approximately 5 eq of TEA and split into 3 equal portions of reaction mixture A. One portion of the reaction mixture A was treated with 1.2 eq of methyl carbonyl chloride and stirred overnight. The resultant mixture was concentrated and purified by reversed phase HPLC to afford 4-{4-fluoro-3-[3-(6-methyl-pyridin-3-yl)-ureido]-benzyl}-piperazine-1-carboxylic acid methyl ester. MS 402 (M+H). A second portion of the reaction mixture A was treated with 1.2 eq of dimethylsulfamoyl chloride and stirred overnight. The resultant mixture was concentrated and purified by reversed phase HPLC to afford 4-{4-fluoro-3-[3-(6-methyl-pyridin-3-yl)-ureido]-benzyl}-piperazine-1-sulfonic acid dimethylamide. MS 451 (M+H).

EXAMPLE 3

Step 1

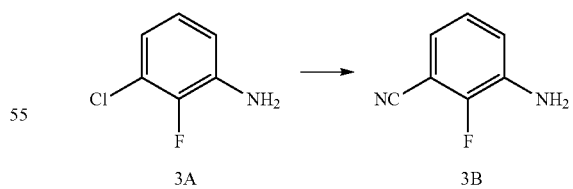

3A      3B

A round bottom flask was charged with 1 eq of 3-chloro-2-fluoroaniline (3A), 1-methyl-2-pyrrolidinone (about 1.5 M 3A in NMP), 2.2 eq of sodium cyanide, and 1.35 eq of nickel (II) bromide at RT under N2. The concentration was halved by the introduction of additional NMP under N2 and the solution was gently warmed to 200+5° C. and stirred for 4 days under N2. The reaction mixture was allowed to cool to room temperature. The reaction mixture was diluted with 30 volumes of tert-butyl methyl ether (MTBE) and filtered through celite. The celite pad was then rinsed with 10 volumes of MTBE. The organics were washed with 40 volumes of brine, 2×40 volumes of water and 40 volumes of brine. The combined organics were dried over sodium sulfate and concentrated to afford a brown solid, which was dried under vacuum (~30 in Hg) at 40° C. for 8 hours to afford the compound of Formula 3B (71% yield).

EXAMPLE 3

Step 2

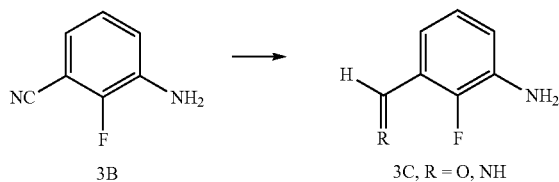

A solution of 3B in dichloromethane (about 1.5 M 3B in DCM) at RT under nitrogen mixture was cooled to ~0° C., and 2.0 eq of 1M diisobutyllithiumaluminum hydride (DIBAlH) in DCM was added dropwise over ~3.5 hours, maintaining an internal reaction temperature ≦0° C. Upon completion of the DiBAlH addition, the reaction mixture was added dropwise with vigorous stirring to a cooled solution (~0° C.) of 40 volumes of 15% Rochelle salt and 10 volumes of DCM, maintaining an internal reaction temperature below 10° C. The flask was rinsed with 10 volumes of DCM and the mixture was allowed to warm to room temperature and stirred for 4 hours. The layers were separated, and the aqueous layers were back extracted with 20 volumes of DCM. The combined organic layers were washed with 20 volumes of water. The organic layer was dried over sodium sulfate and concentrated to afford a brown foam, which was dried under vacuum (~30 in Hg) at RT to afford 3C (92% yield).

EXAMPLE 3

Step 3

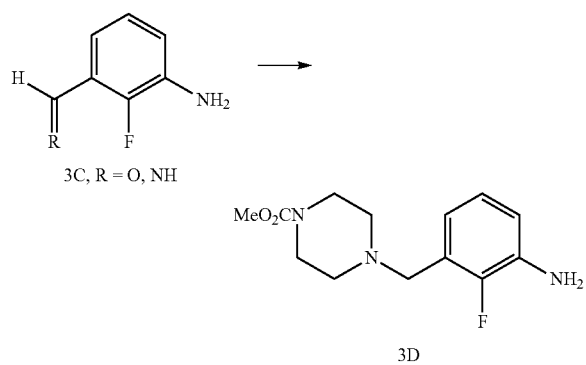

Steps 3A/B:

A solution 1 eq of 3C, tetrahydrofuran (about 1.4 M 3C in THF) and 1.05 eq of methyl piperazine-1-carboxylate and was allowed to stir at ambient temperature for 3 hours. To the reaction mixture was added 1.5 eq of sodium triacetoxyborohydride portionwise over ~40 min, maintaining an internal reaction temperature below 45° C. The reaction mixture was stirred overnight at room temperature. To the reaction mixture was added 5 volumes of water dropwise, over 1 hour, maintaining an internal reaction temperature below 30° C. Ethyl acetate (EtOAc, 5 volumes) was then added, and the layers were separated. The aqueous layers were back extracted with 5 volumes of EtOAc. The combined organic layers were washed with saturated sodium bicarbonate and solid sodium bicarbonate was added as needed to bring the pH to 8 (pHydrion papers). The layers were separated, and the organic layer was washed with 5 volumes of brine. The organic layer was dried over sodium sulfate and activated carbon was added in the drying step. The organics were filtered through celite and the celite pad was rinsed 4 times with EtOAc. The organics were concentrated and dried overnight on the rotavap (~30 in Hg at RT) to afford an amber-brown oil.

Step 3C:

All calculations are based on the amount of 3C (R=O).

To 3 volumes of methanol (based on 3C, R=O) under N2 over an ice/brine/acetone bath was added 3 eq of acetyl chloride dropwise over 3 hours, maintaining an internal reaction temperature below 0° C. The solution was then stirred for an additional 1 hour below 0° C. A solution of 1.0 eq of unpurified 3D (from Steps 3A/3B above) in MeOH (about 3.6 M based on 3C, R=)) was added dropwise over 30 min, maintaining an internal reaction temperature below 15° C. The reaction was allowed to warm to room temperature overnight. The solids were filtered the next day and rinsed with 2×0.5 volumes of MeOH, 5 volumes of 1:1 tert-butyl methyl ether (MTBE):MeOH, and 5 volumes of MTBE.

The solids were then taken up in 5 volumes of EtOAc and saturated sodium bicarbonate and solid sodium bicarbonate were added as needed to bring the pH of the aqueous layer to 8 (pHydrion papers). The layers were separated, and the aqueous layer was extracted with 5 volumes of EtOAc. The combined organic layers were washed with 5 volumes of brine, dried over sodium sulfate, and concentrated to afford a pale orange solid which was dried under vacuum (~30 in Hg) at ~40° C. to afford 3D (50% yield).

EXAMPLE 3

Step 4

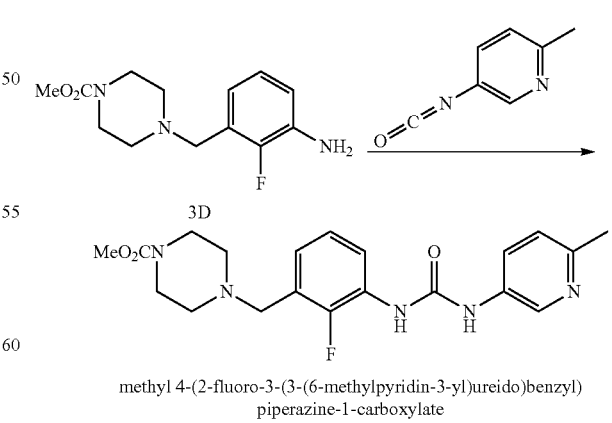

methyl 4-(2-fluoro-3-(3-(6-methylpyridin-3-yl)ureido)benzyl) piperazine-1-carboxylate To a solution of 3D in acetone (about 2.7 M 3D in acetone) was added 1.0 eq of 5-isocyanato-2-methylpyridine dropwise over 9 min. A voluminous precipitate formed during the addition, and the reaction was stirred for one hour. The reaction mixture was warmed to reflux for 2 hours and cooled to RT for 2.5 hour. The reaction was then warmed to reflux for 1 hr and cooled to RT overnight. The reaction was filtered and rinsed with 1 volume of acetone, then three times with 2 volumes of ethyl acetate. The solids were dried under vacuum (~30 in Hg) at 60° C. overnight to afford a white powder (86% yield) of methyl 4-(2-fluoro-3-(3-(6-methylpyridin-3-yl)ureido) benzyl)piperazine-1-carboxylate. The material was reworked as follows:

Methyl 4-(2-fluoro-3-(3-(6-methylpyridin-3-yl)ureido) benzyl)piperazine-1-carboxylate from above was dissolved in acetone (about 0.2 M) under N2. The reaction was then warmed to reflux for 2.5 hr and cooled to RT overnight. The reaction was filtered and rinsed with 1 volume of acetone, then three times with 2 volumes of ethyl acetate. The solids were dried under vacuum (~30 in Hg) at 60° C. overnight to afford methyl 4-(2-fluoro-3-(3-(6-methylpyridin-3-yl)ureido)benzyl)piperazine-1-carboxylate as a white powder (79% yield). The material was reworked as follows:

Methyl 4-(2-fluoro-3-(3-(6-methylpyridin-3-yl)ureido)benzyl)piper-azine-1-carboxylate from above was dissolved in acetone (about 0.2 M) under $N_2$. The reaction was then warmed to reflux and cooled to RT overnight. The reaction was filtered and rinsed with 1 volume of acetone, then three more times with 2 volumes of ethyl acetate. The solids were dried under vacuum (~30 in Hg) at 60° C. overnight to afford methyl 4-(2-fluoro-3-(3-(6-methylpyridin-3-yl)ureido)benzyl)piperazine-1-carboxylate as a white powder (73% yield). MS 402 (M+H).

EXAMPLE 4

Step 1

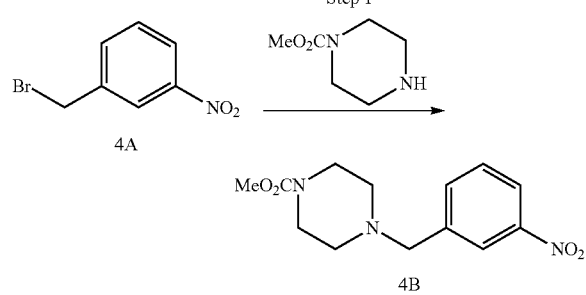

A 3-neck round bottom flask was purged with nitrogen for at least ten minutes. The flask was charged with 1.0 eq of 4A, $CH_2Cl_2$ (about 1.2 M 4A in DCM), and about 1.1 eq of DIPEA. The flask was then cooled to 10±5° C. While the flask was cooling, 1.2 eq of methyl piperazine-1-carboxylate was taken up in $CH_2Cl_2$ (about 5.3 M) The material did not go into solution, so an additional 0.05 eq of DIPEA in DCM (about 0.3 M) was added. The material did not go into solution, and the suspension was then added dropwise over 50 min, maintaining an internal reaction temperature≦30° C. The cooling bath was removed and the reaction mixture was warmed to reflux. The reaction mixture was maintained at reflux for 19 hours. An additional 0.05 eq methyl piperazine-1-carboxylate was added, and the reaction was refluxed for another 2.5 hours. The reaction was cooled to RT and washed with 5 volumes of water. The water layer was back-extracted with 5 volumes of $CH_2Cl_2$. The combined organic layers were washed with 5 volumes of 10% AcOH/water. The organic layer was then washed with 5 volumes of saturated sodium bicarbonate and 5 volumes of brine. The organic layer was dried over sodium sulfate, filtered and concentrated via rotavap at 30±5° C. to a residue. MTBE was charged to the rotavap flask at 20±5° C. and the flask was rotated until a solution had been achieved. Hexane was charged into the flask and the solution stirred for 2.5 hours at 20±5° C. The solids were filtered and rinsed with hexanes. The solids were dried at ≦40° C. under maximum vacuum until constant mass was achieved (~22 hours) to afford 4B as a pale yellow solid (66% yield).

EXAMPLE 4

Step 2

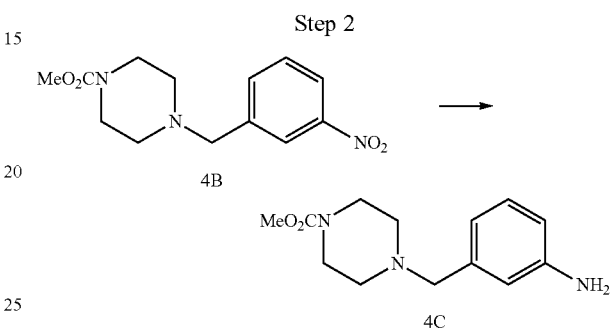

A high-pressure reactor was charged with a slurry of 25 wt % of Pt/C relative to 4B in 8 volumes of THF (relative to Pt/C) followed by a slurry of 1.5 eq $K_2CO_3$, in THF (about 0.67 M), then a solution of 1.0 eq of 4B in THF (about 0.47 M). The reactor jacket was set to 10° C., and the reactor was charged with 50 psi H2 while maintaining an internal reaction temperature≦30° C. The reaction was stirred for 9 hours, 45 min then stirred for another 3.5 hours. The reaction was filtered. The reaction flask and filters were rinsed with 9 volumes of MeOH (relative to 4B) and concentrated via rotavap at ≦50° C. The residue was dissolved in 4 volumes of EtOAc and washed with 4 volumes of water. The water layer was back-extracted with 4 volumes of EtOAc. The combined organics were washed with 4 volumes of brine, dried over sodium sulfate, filtered and concentrated via rotavap at ≦50° C. to afford a residue. Once the solvent had stopped coming off the rotavap, the residue was charged with 2 volumes of MTBE and the solution was concentrated via rotavap at ≦50° C. to afford a residue. Once the solvent had stopped coming off the rotavap, the material was kept on the rotavap under maximum vacuum for 15 hours. MTBE (2 volumes) was then charged to triturate the material and the flask rotated for 2 hours. The solids were filtered and rinsed with 0.5 volumes of MTBE. The solids were dried at ≦50° C. under maximum vacuum until constant mass was achieved (~22 hours) to afford 4C as a pale yellow solid (87% yield).

EXAMPLE 4

Step 3

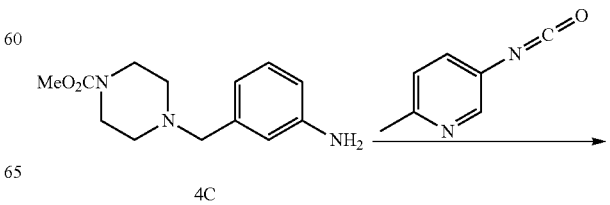

-continued

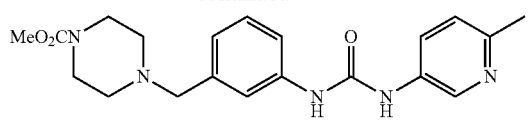

methyl 4-(3-(3-(6-methylpyridin-3-yl)ureido)benzyl)
piperazine-1-carboxylate,
4D A 3-neck round bottom flask was purged with nitrogen for at least ten minutes. The flask was then charged with 1.0 eq 4C in acetone (about 0.56 M). The flask was warmed at 27° C. to form a solution. About 1 eq 5-isocyanato-2-pyridine was added dropwise over 68 ruin, controlling the addition rate to keep the internal temperature≦45° C. After the addition, the reaction mixture was maintained ≦45° C. for approximately 5 hours. The reaction was then warmed to a gentle reflux for 35 min then cooled back to room temperature overnight (15 hrs). The solids were filtered and rinsed with 0.45 volumes of acetone and 1.7 volumes of EtOAc. The solids were dried in a vacuum oven≦50° C. to afford 4D, methyl 4-(3-(3-(6-methylpyridin-3-yl)ureido)benzyl)piperazine-1-carboxylate (89% yield). MS 384 (M+H).

EXAMPLE 5

Step 1

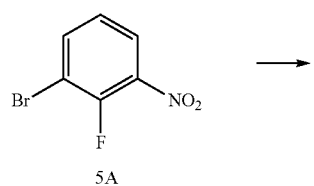

5A

To a mixture of 1.0 eq 2-fluoro-3-bromo-nitrobenzene (5A), 1.0 eq tetrabutylammonium chloride, 1.5 eq NaHCO$_3$, and 2.0 eq allyl alcohol in DMF (about 1M allyl alcohol in DMF) under N2 atmosphere was added 0.4 eq PdCl$_2$. The reaction mixture was warmed to 60° C. and stirred under N2 for 16 h. The temperature was raised to 70° C. and the reaction mixture was stirred an additional 4 h. Additional aliquots of 1 eq allyl alcohol and 0.1 eq PdCl$_2$ were added and the reaction mixture was stirred under N2 for 6 h. The reaction mixture was cooled to room temperature and diluted with EtOAc. The mixture was washed sequentially with water, 1N HCl, and brine. The organic layer was dried and concentrated to a residue. Purification over silica gel using 10% EtOAc/Hexane to 60% EtOAc/Hexane as the gradient eluant afforded 5B.

EXAMPLE 5

Step 2

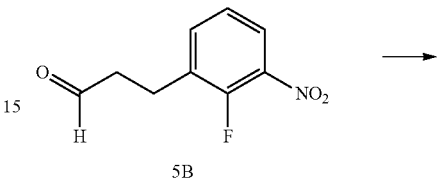

To a solution of 1.0 eq 5B in CH$_2$Cl$_2$ (about 0.04 M) under N$_2$ atmosphere was added 1.3 eq methyl piperazine-1-carboxylate HCl salt followed by 1.2 eq sodium triacetoxyborohydride. The reaction mixture was stirred at RT overnight. An additional 0.5 eq of methyl piperazine-1-carboxylate HCl salt followed by 2 eq of sodium triacetoxyborohydride was added to the reaction mixture and the mixture was stirred at RT for 4 h. The reaction mixture was diluted with CH$_2$Cl$_2$ and washed sequentially with water and brine. The organic layer was dried and concentrated to a residue. Purification over silica gel using 2:1 EtOAc/Hexane as the eluant afforded 5C.

EXAMPLE 5

Step 3

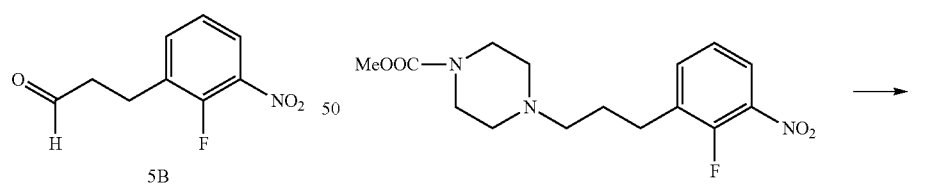

A mixture of 1 eq 5C, and 50 wt eq of 10% Pd/C in MeOH (0.06 M 5C in MeOH) was stirred over an atmosphere of 30 psi 112 for 2 h. After replacement of the H$_2$ atmosphere with N$_2$, the reaction mixture was filtered through diatomaceous

EXAMPLE 5

Step 4

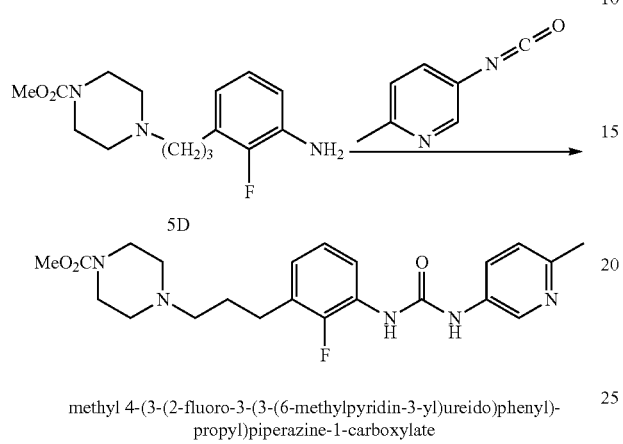

methyl 4-(3-(2-fluoro-3-(3-(6-methylpyridin-3-yl)ureido)phenyl)-propyl)piperazine-1-carboxylate To a solution of 1 eq 5D in CH$_2$Cl$_2$ (about 0.1 M) under N$_2$ atmosphere at RT was added 1 eq 5-isocyanato-2-pyridine and the resultant mixture was stirred at RT for 12 h. The reaction mixture was diluted with CH$_2$Cl$_2$ and washed sequentially with water and brine. The organic layer was dried and concentrated to a residue. Purification by preparative reverse phase HLPC (C-18 column) using 10% CH$_3$CN/water to 100% CH$_3$CN as the gradient eluant afforded methyl 4-(3-(2-fluoro-3-(3-(6-methylpyridin-3-yl)ureido)phenyl) propyl)piperazine-1-carboxylate. MS 430 (M+H).

EXAMPLE 6

Steps 1 and 2

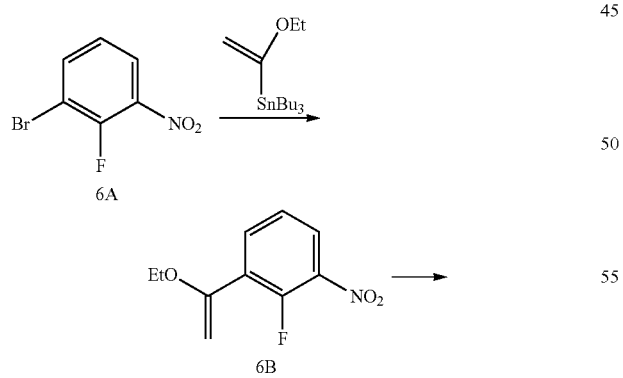

PdCl$_2$(PPh$_3$)$_2$ (0.05 eq) was added to a mixture of 1.0 eq of 6A, 1.0 eq of tributyl(1-ethoxyvinyl)-tin in dioxane (about 0.4 M) under N2. The mixture was heated at 95° C. for 4 hours under N2. A mixture of 1:1 v/v EtOAc/(1M KF) solution was added to the reaction mixture and the mixture was stirred for 1 hour. The precipitate was filtered off. The organic layer was dried and concentrated to give 6B that was used without further purification.

To a mixture of 6B in THF (0.8 M relative to 6A) was added about 2.3 volumes of 2N HCl and the mixture was stirred at RT for 1 h. Saturated NaHCO$_3$ was added to the reaction mixture. The reaction mixture was concentrated to remove THF and to the resultant mixture was added a volume of ether about 3 times that of the volume of the reaction mixture. The organic layer was dried and concentrated to a residue. The residue was purified over silica gel to obtain 6C (87% in 2 steps).

EXAMPLE 6

Step 3

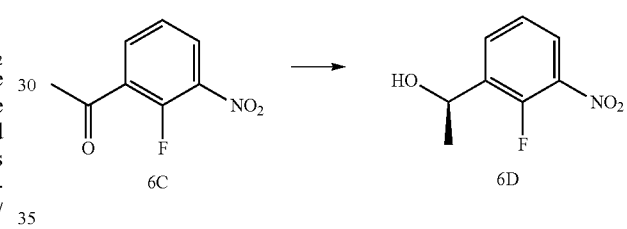

To a mixture of 0.1 to 0.15 eq of (S)-1-methyl-3,3-diphenyl-hexahydropyrrolo[1,2-c][1,3,2]oxazaborole in toluene (1-1.5 M) and toluene (a volume about 10 times that of the oxazaborole in toluene) under N2 at 20° C. was added 1.05 eq of Et$_2$NPh—BH$_3$. To this reaction mixture was added dropwise 1.0 eq 6C in toluene (about 0.4 M) over 1.5 hours. The reaction mixture was then stirred for additional 1 hour at RT. To the reaction mixture was added about 1.9 volumes of MeOH, followed by about 3.4 volumes of 1N HCl. The mixture was stirred for 20 min. To the reaction mixture was added about 7.8 volumes of ether and about 7.8 volumes of brine. The organic layer was separated, dried and concentrated to a residue. The residue was purified by chromatography over silica gel to afford 6D (79%).

EXAMPLE 6

Step 4

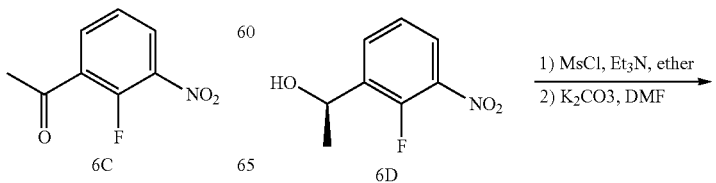

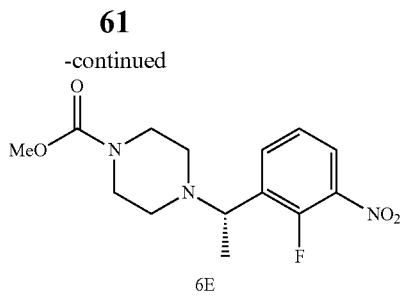

6E

To 1.0 eq 6D in ether (about 0.55 M) and 1.2 eq Et₃N was added about 1.1 eq methanesulfonyl chloride dropwise at 0° C. The mixture was stirred at RT for 30 min. The reaction mixture was filtered and concentrated to a residue. The residue was dissolved into about 5.9 volumes of DMF and 1.2 eq methyl piperazine-1-carboxylate HCl salt and 4 eq of K₂CO₃ were added. The reaction mixture was heated at 50° C. for 16 hours. The reaction mixture was cooled to RT and about 29 volumes of EtOAc and 29 volumes sat. NH₄Cl were added. The organic layer was separated, dried, and concentrated. The resultant residue was purified by chromatography over silica gel to give 6E.

EXAMPLE 6

Step 5

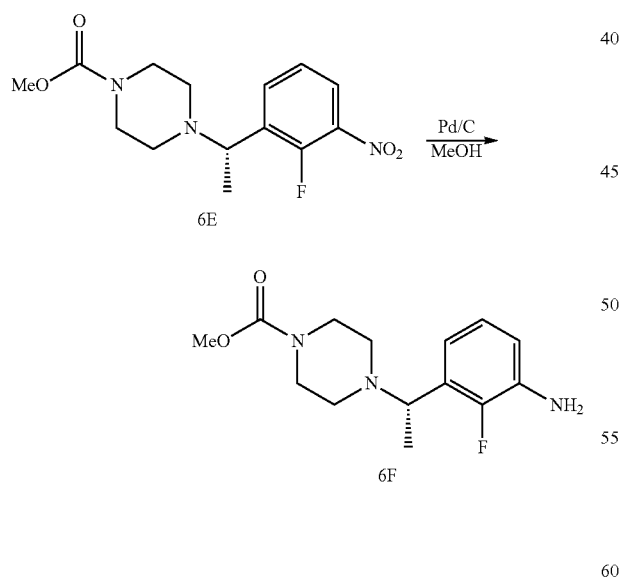

A mixture of 1 eq 6E, and 10 wt eq of 10% Pd/C in MeOH was stirred over an atmosphere of 45 psi H₂ for 0.5 h. After replacement of the H₂ atmosphere with N₂, the reaction mixture was filtered through diatomaceous earth and the diatomaceous earth washed with MeOH. Concentration of the MeOH resulted in the isolation of 6F.

EXAMPLE 6

Step 6

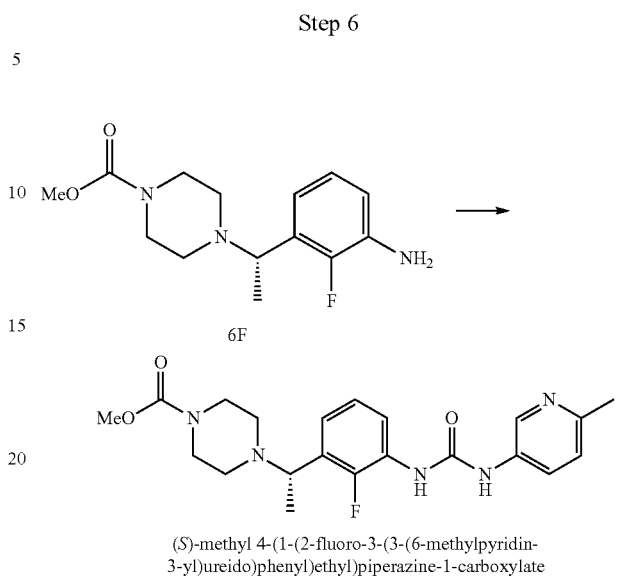

(S)-methyl 4-(1-(2-fluoro-3-(3-(6-methylpyridin-3-yl)ureido)phenyl)ethyl)piperazine-1-carboxylate To a solution of 1.0 eq 6F in CH₂Cl₂ (at about 0.3 M) under N₂ atmosphere at RT was added 1.0 eq of 5-isocyanato-2-methylpyridine and the resultant mixture was stirred at RT for 0.5 h. The reaction mixture was concentrated to a residue. Purification by reverse phase HLPC(C-18 column) afforded (S)-methyl-4-(1-(2-fluoro-3-(3-(6-methylpyridin-3-yl)ureido)phenyl)ethyl)-piperazine1-carboxylate as a white solid. MS 416 (M+H).

EXAMPLE 7

Step 1

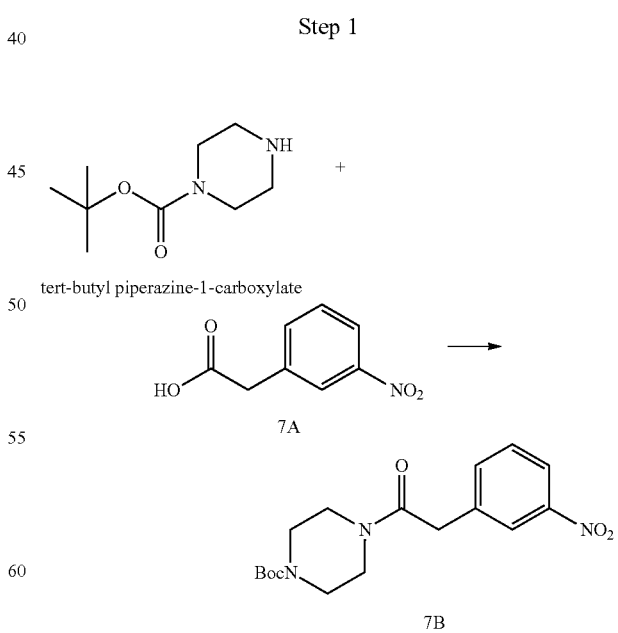

An oven-dried, round-bottom flask was charged with tert-butyl piperazine-1-carboxylate (1.1 eq), 3-nitrophenylacetic acid (7A, 1.0 eq), EDC (1.2 eq), and HOBT (1.2 eq). The flask was flushed with nitrogen, and N,N-dimethylformamide (about 0.5 M 7A in DMF) and triethylamine (2.0 eq) were added by syringe. The resulting reaction mixture was stirred overnight at room temperature. The reaction mixture was then diluted with EtOAc, and washed 4 times with H₂O, twice with 1 N aq. KHSO₄, once with saturated NaHCO₃, and once with brine. The organic layer was dried over Na₂SO₄, filtered and concentrated in vacuo. Tert-butyl 4-(2-(3-nitrophenyl)acetyl)piperazine-1-carboxylate (7B) was isolated as a solid (80%) and used without further purification.

EXAMPLE 7

Step 2

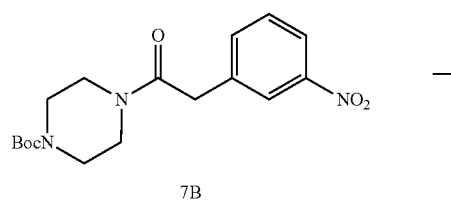

7B

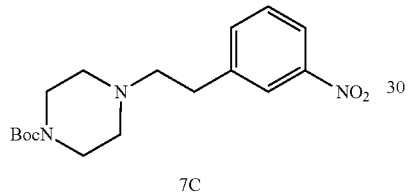

7C

To a solution of tert-butyl 4-(2-(3-nitrophenyl)acetyl)piperazine-1-carboxylate (7B, 1.0 eq) in THF (about 0.5 M 7B in TH)) was added borane-THF (2.0 eq) by syringe. The resulting reaction mixture was heated to reflux for 2 h. The reaction mixture was cooled under an ice/water bath and 10% aq. HOAc was added, slowly. The mixture was concentrated in vacuo, and the residue was dissolved in EtOAc. The organic layer was partitioned with water, and the aqueous layer was made basic (pH ~9) by the addition of 50% NaOH. The organic layer was then washed twice with saturated aq. NaHCO₃ and once with brine. The organic layer dried over Na₂SO₄, filtered and concentrated in vacuo. The resulting tert-butyl 4-(3-nitrophenethyl)piperazine-1-carboxylate (7C, quant.) was used without further purification.

EXAMPLE 7

Step 3

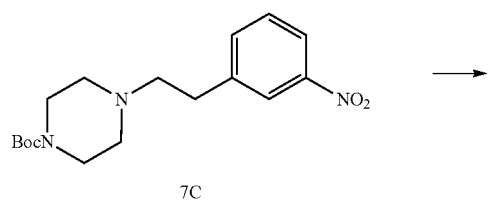

7C

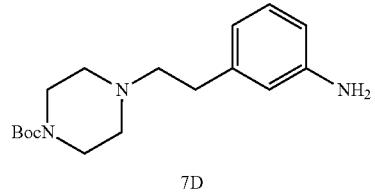

7D

A Parr glass liner was charged with tert-butyl 4-(3-nitrophenethyl)piper-azine-1-carboxylate (7C, 1.0 eq) and methanol (about 0.2 M 7C in MeOH). To this solution was added a slurry of 12.5 wt eq of 10% Pd/C in methanol. The reaction mixture was sealed in a Parr hydrogenation vessel and subjected to 3 pressurization/venting cycles with H₂. The reaction mixture was allowed to proceed at room temperature and 45 psi H₂ for 2.5 h. The reaction mixture was then charged with 12.5 wt eq of Pd(OH)₂/C and the vessel was repressurized with hydrogen (45 psi). After 1 hr, the reaction mixture was filtered through a pad of diatomaceous earth, the diatomaceous earth washed with MeOH, and the combine organic layers concentrated in vacuo to provide the desired tert-butyl 4-(3-aminophenethyl)piperazine-1-carboxylate (7D, 63%), which was used without further purification.

EXAMPLE 7

Step 4

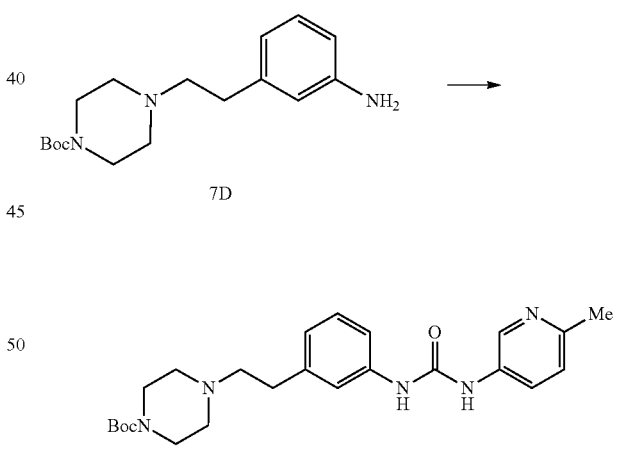

To a solution of tert-butyl 4-(3-aminophenethyl)piperazine-1-carboxylate (7D, 1.0 eq) in THF (about 0.3 M 7D in THF) was added 5-isocyanato-2-methylpyridine (1.0 eq) dropwise. The resulting reaction mixture was stirred for 2 h. To the reaction mixture was added saturated aq. NaHCO₃. The mixture was diluted with EtOAc, and the layers were separated. The organic layer was washed twice with saturated aq. NaHCO₃ and once with brine. The organic layer was dried over Na₂SO₄, filtered and concentrated in vacuo. Purification over silica gel using 5-12% MeOH/CH₂Cl₂ as the gradient eluant provided tert-butyl 4-(3-(3-(6-methylpyridin-3-yl)ureido)phenethyl)piperazine-1-carboxylate (7E, 63%).

EXAMPLE 7

Step 5

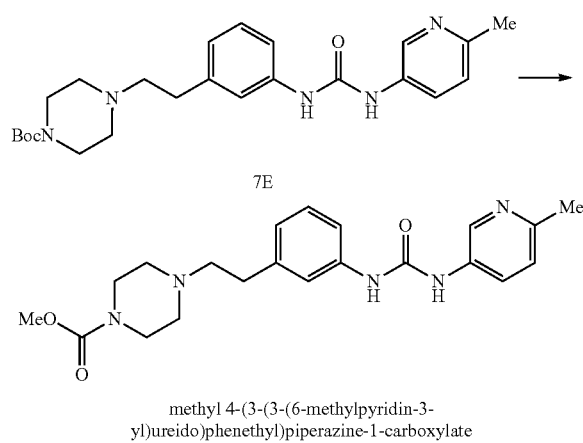

methyl 4-(3-(3-(6-methylpyridin-3-yl)ureido)phenethyl)piperazine-1-carboxylate

To a solution of tert-butyl 4-(3-(3-(6-methylpyridin-3-yl)ureido)phenethyl)piperazine-1-carboxylate (7E, 1.0 eq) in MeOH (about 0.2 M 7E in MeOH)) was added a solution of 2 M HCl in dioxane (about 12 eq). After 70 min the reaction mixture was concentrated in vacuo and used without purification for subsequent acylations. MS 398 (M+H).

The resulting HCl salt (1.0 eq) from the preceding step was suspended in THF (about 0.15 M salt in THF) and triethylamine (4.0 eq) was added. The reaction mixture was cooled to 0° C., and methyl chloroformate (1.05 eq) was added dropwise and the resultant mixture stirred for 5 min at RT. To the reaction mixture was added saturated aq. NaHCO₃ followed by EtOAc. The layers were separated, and the organic layer was washed once with saturated aq. NaHCO₃, once with brine, dried over Na₂SO₄, filtered and concentrated in vacuo. Purification over silica gel using 2-10% MeOH/CH₂Cl₂ as the gradient eluant afforded methyl 4-(3-(3-(6-methylpyridin-3-yl)ureido)phenethyl)piperazine-1-carboxylate.

EXAMPLE 8

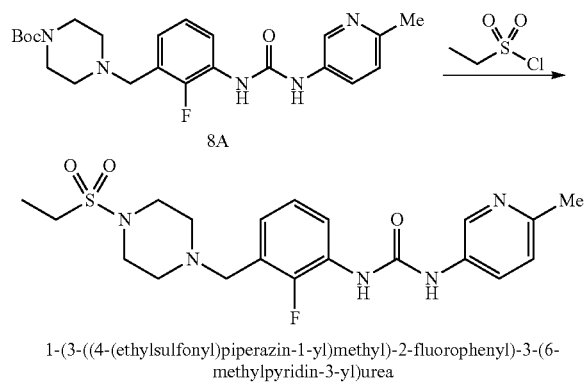

1-(3-((4-(ethylsulfonyl)piperazin-1-yl)methyl)-2-fluorophenyl)-3-(6-methylpyridin-3-yl)urea To a solution of 1.0 eq 8A in MeOH (about 0.07 M) was added a solution of 2 M HCl in dioxane (about 30 eq)). After 70 min the reaction mixture was concentrated in vacuo and used without purification for subsequent acylations.

The resulting HCl salt from the preceding step was suspended in THF (about 0.05 M) and about 18 eq diisopropylethylamine was added. The reaction mixture was cooled to 0° C., and about 1 eq ethanesulfonyl chloride was added dropwise. The resultant mixture was stirred for 5 min at RT. To the reaction mixture was added saturated aq. NaHCO₃ followed by EtOAc. The layers were separated, and the organic layer was washed once with saturated aq. NaHCO₃, once with brine, dried over Na₂SO₄, filtered and concentrated in vacuo. Purification over silica gel using 1-10% MeOH/CH₂Cl₂ as the gradient eluant followed by trituration in 1:1 actone/ether afforded methyl 1-(3-((4-(ethylsulfonyl)piperazin-1-yl)methyl)-2-fluorophenyl)-3-(6-methylpyridin-3-yl)urea. MS 436 (M+H).

EXAMPLE 9

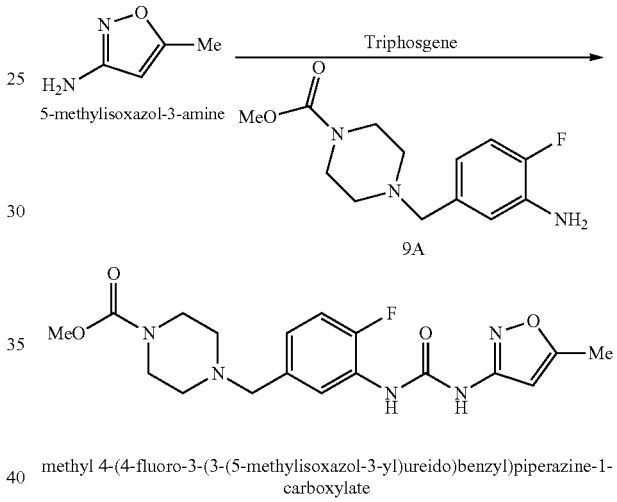

methyl 4-(4-fluoro-3-(3-(5-methylisoxazol-3-yl)ureido)benzyl)piperazine-1-carboxylate To a solution of about 0.4 eq triphosgene in THF (about 0.04 M) at RT under N2 atmosphere was added 1 eq 5-methylisoxazol-3-amine and 2 eq diisopropylethylamine in THF (about 0.2 M amine in THF). The reaction mixture was stirred for 15 min. To this mixture was added 1.0 eq 9A in THY (about 0.2 mM 9A in THF). The resultant mixture was stirred for 10 min. To the reaction mixture was added saturated aq. NaHCO₃ followed by EtOAc. The layers were separated, and the organic layer was washed once with saturated aq. NaHCO₃, once with brine, dried over Na₂SO₄, filtered and concentrated in vacuo. Purification over silica gel using 1-10% MeOH/CH₂Cl₂ as the gradient eluant afforded methyl 4-(4-fluoro-3-(3-(5-methylisoxazol-3-yl)ureido)benzyl)piperazine-1-carboxylate. MS 392 (M+H).

The following compounds were synthesized in a manner similar to the representative compounds above:

| Mass Spec data | Compound Name |
| --- | --- |
| 347 (M + H) | N-[(3-fluoro-5-{[(6-methyl(3-pyridyl))amino]carbonylamino}phenyl)methyl]methoxy-N-methylcarboxamide |

| Mass Spec data | Compound Name |
|---|---|
| 382 (M + H) | N-[3-({[(dimethylamino)sulfonyl]-methylamino}methyl)-5-fluorophenyl](3-pyridylamino)carboxamide |
| 396 (M + H) | N-[3-({[(dimethylamino)sulfonyl]-methylamino}methyl)-5-fluorophenyl][(6-methyl(3-pyridyl)amino]carboxamide |
| 381 (M + H) | N-(3-{[(ethylsulfonyl)methylamino]-methyl}-5-fluorophenyl)[(6-methyl(3-pyridyl))amino]carboxamide |
| 388 (M + H) | methyl 4-({3-fluoro-5-[(3-pyridylamino)carbonylamino]phenyl}methyl)-piperazinecarboxylate |
| 422 (M + H) | N-(3-{[4-(ethylsulfonyl)piperazinyl]-methyl}-5-fluorophenyl)(3-pyridylamino)carboxamide |
| 402 (M + H) | methyl 4-[(3-fluoro-5-{[(6-methyl(3-pyridyl))amino]carbonylamino}phenyl)methyl]-piperazinecarboxylate |
| 436 (M + H) | N-(3-{[4-(ethylsulfonyl)piperazinyl]-methyl}-5-fluorophenyl)[(6-methyl(3-pyridyl))amino]carboxamide |
| 451 (M + H) | N-[3-({4-[(dimethylamino)sulfonyl]-piperazinyl}methyl)-5-fluorophenyl][(6-methyl(3-pyridyl))amino]carboxamide |
| 437 (M + H) | N-[3-({4-[(dimethylamino)sulfonyl]-piperazinyl}methyl)-5-fluorophenyl](3-pyridylamino)carboxamide |
| 454 (M + H) | N-[3-({4-[(dimethylamino)sulfonyl]-piperazinyl}methyl)-5-fluorophenyl][(4-fluorophenyl)amino]carboxamide |
| 405 (M + H) | methyl 4-[(3-fluoro-5-{[(4-fluorophenyl)-amino]carbonylamino}phenyl)methyl]-piperazinecarboxylate |
| 439 (M + H) | N-(3-{[4-(ethylsulfonyl)piperazinyl]-methyl}-5-fluorophenyl)[(4-fluorophenyl)amino]carboxamide |
| 388 (M + H) | methyl 4-({4-fluoro-3-[(3-pyridylamino)carbonylamino]phenyl}methyl)-piperazinecarboxylate |
| 437 (M + H) | N-[5-({4-[(dimethylamino)sulfonyl]-piperazinyl}methyl)-2-fluorophenyl](3-pyridylamino)carboxamide |
| 436 (M + H) | N-(5-{[4-(ethylsulfonyl)piperazinyl]-methyl}-2-fluorophenyl)[(6-methyl(3-pyridyl))amino]carboxamide |
| 422 (M + H) | N-(5-{[4-(ethylsulfonyl)piperazinyl]-methyl}-2-fluorophenyl)(3-pyridylamino)carboxamide |
| 451 (M + H) | N-[5-({4-[(dimethylamino)sulfonyl]-piperazinyl}methyl)-2-fluorophenyl][(6-methyl(3-pyridyl))amino]carboxamide |
| 402 (M + H) | methyl 4-[(4-fluoro-3-{[(6-methyl(3-pyridyl))amino]carbonylamino}phenyl)methyl]-piperazinecarboxylate |
| 386 (M + H) | N-{3-[(4-acetylpiperazinyl)methyl]-5-fluorophenyl}[(6-methyl(3-pyridyl))amino]carboxamide |
| 422 (M + H) | N-(5-fluoro-3-{[4-(methylsulfonyl)piperazinyl]-methyl}phenyl)[(6-methyl(3-pyridyl))amino]carboxamide |
| 450 (M + H) | N-[5-fluoro-3-({4-[(methylethyl)sulfonyl]-piperazinyl}methyl)phenyl][(6-methyl(3-pyridyl))amino]carboxamide |
| 416 (M + H) | N-(5-fluoro-3-{[4-(2-methoxyacetyl)piperazinyl]-methyl}phenyl)[(6-methyl(3-pyridyl))amino]carboxamide |
| 450 (M + H) | N-(5-fluoro-3-{[4-(propylsulfonyl)piperazinyl]-methyl}phenyl)[(6-methyl(3-pyridyl))amino]carboxamide |
| 439 (M + H) | N-[3-({4-[(1E)-1-(dimethylamino)-2-cyano-2-azavinyl]piperazinyl}methyl)-5-fluoro-phenyl][(6-methyl(3-pyridyl))amino]carboxamide |
| 380 (M + H) | N-{5-fluoro-3-[(5-methyl-1,1-dioxo(1,2,5-thiadiazolidin-2-yl))methyl]phenyl}(3-pyridylamino)carboxamide |
| 394 (M + H) | N-{5-fluoro-3-[(5-methyl-1,1-dioxo(1,2,5-thiadiazolidin-2-yl))methyl]phenyl}[(6-methyl(3-pyridyl))amino]carboxamide |
| 397 (M + H) | N-{5-fluoro-3-[(5-methyl-1,1-dioxo(1,2,5-thiadiazolidin-2-yl))methyl]phenyl}[(4-fluorophenyl)amino]carboxamide |
| 402 (M + H) | methyl 4-[(2-fluoro-5-{[(6-methyl(3-pyridyl))amino]carbonylamino}phenyl)-methyl]piperazinecarboxylate |
| 436 (M + H) | N-(3-{[4-(ethylsulfonyl)piperazinyl]methyl}-4-fluorophenyl)[(6-methyl(3-pyridyl))amino]carboxamide |
| 451 (M + H) | N-[3-({4-[(dimethylamino)sulfonyl]-piperazinyl}methyl)-4-fluorophenyl][(6-methyl(3-pyridyl))amino]carboxamide |
| 388 (M + H) | methyl 4-({2-fluoro-5-[(3-pyridylamino)carbonylamino]phenyl}methyl)-piperazinecarboxylate |
| 422 (M + H) | N-(3-{[4-(ethylsulfonyl)piperazinyl]-methyl}-4-fluorophenyl)(3-pyridylamino)carboxamide |
| 437 (M + H) | N-[3-({4-[(dimethylamino)sulfonyl]-piperazinyl}methyl)-4-fluorophenyl](3-pyridylamino)carboxamide |
| 370 (M + H) | methyl 4-({3-[(3-pyridylamino)carbonylamino]phenyl}methyl)-piperazinecarboxylate |
| 404 (M + H) | N-(3-{[4-(ethylsulfonyl)piperazinyl]-methyl}phenyl)(3-pyridylamino)carboxamide |
| 418 (M + H) | N-(3-{[4-(ethylsulfonyl)piperazinyl]-methyl}phenyl)[(6-methyl(3-pyridyl))amino]carboxamide |
| 384 (M + H) | methyl 4-[(3-{[(6-methyl-3-pyridyl)amino]carbonylamino}phenyl)methyl]-piperazinecarboxylate |
| 419 (M + H) | N-[3-({4-[(dimethylamino)sulfonyl]-piperazinyl}methyl)phenyl](3-pyridylamino)carboxamide |
| 433 (M + H) | N-[3-({4-[(dimethylamino)sulfonyl]-piperazinyl}methyl)phenyl][(6-methyl(3-pyridyl))amino]carboxamide |
| 341 (M + H) | N-{5-fluoro-3-[(3-methyl-2-oxoimidazolidinyl)-methyl]phenyl}(3-pyridylamino)carboxamide |
| 355 (M + H) | N-{5-fluoro-3-[(3-methyl-2-oxoimidazolidinyl)-methyl]phenyl}[(6-methyl(3-pyridyl))amino]carboxamide |
| 358 (M + H) | N-{5-fluoro-3-[(4-methyl-3-oxopiperazinyl)-methyl]phenyl}(3-pyridylamino)carboxamide |
| 343 (M + H+) | N-[3-fluoro-5-(piperidylmethyl)-phenyl][(6-methyl(3-pyridyl))amino]carboxamide |
| 329 (M + H+) | N-[3-fluoro-5-(piperidylmethyl)phenyl]-(3-pyridylamino)carboxamide |
| 481 (M + H+) | N-[3-({(3S)-4-[(dimethylamino)sulfonyl]-3-(methoxymethyl)piperazinyl}methyl)-5-fluorophenyl](3-pyridylamino)carboxamide |
| 466 (M + H) | N-(3-{[(3S)-4-(ethylsulfonyl)-3-(methoxymethyl)-piperazinyl]methyl}-5-fluorophenyl)(3-pyridylamino)carboxamide |
| 432 (M + H) | methyl (2S)-4-({5-fluoro-3-[(3-pyridylamino)-carbonylamino]phenyl}methyl)-2-(methoxymethyl)piperazinecarboxylate |
| 495 (M + H) | N-[3-({(3S)-4-[(dimethylamino)sulfonyl]-3-(methoxymethyl)piperazinyl}methyl)-5-fluoro-phenyl][(6-methyl(3-pyridyl))amino]carboxamide |
| 480 (M + H) | N-(3-{[(3S)-4-(ethylsulfonyl)-3-(methoxymethyl)-piperazinyl]methyl}-5-fluorophenyl)[(6-methyl(3-pyridyl))amino]carboxamide |
| 446 (M + H) | methyl (2S)-4-[(5-fluoro-3-{[(6-methyl(3-pyridyl))amino]carbonylamino}phenyl)methyl]-2-(methoxymethyl)piperazinecarboxylate |
| 345 (M + H) | N-[5-fluoro-3-(morpholin-4-ylmethyl)phenyl][(6-methyl(3-pyridyl))amino]carboxamide |
| 331 (M + H) | N-[5-fluoro-3-(morpholin-4-ylmethyl)phenyl]-(3-pyridylamino)carboxamide |

| Mass Spec data | Compound Name |
|---|---|
| 393 (M + H) | N-{3-[(1,1-dioxo(1,4-thiazaperhydroin-4-yl))methyl]-5-fluorophenyl}[(6-methyl(3-pyridyl))amino]carboxamide |
| 379 (M + H) | N-{3-[(1,1-dioxo(1,4-thiazaperhydroin-4-yl))methyl]-5-fluorophenyl}(3-pyridylamino)carboxamide |
| 358 (M + H) | N-{5-fluoro-3-[(4-methylpiperazinyl)methyl]phenyl}[(6-methyl(3-pyridyl))amino]carboxamide |
| 344 (M + H) | N-{5-fluoro-3-[(4-methylpiperazinyl)methyl]phenyl}(3-pyridylamino)carboxamide |
| 451 (M + H) | N-{3-[(3S)-3-{[(dimethylamino)sulfonyl]methylamino}pyrrolidinyl)methyl]-5-fluorophenyl}(3-pyridylamino)carboxamide |
| 436 (M + H) | N-[3-({(3S)-3-[(ethylsulfonyl)methylamino]pyrrolidinyl}methyl)-5-fluorophenyl](3-pyridylamino)carboxamide |
| 402 (M + H) | N-[(3S)-1-({3-fluoro-5-[(3-pyridylamino)-carbonylamino]phenyl}methyl)pyrrolidin-3-yl]methoxy-N-methylcarboxamide |
| 465 (M + H) | N-{3-[((3S)-3-{[(dimethylamino)sulfonyl]methylamino}pyrrolidinyl)methyl]-5-fluorophenyl}[(6-methyl(3-pyridyl))amino]carboxamide |
| 450 (M + H) | N-[3-({(3S)-3-[(ethylsulfonyl)methylamino]pyrrolidinyl}methyl)-5-fluorophenyl][(6-methyl(3-pyridyl))amino]carboxamide |
| 416 (M + H) | N-{(3S)-1-[(3-fluoro-5-{[(6-methyl(3-pyridyl))amino]carbonylamino}phenyl)methyl]pyrrolidin-3-yl}methoxy-N-methylcarboxamide |
| 421 (M + H+) | N-(5-fluoro-3-{[4-(methylsulfonyl)piperidyl]methyl}phenyl)[(6-methyl(3-pyridyl))amino]carboxamide |
| 407 (M + H+) | N-(5-fluoro-3-{[4-(methylsulfonyl)piperidyl]methyl}phenyl)(3-pyridylamino)carboxamide |
| 423 (M + H) | N-(3-{[4-(ethylsulfonyl)piperazinyl]methyl}-5-fluorophenyl)(pyrimidin-5-ylamino)carboxamide |
| 438 (M + H) | N-[3-({4-[(dimethylamino)sulfonyl]piperazinyl}methyl)-5-fluorophenyl](pyrimidin-5-ylamino)carboxamide |
| 401 (M + H) | methyl 1-[(3-fluoro-5-{[(6-methyl(3-pyridyl))amino]carbonylamino}phenyl)-methyl]piperidine-4-carboxylate |
| 387 (M + H) | methyl 1-({3-fluoro-5-[(3-pyridylamino)-carbonylamino]phenyl}methyl)piperidine-4-carboxylate |
| 392 (M + H) | methyl 4-[(3-fluoro-5-{[(5-methylisoxazol-3-yl)amino]-carbonylamino}phenyl)methyl]piperazinecarboxylate |
| 441 (M + H) | N-[3-({4-[(dimethylamino)sulfonyl]piperazinyl}-methyl)-5-fluorophenyl][(5-methylisoxazol-3-yl)amino]carboxamide |
| 426 (M + H) | N-(3-{[4-(ethylsulfonyl)piperazinyl]methyl}-5-fluorophenyl)[(5-methylisoxazol-3-yl)amino]carboxamide |
| 465 (M + H) | ({5-[((3R)-3-{[(dimethylamino)sulfonyl]methylamino}piperidyl)methyl]-3-fluorophenyl}amino)-N-(3-pyridyl)carboxamide |
| 450 (M + H) | {5-({(3R)-3-[(ethylsulfonyl)methylamino]-piperidyl}methyl)-3-fluorophenyl]amino}-N-(3-pyridyl)carboxamide |
| 416 (M + H) | N-[(3R)-1-({5-fluoro-3-[(N-(3-pyridyl)-carbamoyl)amino]phenyl}methyl)(3-piperidyl)]methoxy-N-methylcarboxamide |
| 479 (M + H) | ({5-[((3R)-3-{[(dimethylamino)sulfonyl]methylamino}piperidyl)methyl]-3-fluorophenyl}amino)-N-(6-methyl(3-pyridyl))carboxamide |
| 464 (M + H) | {5-({(3R)-3-[(ethylsulfonyl)methylamino]-piperidyl}methyl)-3-fluorophenyl]amino}-N-(6-methyl(3-pyridyl))carboxamide |
| 430 (M + H) | N-{(3R)-1-[(5-fluoro-3-{[N-(6-methyl(3-pyridyl))carbamoyl]amino}phenyl)methyl](3-piperidyl)}-methoxy-N-methylcarboxamide |
| 378 (M + H) | methyl 4-({3-fluoro-5-[(isoxazol-3-ylamino)-carbonylamino]phenyl}methyl)piperazinecarboxylate |
| 412 (M + H) | N-(3-{[4-(ethylsulfonyl)piperazinyl]methyl}-5-fluorophenyl)(isoxazol-3-ylamino)carboxamide |
| 427 (M + H) | N-[3-({4-[(dimethylamino)sulfonyl]-piperazinyl}methyl)-5-fluorophenyl](isoxazol-3-ylamino)carboxamide |
| 450 (M + H) | N-[5-fluoro-3-({4-[methyl(methylsulfonyl)amino]-piperidyl}methyl)phenyl][(6-methyl(3-pyridyl))amino]carboxamide |
| 462 (M − H) | N-[3-({4-[(ethylsulfonyl)methylamino]-piperidyl}methyl)-5-fluorophenyl][(6-methyl(3-pyridyl))amino]carboxamide |
| 479 (M + H) | N-{3-[(4-{[(dimethylamino)sulfonyl]-methylamino}piperidyl)methyl]-5-fluorophenyl}[(6-methyl(3-pyridyl))amino]carboxamide |
| 430 (M + H) | N-{1-[(3-fluoro-5-{[(6-methyl(3-pyridyl))amino]carbonylamino}phenyl)methyl](4-piperidyl)}-methoxy-N-methylcarboxamide |
| 414 (M + H) | N-{1-[(3-fluoro-5-{[(6-methyl(3-pyridyl))amino]carbonylamino}phenyl)methyl](4-piperidyl)}-N-methylacetamide |
| 403 (M + H) | methyl 4-[(3-fluoro-5-{[(2-methylpyrimidin-5-yl)amino]-carbonylamino}phenyl)methyl]piperazinecarboxylate |
| 436 (M + H) | N-[5-fluoro-3-({4-[methyl(methylsulfonyl)amino]-piperidyl}methyl)phenyl](3-pyridylamino)carboxamide |
| 448 (M + H) | N-[3-({4-[(ethylsulfonyl)methylamino]-piperidyl}methyl)-5-fluorophenyl](3-pyridylamino)carboxamide |
| 465 (M + H) | N-{3-[(4-{[(dimethylamino)sulfonyl]-methylamino}piperidyl)methyl]-5-fluorophenyl}(3-pyridylamino)carboxamide |
| 416 (M + H) | N-[1-({3-fluoro-5-[(3-pyridylamino)carbonylamino]-phenyl}methyl)(4-piperidyl)]methoxy-N-methylcarboxamide |
| 400 (M + H) | N-[1-({3-fluoro-5-[(3-pyridylamino)carbonylamino]phenyl}methyl)(4-piperidyl)]-N-methylacetamide |
| 453 (M + H) | N-[5-fluoro-3-({4-[methyl(methylsulfonyl)amino]-piperidyl}methyl)phenyl](4-fluorophenyl)amino]carboxamide |
| 467 (M + H) | N-[3-({4-[(ethylsulfonyl)methylamino]piperidyl}-methyl)-5-fluorophenyl][(4-fluorophenyl)amino]carboxamide |
| 482 (M + H) | N-{3-[(4-{[(dimethylamino)sulfonyl]-methylamino}piperidyl)methyl]-5-fluorophenyl}[(4-fluorophenyl)amino]carboxamide |
| 433 (M + H) | N-{1-[(3-fluoro-5-{[(4-fluorophenyl)amino]-carbonylamino}phenyl)methyl](4-piperidyl)}methoxy-N-methylcarboxamide |
| 417 (M + H) | N-{1-[(3-fluoro-5-{[(4-fluorophenyl)amino]carbonylamino}phenyl)methyl](4-piperidyl)}-N-methylacetamide |
| 472 (M + H) | (tert-butoxy)-N-{1-[(3-fluoro-5-{[(6-methyl(3-pyridyl))amino]carbonylamino}phenyl)methyl](4-piperidyl)}-N-methylcarboxamide |
| 458 (M + H) | (tert-butoxy)-N-[1-({3-fluoro-5-[(3-pyridylamino)carbonylamino]phenyl}methyl)(4-piperidyl)]-N-methylcarboxamide |
| 475 (M + H) | (tert-butoxy)-N-{1-[(3-fluoro-5-{[(4-fluorophenyl)-amino]carbonylamino}phenyl)methyl](4-piperidyl)}-N-methylcarboxamide |
| 371 (M + H) | N-(5-fluoro-3-{[4-(methylamino)piperidyl]methyl}-phenyl)[(6-methyl(3-pyridyl))amino]carboxamide |
| 356 (M + H) | N-(5-fluoro-3-{[4-(methylamino)piperidyl]methyl}-phenyl)(3-pyridylamino)carboxamide |
| 378 (M + H) | methyl 4-({4-fluoro-3-[(1,3-oxazol-2-ylamino)-carbonylamino]phenyl}methyl)piperazinecarboxylate |
| 392 (M + H) | methyl 4-[(4-fluoro-3-{[(5-methylisoxazol-3-yl)amino]-carbonylamino}phenyl)methyl]piperazinecarboxylate |
| 403 (M + H) | methyl 4-[(4-fluoro-3-{[(2-methylpyrimidin-5-yl)amino]-carbonylamino}phenyl)methyl]piperazinecarboxylate |
| 391 (M + H) | methyl 4-[(4-fluoro-3-{[(1-methylpyrazol-3-yl)amino]carbonylamino}phenyl)methyl]-piperazinecarboxylate |
| 391 (M − H) | 1-[(3-fluoro-5-{[(6-methyl(3-pyridyl))amino]-carbonylamino}phenyl)methyl]piperidine-4-carboxylic acid |
| 379 (M − H) | 1-({3-fluoro-5-[(3-pyridylamino)carbonylamino]-phenyl}methyl)piperidine-4-carboxylic acid |

| Mass Spec data | Compound Name |
|---|---|
| 345 (M + H) | N-[2-fluoro-5-(morpholin-4-ylmethyl)phenyl][(6-methyl(3-pyridyl))amino]carboxamide |
| 339 (M + H) | methyl 4-({4-fluoro-3-[(pyrimidin-5-ylamino)-carbonylamino]phenyl}methyl)piperazinecarboxylate |
| 430 (M + H) | N-{(3R)-1-[(4-fluoro-3-{[N-(6-methyl(3-pyridyl))carbamoyl]amino}phenyl)methyl](3-piperidyl)}methoxy-N-methylcarboxamide |
| 444 (M + H) | N-{(3R)-1-[(4-fluoro-3-{[N-(6-methyl(3-pyridyl))carbamoyl]amino}phenyl)methyl](3-piperidyl)}ethoxy-N-methylcarboxamide |
| 458 (M + H) | N-{(3R)-1-[(4-fluoro-3-{[N-(6-methyl(3-pyridyl))carbamoyl]amino}phenyl)methyl](3-piperidyl)}-N-methyl(methylethoxy)carboxamide |
| 414 (M + H) | N-{(3R)-1-[(4-fluoro-3-{[N-(6-methyl(3-pyridyl))carbamoyl]amino}phenyl)methyl](3-piperidyl)}-N-methylacetamide |
| 428 (M + H) | N-{(3R)-1-[(4-fluoro-3-{[N-(6-methyl(3-pyridyl))carbamoyl]amino}phenyl)methyl](3-piperidyl)}-N-methylpropanamide |
| 442 (M + H) | N-{(3R)-1-[(4-fluoro-3-{[N-(6-methyl(3-pyridyl))carbamoyl]amino}phenyl)methyl](3-piperidyl)}-2-methyl-N-methylpropanamide |
| 393 (M + H) | methyl 4-[(4-fluoro-3-{[(5-methyl(1,3,4-oxadiazol-2-yl))amino]carbonylamino}phenyl)methyl]-piperazinecarboxylate |
| 392 (M + H) | methyl 4-[(4-fluoro-3-{[(4-methyl(1,3-oxazol-2-yl))amino-carbonylamino}phenyl)methyl]-piperazinecarboxylate |
| 418 (M + H) | methyl 4-[(4-chloro-3-{[(6-methyl(3-pyridyl))amino]-carbonylamino}phenyl)methyl]piperazinecarboxylate |
| 416 (M + H) | ethyl 4-[(4-fluoro-3-{[(6-methyl(3-pyridyl))amino]-carbonylamino}phenyl)methyl]piperazinecarboxylate |
| 430 (M + H) | methylethyl 4-[(4-fluoro-3-{[(6-methyl(3-pyridyl))amino]carbonylamino}phenyl)methyl]-piperazinecarboxylate |
| 386 (M + H) | N-{5-[(4-acetylpiperazinyl)methyl]-2-fluorophenyl}[(6-methyl(3-pyridyl))amino]carboxamide |
| 400 (M + H) | N-{2-fluoro-5-[(4-propanoylpiperazinyl)methyl]-phenyl}[(6-methyl(3-pyridyl))amino]carboxamide |
| 414 (M + H) | N-(2-fluoro-5-{[4-(2-methylpropanoyl)piperazinyl]-methyl}phenyl)[(6-methyl(3-pyridyl))amino]carboxamide |
| 458 (M + H) | N-[5-({(3R)-3-[(tert-butoxy)-N-methylcarbonylamino]pyrrolidinyl}methyl)-2-fluorophenyl][(6-methyl(3-pyridyl))amino]carboxamide |
| 358 (M + H) | N-(5-{[(3R)-3-(methylamino)pyrrolidinyl]-methyl}-2-fluorophenyl)[(6-methyl(3-pyridyl))amino]carboxamide |
| 416 (M + H) | N-(5-{[(3R)-3-(methoxy-N-methylcarbonylamino)-pyrrolidinyl]methyl}-2-fluorophenyl)[(6-methyl(3-pyridyl))amino]carboxamide |
| 430 (M + H) | N-(5-{[(3R)-3-(ethoxy-N-methylcarbonylamino)-pyrrolidinyl]methyl}-2-fluorophenyl)[(6-methyl(3-pyridyl))amino]carboxamide |
| 444 (M + H) | N-[5-({(3R)-3-[N-methyl(methylethoxy)-carbonylamino]pyrrolidinyl}methyl)-2-fluorophenyl][(6-methyl(3-pyridyl))amino]carboxamide |
| 400 (M + H) | N-{(3R)-1-[(4-fluoro-3-{[(6-methyl(3-pyridyl))amino]carbonylamino}phenyl)methyl]pyrrolidin-3-yl}-N-methylacetamide |
| 414 (M + H) | N-(5-{[4-(N,N-dimethylcarbamoyl)piperidyl]-methyl}-3-fluorophenyl)[(6-methyl(3-pyridyl))amino]carboxamide |
| 400 (M + H) | N-(3-fluoro-5-{[4-(N-methylcarbamoyl)piperidyl]-methyl}phenyl)[(6-methyl(3-pyridyl))amino]carboxamide |
| 472 (M + H) | N-{(3S)-1-[(4-fluoro-3-{[(6-methyl(3-pyridyl))amino]carbonylamino}phenyl)methyl](3-piperidyl)}(tert-butoxy)-N-methylcarboxamide |
| 398 (M + H) | methyl 4-[(4-methyl-3-{[(6-methyl(3-pyridyl))amino]carbonylamino}phenyl)methyl]-piperazinecarboxylate |
| 488 (M + H) | tert-butyl (2S)-4-[(4-fluoro-3-{[(6-methyl(3-pyridyl))amino]carbonylamino}phenyl)methyl]-2-(methoxymethyl)piperazinecarboxylate |
| 446 (M + H) | methyl (2S)-4-[(4-fluoro-3-{[(6-methyl(3-pyridyl))amino]carbonylamino}phenyl)methyl]-2-(methoxymethyl)piperazinecarboxylate |
| 460 (M + H) | ethyl (2S)-4-[(4-fluoro-3-{[(6-methyl(3-pyridyl))amino]carbonylamino}phenyl)methyl]-2-(methoxymethyl)piperazinecarboxylate |
| 474 (M + H) | methylethyl (2S)-4-[(4-fluoro-3-{[(6-methyl(3-pyridyl))amino]carbonylamino}phenyl)methyl]-2-(methoxymethyl)piperazinecarboxylate |
| 430 (M + H) | N-(5-{[(3S)-4-acetyl-3-(methoxymethyl)-piperazinyl]methyl}-2-fluoro-phenyl)[(6-methyl(3-pyridyl))amino]carboxamide |
| 444 (M + H) | N-(5-{[(3S)-3-(methoxymethyl)-4-propanoylpiperazinyl]methyl}-2-fluoro-phenyl)[(6-methyl(3-pyridyl))amino]carboxamide |
| 458 (M + H) | N-(5-{[(3S)-3-(methoxymethyl)-4-(2-methylpropanoyl)piperazinyl]methyl}-2-fluoro-phenyl)[(6-methyl(3-pyridyl))amino]carboxamide |
| 416 (M + H) | N-(5-{[(3S)-3-(methoxy-N-methyl-carbonylamino)pyrrolidinyl]methyl}-2-fluoro-phenyl)[(6-methyl(3-pyridyl))amino]carboxamide |
| 430 (M + H) | N-(5-{[(3S)-3-(ethoxy-N-methylcarbonylamino)-pyrrolidinyl]methyl}-2-fluoro-phenyl)[(6-methyl(3-pyridyl))amino]carboxamide |
| 444 (M + H) | N-[5-({(3S)-3-[N-methyl(methylethoxy)-carbonylamino]pyrrolidinyl}methyl)-2-fluoro-phenyl][(6-methyl(3-pyridyl))amino]carboxamide |
| 400 (M + H) | N-{(3S)-1-[(4-fluoro-3-{[(6-methyl(3-pyridyl))amino]-carbonylamino}phenyl)methyl]pyrrolidin-3-yl}-N-methylacetamide |
| 414 (M + H) | N-{(3S)-1-[(4-fluoro-3-{[(6-methyl(3-pyridyl))amino]-carbonylamino}phenyl)methyl]pyrrolidin-3-yl}-N-methylpropanamide |
| 428 (M + H) | N-{(3S)-1-[(4-fluoro-3-{[(6-methyl(3-pyridyl))amino]-carbonylamino}phenyl)methyl]pyrrolidin-3-yl}-2-methyl-N-methylpropanamide |
| 430 (M + H) | N-(2-fluoro-5-{[4-(methoxy-N-methyl-carbonylamino)piperidyl]methyl}phenyl)[(6-methyl(3-pyridyl))amino]carboxamide |
| 444 (M + H) | N-(5-{[4-(ethoxy-N-methylcarbonylamino)-piperidyl]methyl}-2-fluorophenyl)-[(6-methyl(3-pyridyl))amino]carboxamide |
| 458 (M + H) | N-[2-fluoro-5-({4-[N-methyl-(methylethoxy)carbonylamino]piperidyl}methyl)-phenyl][(6-methyl(3-pyridyl))amino]carboxamide |
| 414 (M + H) | N-{1-[(4-fluoro-3-{[(6-methyl(3-pyridyl))amino]-carbonylamino}phenyl)methyl](4-piperidyl)}-N-methylacetamide |
| 428 (M + H) | N-{1-[(4-fluoro-3-{[(6-methyl(3-pyridyl))amino]-carbonylamino}phenyl)methyl](4-piperidyl)}-N-methylpropanamide |
| 442 (M + H) | N-{1-[(4-fluoro-3-{[(6-methyl(3-pyridyl))amino]-carbonylamino}phenyl)methyl](4-piperidyl)}-2-methyl-N-methylpropanamide |
| 414 (M + H) | N-{(3R)-1-[(4-fluoro-3-{[(6-methyl(3-pyridyl))amino]-carbonylamino}phenyl)methyl]pyrrolidin-3-yl}-N-methylpropanamide |
| 428 (M + H) | N-{(3R)-1-[(4-fluoro-3-{[(6-methyl(3-pyridyl))amino]-carbonylamino}phenyl)methyl]pyrrolidin-3-yl}-2-methyl-N-methylpropanamide |
| 373 (M + H) | N-{5-[((3S,5R)-3,5-dimethylmorpholin-4-yl)methyl]-2-fluorophenyl}[(6-methyl(3-pyridyl))amino]carboxamide |
| 430 (M + H) | N-{(3S)-1-[(4-fluoro-3-{[(6-methyl(3-pyridyl))amino]carbonylamino}phenyl)methyl](3-piperidyl)}methoxy-N-methylcarboxamide |
| 444 (M + H) | N-{(3S)-1-[(4-fluoro-3-{[(6-methyl(3-pyridyl))amino]carbonylamino}phenyl)methyl](3-piperidyl)}ethoxy-N-methylcarboxamide |
| 458 (M + H) | N-{(3S)-1-[(4-fluoro-3-{[(6-methyl(3-pyridyl))amino]carbonylamino}phenyl)methyl](3-piperidyl)}-N-methyl(methylethoxy)carboxamide |
| 444 (M + H) | tert-butyl 4-[(4-fluoro-3-{[(6-methyl(3-pyridyl))amino]carbonylamino}phenyl)methyl]-piperazinecarboxylate |

| Mass Spec data | Compound Name |
|---|---|
| 414 (M + H) | N-{(3S)-1-[(4-fluoro-3-{[(6-methyl(3-pyridyl))amino]-carbonylamino}phenyl)methyl](3-piperidyl)}-N-methylacetamide |
| 344 (M + H) | N-[2-fluoro-5-(piperazinylmethyl)phenyl][(6-methyl(3-pyridyl))amino]carboxamide |
| 446 (M + H) | methyl (2R)-4-[(4-fluoro-3-{[(6-methyl(3-pyridyl))amino]carbonylamino}phenyl)methyl]-2-(methoxymethyl)piperazinecarboxylate |
| 430 (M + H) | N-(5-{[(3R)-4-acetyl-3-(methoxymethyl)piperazinyl]-methyl}-2-fluorophenyl)[(6-methyl(3-pyridyl))amino]carboxamide |
| 460 (M + H) | ethyl (2R)-4-[(4-fluoro-3-{[(6-methyl(3-pyridyl))amino]carbonylamino}phenyl)methyl]-2-(methoxymethyl)piperazinecarboxylate |
| 474 (M + H) | methylethyl (2R)-4-[(4-fluoro-3-{[(6-methyl(3-pyridyl))amino]carbonylamino}phenyl)methyl]-2-(methoxymethyl)piperazinecarboxylate |
| 466 (M + H) | N-(5-{[(3R)-3-(methoxymethyl)-4-(methylsulfonyl)-piperazinyl]methyl}-2-fluorophenyl)[(6-methyl(3-pyridyl))amino]carboxamide |
| 372 (M + H) | N-(5-{[(3S)-3-(methylamino)piperidyl]methyl}-2-fluorophenyl)[(6-methyl(3-pyridyl))amino]carboxamide |
| 428 (M + H) | N-{(3S)-1-[(4-fluoro-3-{[(6-methyl(3-pyridyl))amino]-carbonylamino}phenyl)methyl](3-piperidyl)}-N-methylpropanamide |
| 442 (M + H) | N-{(3S)-1-[(4-fluoro-3-{[(6-methyl(3-pyridyl))amino]-carbonylamino}phenyl)methyl](3-piperidyl)}-2-methyl-N-methylpropanamide |
| 458 (M + H) | tert-butyl 4-[(4-fluoro-3-{[(6-methyl(3-pyridyl))amino]carbonylamino}phenyl)methyl]-1,4-diazaperhydroepinecarboxylate |
| 400 (M + H) | N-(3-{[4-(N,N-dimethylcarbamoyl)piperidyl]-methyl}-5-fluorophenyl)(3-pyridylamino)carboxamide |
| 389 (M + H) | methyl 4-({4-fluoro-3-[(pyridazin-4-ylamino)carbonylamino]phenyl}methyl)-piperazinecarboxylate |
| 480 (M + H) | N-(5-{[(3R)-4-(ethylsulfonyl)-3-(methoxymethyl)-piperazinyl]methyl}-2-fluoro-phenyl)[(6-methyl(3-pyridyl))amino]carboxamide |
| 386 (M + H) | N-(5-fluoro-3-{[4-(N-methylcarbamoyl)-piperidyl]-methyl}phenyl)(3-pyridylamino)carboxamide |
| 378 (M + H) | methyl 4-({4-fluoro-3-[(isoxazol-3-ylamino)carbonylamino]phenyl}methyl)-piperazinecarboxylate |
| 400 (M + H) | N-{3-[((1S)-7-oxo-8-oxa-3,6-diazabicyclo[4.3.0]non-3-yl)methyl]-5-fluoro-phenyl}[(6-methyl(3-pyridyl))amino]carboxamide |
| 400 (M + H) | N-{5-[((1S)-7-oxo-8-oxa-3,6-diazabicyclo[4.3.0]non-3-yl)methyl]-2-fluoro-phenyl}[(6-methyl(3-pyridyl))amino]carboxamide |
| 416 (M + H) | methyl 4-[(5-fluoro-3-{[(6-methyl(3-pyridyl))amino]carbonylamino}phenyl)ethyl]-piperazinecarboxylate |
| 430 (M + H) | ethyl 4-[(5-fluoro-3-{[(6-methyl(3-pyridyl))amino]carbonylamino}phenyl)ethyl]-piperazinecarboxylate |
| 400 (M + H) | N-{3-[(4-acetylpiperazinyl)ethyl]-5-fluorophenyl}[(6-methyl(3-pyridyl))amino]carboxamide |
| 358 (M + H) | N-[5-(1,4-diazaperhydroepinylmethyl)-2-fluorophenyl][(6-methyl(3-pyridyl))amino]carboxamide |
| 416 (M + H) | methyl 4-[(4-fluoro-3-{[(6-methyl(3-pyridyl))amino]carbonylamino}phenyl)methyl]-1,4-diazaperhydroepinecarboxylate |
| 430 (M + H) | ethyl 4-[(4-fluoro-3-{[(6-methyl(3-pyridyl))amino]carbonylamino}phenyl)methyl]-1,4-diazaperhydroepinecarboxylate |
| 444 (M + H) | methylethyl 4-[(4-fluoro-3-{[(6-methyl(3-pyridyl))amino]carbonylamino}phenyl)methyl]-1,4-diazaperhydroepinecarboxylate |
| 400 (M + H) | N-{5-[(4-acetyl(1,4-diazaperhydroepinyl))-methyl]-2-fluorophenyl}[(6-methyl(3-pyridyl))amino]carboxamide |
| 401 (M + H) | N-{5-[(1,4-dioxa-8-azaspiro[4.5]dec-8-yl)-methyl]-2-fluorophenyl}[(6-methyl(3-pyridyl))amino]carboxamide |
| 373 (M + H) | N-{2-fluoro-5-[(4-methoxypiperidyl)methyl]-phenyl}[(6-methyl(3-pyridyl))amino]carboxamide |
| 357 (M + H) | N-[5-(azaperhydroepinylmethyl)-2-fluorophenyl][(6-methyl(3-pyridyl))amino]carboxamide |
| 426 (M + H) | N-{2-fluoro-5-[(4-piperidylpiperidyl)methyl]-phenyl}[(6-methyl(3-pyridyl))amino]carboxamide |
| 455 (M + H) | N-(5-{[4-(cyclohexylmethoxy)piperidyl]-methyl}-2-fluorophenyl)[(6-methyl(3-pyridyl))amino]carboxamide |
| 375 (M + H) | N-(2-fluoro-5-{[2-(hydroxymethyl)morpholin-4-yl]methyl}phenyl)[(6-methyl(3-pyridyl))amino]carboxamide |
| 389 (M + H) | N-(2-fluoro-5-{[2-(methoxymethyl)morpholin-4-yl]methyl}phenyl)[(6-methyl(3-pyridyl))amino]carboxamide |
| 420 (M + H) | methyl 4-[(2,4-difluoro-5-{[(6-methyl(3-pyridyl))amino]carbonylamino}phenyl)methyl]-piperazinecarboxylate |
| 401 (M + H) | N-{2-fluoro-5-[(4-propoxypiperidyl)methyl]-phenyl}[(6-methyl(3-pyridyl))amino]carboxamide |
| 357 (M + H) | N-{2-fluoro-5-[(4-methylpiperidyl)methyl]-phenyl}[(6-methyl(3-pyridyl))amino]carboxamide |
| 465 (M + H) | N-[5-({4-[(dimethylamino)sulfonyl](1,4-diazaperhydroepinyl)}methyl)-2-fluoro-phenyl][(6-methyl(3-pyridyl))amino]carboxamide |
| 444 (M + H) | propyl 4-[(4-fluoro-3-{[(6-methyl(3-pyridyl))amino]carbonylamino}phenyl)methyl]-1,4-diazaperhydroepinecarboxylate |
| 400 (M + H) | N-{3-[((1R)-7-oxo-8-oxa-3,6-diazabicyclo[4.3.0]non-3-yl)methyl]-5-fluoro-phenyl}[(6-methyl(3-pyridyl))amino]carboxamide |
| 436 (M + H) | N-{2-fluoro-5-{[4-(methylsulfonyl)(1,4-diazaperhydroepinyl)]methyl}phenyl)[(6-methyl(3-pyridyl))amino]carboxamide |
| 449 (M + H) | N-{3-[((1R)-8-methyl-7,7-dioxo-7-thia-3,6,8-triazabicyclo[4.3.0]non-3-yl)methyl]-5-fluorophenyl}[(6-methyl(3-pyridyl))amino]-carboxamide |
| 450 (M + H) | N-(5-{[4-(ethylsulfonyl)(1,4-diazaperhydroepinyl)]-methyl}-2-fluorophenyl)[(6-methyl(3-pyridyl))amino]carboxamide |
| 449 (M + H) | N-{5-[((1R)-8-methyl-7,7-dioxo-7-thia-3,6,8-triazabicyclo[4.3.0]non-3-yl)methyl]-2-fluorophenyl}[(6-methyl(3-pyridyl))amino]-carboxamide |
| 465 (M + H) | N-[2-fluoro-5-({4-[(methylethyl)sulfonyl](1,4-diazaperhydroepinyl)}methyl)phenyl][(6-methyl(3-pyridyl))amino]-carboxamide |
| 449 (M + H) | N-{3-[((1S)-8-methyl-7,7-dioxo-7-thia-3,6,8-triazabicyclo[4.3.0]non-3-yl)methyl]-5-fluorophenyl}[(6-methyl(3-pyridyl))amino]-carboxamide |
| 449 (M + H) | N-{5-[((1S)-8-methyl-7,7-dioxo-7-thia-3,6,8-triazabicyclo[4.3.0]non-3-yl)methyl]-2-fluorophenyl}[(6-methyl(3-pyridyl))amino]-carboxamide |
| 400 (M + H) | N-{5-[((1R)-7-oxo-8-oxa-3,6-diazabicyclo[4.3.0]non-3-yl)methyl]-2-fluoro-phenyl}[(6-methyl(3-pyridyl))amino]carboxamide |
| 418 (M + H) | methyl 4-[(4-fluoro-3-{[(6-methoxy(3-pyridyl))amino]carbonylamino}phenyl)methyl]-piperazinecarboxylate |
| 402 (M + H) | N-{5-[((1R)-7-oxo-8-oxa-3,6-diazabicyclo[4.3.0]non-3-yl)methyl]-2-fluoro-phenyl}[(6-methyl(3-pyridyl))amino]carboxamide |
| 438 (M + H) | methyl 4-[(2,4,5-trifluoro-3-{[(6-methyl(3-pyridyl))amino]carbonylamino}phenyl)methyl]-piperazinecarboxylate |

-continued

| Mass Spec data | Compound Name |
|---|---|
| 451 (M + H) | N-[2-fluoro-5-({4-[methyl(methylsulfonyl)amino]-piperidyl}methyl)phenyl][(6-methyl(3-pyridyl))amino]carboxamide |
| 414 (M + H) | N-{3-[3-(4-acetylpiperazinyl)propyl]-5-fluorophenyl}[(6-methyl(3-pyridyl))amino]carboxamide |
| 430 (M + H) | methyl 4-[3-(3-fluoro-5-{[(6-methyl(3-pyridyl))amino]carbonylamino}phenyl)propyl]-piperazinecarboxylate |
| 475 (M + H) | (tert-butoxy)-N-{1-[(4-fluoro-3-{[(4-fluoro-phenyl)amino]carbonylamino}phenyl)methyl](4-piperidyl)}-N-methylcarboxamide |
| 475 (M + H) | N-(2-fluoro-5-{[4-(methylamino)piperidyl]-methyl}phenyl)[(4-fluorophenyl)amino]carboxamide |
| 413 (M + H) | methyl 4-[(3-{[(6-cyano(3-pyridyl))amino]-carbonylamino}-5-fluorophenyl)methyl]piperazinecarboxylate |
| 427 (M + H) | ethyl 4-[(3-{[(6-cyano(3-pyridyl))amino]-carbonylamino}-5-fluorophenyl)methyl]piperazinecarboxylate |
| 441 (M + H) | methylethyl 4-(3-{[(6-cyano(3-pyridyl))amino]-carbonylamino}-5-fluorophenyl)methyl]piperazinecarboxylate |
| 397 (M + H) | N-{3-[(4-acetylpiperazinyl)methyl]-5-fluorophenyl}[(6-cyano(3-pyridyl))amino]carboxamide |
| 462 (M + H) | N-[3-({4-[(dimethylamino)sulfonyl]piperazinyl}-methyl)-5-fluorophenyl][(6-cyano(3-pyridyl))amino]carboxamide |
| 447 (M + H) | [(6-cyano(3-pyridyl))amino]-N-(3-{[4-(ethylsulfonyl)piperazinyl]methyl}-5-fluorophenyl)carboxamide |
| 453 (M + H) | N-[2-fluoro-5-({4-[methyl(methylsulfonyl)amino]-piperidyl}methyl)phenyl][(4-fluorophenyl)amino]carboxamide |
| 467 (M + H) | N-[5-({4-[(ethylsulfonyl)methylamino]piperidyl}-methyl)-2-fluorophenyl][(4-fluorophenyl)amino]carboxamide |
| 458 (M + H) | tert-butyl (3S)-3-{[(4-fluoro-3-{[(6-methyl(3-pyridyl))amino]carbonylamino}phenyl)methyl]-methylamino}-pyrrolidinecarboxylate |
| 416 (M + H) | methyl (3S)-3-{[(4-fluoro-3-{[(6-methyl(3-pyridyl))amino]carbonylamino}phenyl)methyl]-methylamino}-pyrrolidinecarboxylate |
| 416 (M + H) | methyl (3R)-3-{[(4-fluoro-3-{[(6-methyl(3-pyridyl))amino]carbonylamino}phenyl)methyl]-methylamino}-pyrrolidinecarboxylate |
| 398 (M + H) | methyl 4-[(2-methyl-3-{[(6-methyl(3-pyridyl))amino]-carbonylamino}phenyl)methyl]piperazinecarboxylate |
| 418 (M + H) | methyl 4-[(2-chloro-5-{[(6-methyl(3-pyridyl))amino]-carbonylamino}phenyl)methyl]piperazinecarboxylate |
| 429 (M + H) | 2-{4-[(3-fluoro-5-{[(6-methyl(3-pyridyl))amino]-carbonylamino}phenyl)methyl]piperazinyl}-N,N-dimethylacetamide |
| 444 (M + H) | ethyl 4-[(3-{[(6-acetyl(3-pyridyl))amino]-carbonylamino}-5-fluorophenyl)methyl]piperazinecarboxylate |
| 400 (M + H) | N-{3-[3-(4-acetylpiperazinyl)propyl]-5-fluorophenyl}(3-pyridylamino)carboxamide |
| 416 (M + H) | methyl 4-(3-{3-fluoro-5-[(3-pyridylamino)-carbonylamino]phenyl}propyl)piperazinecarboxylate |
| 450 (M + H) | N-(3-{3-[4-(ethylsulfonyl)piperazinyl]propyl}-5-fluorophenyl)(3-pyridylamino)carboxamide |
| 444 (M + H) | ethyl 4-[3-(3-fluoro-5-{[(6-methyl(3-pyridyl))amino]-carbonylamino}phenyl)propyl]piperazinecarboxylate |
| 458 (M + H) | methylethyl 4-[3-(3-fluoro-5-{[(6-methyl(3-pyridyl))amino]-carbonylamino}phenyl)propyl]-piperazinecarboxylate |
| 464 (M + H) | N-(3-{3-[4-(ethylsulfonyl)piperazinyl]propyl}-5-fluorophenyl)[(6-methyl(3-pyridyl))amino]carboxamide |
| 479 (M + H) | N-[3-(3-{4-[(dimethylamino)sulfonyl]-piperazinyl}propyl)-5-fluorophenyl][(6-methyl(3-pyridyl))amino]carboxamide |

| Mass Spec data | Compound Name |
|---|---|
| 430 (M + H) | N-{3-[3-(4-acetylpiperazinyl)propyl]-5-fluorophenyl}[(6-methoxy(3-pyridyl))amino]carboxamide |
| 446 (M + H) | methyl 4-[3-(3-fluoro-5-{[(6-methoxy(3-pyridyl))amino]carbonylamino}phenyl)propyl]-piperazinecarboxylate |
| 480 (M + H) | N-(3-{3-[4-(ethylsulfonyl)piperazinyl]propyl}-5-fluorophenyl)[(6-methoxy(3-pyridyl))amino]carboxamide |
| 430 (M + H) | methyl 4-[(3-{[(6-acetyl(3-pyridyl))amino]-carbonylamino}-5-fluorophenyl)methyl]piperazinecarboxylate |
| 358 (M + H) | N-(5-{[((3S)pyrrolidin-3-yl)methylamino]-methyl}-2-fluorophenyl)[(6-methyl(3-pyridyl))amino]carboxamide |
| 458 (M + H) | tert-butyl (3R)-3-{[(4-fluoro-3-{[(6-methyl(3-pyridyl))amino]carbonylamino}phenyl)methyl]-methylamino}-pyrrolidinecarboxylate |
| 358 (M + H) | N-(5-{[((3R)pyrrolidin-3-yl)methylamino]-methyl}-2-fluorophenyl)[(6-methyl(3-pyridyl))amino]carboxamide |
| 444 (M + H) | N-ethyl-N-{1-[(4-fluoro-3-{[(6-methyl(3-pyridyl))amino]carbonylamino}phenyl)methyl](4-piperidyl)}methoxycarboxamide |
| 458 (M + H) | ethoxy-N-ethyl-N-{1-[(4-fluoro-3-{[(6-methyl(3-pyridyl))amino]carbonylamino}phenyl)methyl](4-piperidyl)}carboxamide |
| 478 (M + H) | N-[5-({4-[ethyl(ethylsulfonyl)amino]-piperidyl}methyl)-2-fluorophenyl][(6-methyl(3-pyridyl))amino]carboxamide |
| 428 (M + H) | N-ethyl-N-{1-[(4-fluoro-3-{[(6-methyl(3-pyridyl))amino]carbonylamino}phenyl)methyl](4-piperidyl)}acetamide |
| 413 (M + H) | methyl 4-[(3-{[(6-cyano(3-pyridyl))amino]-carbonylamino}-4-fluorophenyl)methyl]piperazinecarboxylate |
| 427 (M + H) | ethyl 4-[(3-{[(6-cyano(3-pyridyl))amino]-carbonylamino}-4-fluorophenyl)methyl]piperazinecarboxylate |
| 441 (M + H) | methylethyl 4-[(3-{[(6-cyano(3-pyridyl))amino]-carbonylamino}-4-fluorophenyl)methyl]piperazinecarboxylate |
| 397 (M + H) | N-{5-[(4-acetylpiperazinyl)methyl]-2-fluorophenyl}[(6-cyano(3-pyridyl))amino]carboxamide |
| 452 (M + H) | methyl 4-[(3-{[(6-methyl(3-pyridyl))amino]-carbonylamino}-5-(trifluoromethyl)phenyl)methyl]piperazinecarboxylate |
| 398 (M + H) | methyl 4-[(2-methyl-5-{[(6-methyl(3-pyridyl))amino]carbonylamino}phenyl)methyl]-piperazinecarboxylate |
| 420 (M + H) | methyl 4-[(2,6-difluoro-3-{[(6-methyl(3-pyridyl))amino]carbonylamino}phenyl)methyl]-piperazinecarboxylate |
| 436 (M + H) | methyl 4-[(4-chloro-2-fluoro-5-{[(6-methyl(3-pyridyl))amino]carbonylamino}phenyl)methyl]-piperazinecarboxylate |
| 458 (M + H) | tert-butyl 4-[(1R)-1-(5-fluoro-3-{[(6-methyl(3-pyridyl))amino]carbonylamino}phenyl)ethyl]-piperazinecarboxylate |
| 416 (M + H) | methyl 4-[(1R)-1-(5-fluoro-3-{[(6-methyl(3-pyridyl))amino]carbonylamino}phenyl)ethyl]-piperazinecarboxylate |
| 430 (M + H) | ethyl 4-[(1R)-1-(5-fluoro-3-{[(6-methyl(3-pyridyl))amino]carbonylamino}phenyl)ethyl]-piperazinecarboxylate |
| 444 (M + H) | ethyl 4-[(3-{[(6-acetyl(3-pyridyl))amino]-carbonylamino}-4-fluorophenyl)methyl]piperazinecarboxylate |
| 458 (M + H) | methylethyl 4-[(3-{[(6-acetyl(3-pyridyl))amino]-carbonylamino}-4-fluorophenyl)methyl]piperazinecarboxylate |
| 414 (M + H) | [(6-acetyl(3-pyridyl))amino]-N-{5-[(4-acetylpiperazinyl)methyl]-2-fluorophenyl}carboxamide |

-continued

| Mass Spec data | Compound Name |
|---|---|
| 430 (M + H) | methyl 4-{[(4-fluoro-3-{[(6-methyl-3-pyridyl))amino]carbonylamino}phenyl)methyl]-methylamino}piperidinecarboxylate |
| 414 (M + H) | N-(5-{[(1-acetyl(4-piperidyl))methylamino]-methyl}-2-fluorophenyl)[(6-methyl-3-pyridyl))amino]carboxamide |
| 464 (M + H) | N-[5-({[1-(ethylsulfonyl)(4-piperidyl)]-methylamino}methyl)-2-fluorophenyl][(6-methyl(3-pyridyl))amino]carboxamide |
| 446 (M + H) | N-{5-[({2-[(tert-butoxy)-N-methylcarbonylamino]-ethyl}methylamino)methyl]-2-fluorophenyl}[(6-methyl(3-pyridyl))amino]carboxamide |
| 449 (M + H) | N-{5-[({2-[(tert-butoxy)-N-methylcarbonylamino]-ethyl}methylamino)methyl]-2-fluorophenyl}[(4-fluorophenyl)amino]carboxamide |
| 418 (M + H) | methyl 4-[(2-chloro-3-{[(6-methyl(3-pyridyl))amino]-carbonylamino}phenyl)methyl]piperazinecarboxylate |
| 452 (M + H) | methyl 4-[(3-{[(6-methyl(3-pyridyl))amino]-carbonylamino}-4-(trifluoromethyl)phenyl)methyl]piperazinecarboxylate |
| 458 (M + H) | tert-butyl 4-[(1S)-1-(5-fluoro-3-{[(6-methyl(3-pyridyl))amino]carbonylamino}phenyl)ethyl]-piperazinecarboxylate |
| 416 (M + H) | methyl 4-[(1S)-1-(5-fluoro-3-{[(6-methyl(3-pyridyl))amino]carbonylamino}phenyl)ethyl]-piperazinecarboxylate |
| 430 (M + H) | ethyl 4-[(1S)-1-(5-fluoro-3-{[(6-methyl(3-pyridyl))amino]carbonylamino}phenyl)ethyl]-piperazinecarboxylate |
| 430 (M + H) | methyl 4-[(3-{[(6-acetyl(3-pyridyl))amino]-carbonylamino}-4-fluorophenyl)methyl]piperazinecarboxylate |
| 348 (M + H) | N-[2-fluoro-5-(morpholin-4-ylmethyl)phenyl][(4-fluorophenyl)amino]carboxamide |
| 346 (M + H) | N-[2-fluoro-5-({methyl[2-(methylamino)ethyl]-amino}methyl)phenyl][(6-methyl(3-pyridyl))amino]carboxamide |
| 349 (M + H) | N-[2-fluoro-5-({methyl[2-(methylamino)ethyl]-amino}methyl)phenyl][(4-fluorophenyl)amino]carboxamide |
| 407 (M + H) | N-(2-{[(4-fluoro-3-{[(4-fluorophenyl)amino]carbonylamino}phenyl)methyl]-methylamino}ethyl)methoxy-N-methylcarboxamide |
| 391 (M + H) | N-(2-{[(4-fluoro-3-{[(4-fluorophenyl)amino]carbonylamino}phenyl)methyl]-methylamino}ethyl)-N-methylacetamide |
| 409 (M + H) | methyl 4-[(2-cyano-5-{[(6-methyl(3-pyridyl))amino]-carbonylamino}phenyl)methyl]piperazinecarboxylate |
| 420 (M + H) | methyl 4-[(3,4-difluoro-5-{[(6-methyl(3-pyridyl))amino]-carbonylamino}phenyl)methyl]piperazinecarboxylate |
| 427 (M + H) | N-{2-fluoro-5-[(methyl{2-[methyl-(methylsulfonyl)amino]ethyl}amino)methyl]phenyl}[(4-fluorophenyl)amino]carboxamide |
| 441 (M + H) | N-{5-[({2-[(ethylsulfonyl)methylamino]-ethyl}methylamino)methyl]-2-fluorophenyl}[(4-fluorophenyl)amino]carboxamide |
| 348 (M + H) | N-[5-fluoro-3-(morpholin-4-ylmethyl)phenyl][(4-fluorophenyl)amino]carboxamide |
| 404 (M + H) | N-(2-{[(4-fluoro-3-{[(6-methyl(3-pyridyl))amino]-carbonylamino}phenyl)methyl]methylamino}-ethyl)methoxy-N-methylcarboxamide |
| 388 (M + H) | N-(2-{[(4-fluoro-3-{[(6-methyl(3-pyridyl))amino]-carbonylamino}phenyl)methyl]methylamino}-ethyl)-N-methylacetamide |
| 440 (M + H) | tert-butyl 4-[(1S)-1-(3-{[(6-methyl(3-pyridyl))amino]-carbonylamino}phenyl)ethyl]piperazinecarboxylate |
| 340 (M + H) | N-[3-((1S)-1-piperazinylethyl)phenyl][(6-methyl(3-pyridyl))amino]carboxamide |
| 398 (M + H) | methyl 4-[(1S)-1-(3-{[(6-methyl(3-pyridyl))amino]-carbonylamino}phenyl)ethyl]piperazinecarboxylate |
| 412 (M + H) | ethyl 4-[(1S)-1-(3-{[(6-methyl(3-pyridyl))amino]-carbonylamino}phenyl)ethyl]piperazinecarboxylate |
| 432 (M + H) | N-(3-{(1S)-1-[4-(ethylsulfonyl)piperazinyl]-ethyl}phenyl)[(6-methyl(3-pyridyl))amino]carboxamide |
| 382 (M + H) | N-{3-[(1S)-1-(4-acetylpiperazinyl)ethyl]-phenyl}[(6-methyl(3-pyridyl))amino]carboxamide |
| 424 (M + H) | N-{2-fluoro-5-[(methyl{2-[methyl-(methylsulfonyl)amino]ethyl}amino)methyl]-phenyl}[(6-methyl(3-pyridyl))amino]carboxamide |
| 438 (M + H) | N-{5-[({2-[(ethylsulfonyl)methylamino]-ethyl}methylamino)methyl]-2-fluoro-phenyl}[(6-methyl(3-pyridyl))amino]carboxamide |
| 398 (M + H) | methyl 4-[(1R)-1-(3-{[(6-methyl(3-pyridyl))amino]-carbonylamino}phenyl)ethyl]piperazinecarboxylate |
| 412 (M + H) | ethyl 4-[(1R)-1-(3-{[(6-methyl(3-pyridyl))amino]-carbonylamino}phenyl)ethyl]piperazinecarboxylate |
| 416 (M + H) | methyl 4-[(1S)-1-(2-fluoro-3-{[(6-methyl(3-pyridyl))amino]carbonylamino}phenyl)ethyl]-piperazinecarboxylate |
| 430 (M + H) | ethyl 4-[(1S)-1-(2-fluoro-3-{[(6-methyl(3-pyridyl))amino]carbonylamino}phenyl)ethyl]-piperazinecarboxylate |
| 400 (M + H) | N-{3-[(1S)-1-(4-acetylpiperazinyl)ethyl]-2-fluorophenyl}[(6-methyl(3-pyridyl))amino]carboxamide |
| 420 (M + H) | methyl 4-[(2,4-difluoro-3-{[(6-methyl(3-pyridyl))amino]carbonylamino}phenyl)methyl]-piperazinecarboxylate |
| 420 (M + H) | methyl 4-[(2,5-difluoro-3-{[(6-methyl(3-pyridyl))amino]carbonylamino}phenyl)methyl]-piperazinecarboxylate |
| 398 (M + H) | methyl 4-[2-(3-{[(6-methyl-3-pyridyl)amino]carbonylamino}phenyl)ethyl]-piperazinecarboxylate |
| 412 (M + H) | ethyl 4-[2-(3-{[(6-methyl-3-pyridyl)amino]carbonylamino}phenyl)ethyl]-piperazinecarboxylate |
| 432 (M + H) | N-(3-{2-[4-(ethylsulfonyl)piperazinyl]ethyl}-phenyl)[(6-methyl(3-pyridyl))amino]carboxamide |
| 430 (M + H) | methyl 4-[3-(2-fluoro-3-{[(6-methyl(3-pyridyl))amino]carbonylamino}phenyl)propyl]-piperazinecarboxylate |
| 472 (M + H) | tert-butyl 4-[3-(2-fluoro-3-{[(6-methyl(3-pyridyl))amino]carbonylamino}phenyl)propyl]-piperazinecarboxylate |
| 400 (M + H) | methyl 4-[(2-hydroxy-3-{[(6-methyl(3-pyridyl))amino]carbonylamino}phenyl)methyl]-piperazinecarboxylate |
| 434 (M + H) | N-(3-{[4-(ethylsulfonyl)piperazinyl]methyl}-2-hydroxyphenyl)[(6-methyl(3-pyridyl))amino]carboxamide |
| 411 (M + H) | N-(3-{2-[4-(N,N-dimethylcarbamoyl)piperazinyl]-ethyl}phenyl)[(6-methyl(3-pyridyl))amino]carboxamide |
| 447 (M + H) | N-[3-(2-{4-[(dimethylamino)sulfonyl]-piperazinyl}ethyl)phenyl][(6-methyl(3-pyridyl))amino]carboxamide |
| 418 (M + H) | [(6-methyl(3-pyridyl))amino]-N-(3-{2-[4-(methylsulfonyl)piperazinyl]ethyl}phenyl)carboxamide |
| 414 (M + H) | ethyl 4-[(2-hydroxy-3-{[(6-methyl(3-pyridyl))amino]carbonylamino}phenyl)methyl]-piperazinecarboxylate |
| 420 (M + H) | N-(2-hydroxy-3-{[4-(methylsulfonyl)piperazinyl]-methyl}phenyl)[(6-methyl(3-pyridyl))amino]carboxamide |
| 382 (M + H) | N-{3-[2-(4-acetylpiperazinyl)ethyl]-phenyl}[(6-methyl(3-pyridyl))amino]carboxamide |
| 372 (M + H) | N-[2-fluoro-3-3-piperazinylpropyl)phenyl]-[(6-methyl(3-pyridyl))amino]carboxamide |
| 464 (M + H) | N-(3-{3-[4-(ethylsulfonyl)piperazinyl]propyl}-2-fluorophenyl)[(6-methyl(3-pyridyl))amino]carboxamide |
| 414 (M + H) | N-{3-[3-(4-acetylpiperazinyl)propyl]-2-fluorophenyl}[(6-methyl(3-pyridyl))amino]carboxamide |
| 444 (M + H) | ethyl 4-[3-(2-fluoro-3-{[(6-methyl(3-pyridyl))amino]carbonylamino}phenyl)propyl]-piperazinecarboxylate |

| Mass Spec data | Compound Name |
|---|---|
| 416 (M + H) | methyl 4-[(3-{[(1-hydroxy-6-methyl-3-pyridyl)amino]carbonylamino}phenyl)methyl]-piperazinecarboxylate |
| 434 (M + H) | methyl 4-[(2-fluoro-3-{[(1-hydroxy-6-methyl(3-pyridyl))amino]carbonylamino}phenyl)methyl]-piperazinecarboxylate |
| 506 (M + H) | phenylmethyl (2S,6R)-4-[(2-fluoro-3-{[(6-methyl(3-pyridyl))amino]carbonylamino}phenyl)methyl]-2,6-dimethylpiperazinecarboxylate |
| 414 (M + H) | N-{3-[((3S,5R)-4-acetyl-3,5-dimethylpiperazinyl)methyl]-2-fluorophenyl}[(6-methyl(3-pyridyl))amino]carboxamide |
| 444 (M + H) | tert-butyl 4-[(2-fluoro-3-{[N-(6-methyl(3-pyridyl))carbamoyl]amino}phenyl)methyl]-piperazinecarboxylate |
| 416 (M + H) | ethyl 4-[(2-fluoro-3-{[N-(6-methyl(3-pyridyl))carbamoyl]amino}phenyl)methyl]-piperazinecarboxylate |
| 386 (M + H) | ({3-[(4-acetylpiperazinyl)methyl]-2-fluorophenyl}amino)-N-(6-methyl(3-pyridyl))carboxamide |
| 451 (M + H) | {[3-({4-[(dimethylamino)sulfonyl]-piperazinyl}methyl)-2-fluorophenyl]amino}-N-(6-methyl(3-pyridyl))carboxamide |
| 415 (M + H) | [(3-{[4-(N,N-dimethylcarbamoyl)piperazinyl]-methyl}-2-fluorophenyl)amino]-N-(6-methyl(3-pyridyl))carboxamide |
| 436 (M + H) | [(3-{[4-(ethylsulfonyl)piperazinyl]methyl}-2-fluorophenyl)amino]-N-(6-methyl(3-pyridyl))carboxamide |
| 422 (M + H) | [(2-fluoro-3-{[4-(methylsulfonyl)piperazinyl]-methyl}phenyl)amino]-N-(6-methyl(3-pyridyl))carboxamide |
| 430 (M + H) | methyl (2S,6R)-4-[(2-fluoro-3-{[(6-methyl(3-pyridyl))amino]carbonylamino}phenyl)methyl]-2,6-dimethylpiperazinecarboxylate |
| 372 (M + H) | N-{3-[((3S,5R)-3,5-dimethylpiperazinyl)methyl]-2-fluorophenyl}[(6-methyl(3-pyridyl))amino]carboxamide |
| 392 (M + H) | methyl 4-[(2-fluoro-3-{[(5-methylisoxazol-3-yl)amino]-carbonylamino}phenyl)methyl]piperazinecarboxylate |
| 405 (M + H) | methyl 4-[(2-fluoro-3-{[(4-fluorophenyl)-amino]carbonylamino}phenyl)methyl]-piperazinecarboxylate |
| 413 (M + H) | methyl 4-[(3-{[N-(6-cyano(3-pyridyl))carbamoyl]-amino}-2-fluorophenyl)methyl]-piperazinecarboxylate |
| 430 (M + H) | methyl 4-[(3-{[N-(6-acetyl(3-pyridyl))carbamoyl]-amino}-2-fluorophenyl)methyl]piperazinecarboxylate |
| 456 (M + H) | methyl 4-{[2-fluoro-3-({N-[6-(trifluoromethyl)(3-pyridyl)]carbamoyl}amino)phenyl]methyl}-piperazinecarboxylate |
| 388 (M + H) | methyl 4-({2-fluoro-3-[(N-(4-pyridyl)carbamoyl)amino]phenyl}methyl)-piperazinecarboxylate |
| 463 (M + H) | [(3-{[4-(azetidinylsulfonyl)piperazinyl]methyl}-2-fluorophenyl)amino]-N-(6-methyl(3-pyridyl))carboxamide |
| 472 (M + H) | tert-butyl (5S,3R)-4-[(2-fluoro-3-{[N-(6-methyl(3-pyridyl))carbamoyl]amino}phenyl)methyl]-3,5-dimethylpiperazinecarboxylate |
| 430 (M + H) | methyl (5S,3R)-4-[(2-fluoro-3-{[N-(6-methyl(3-pyridyl))carbamoyl]amino}phenyl)methyl]-3,5-dimethylpiperazinecarboxylate |
| 414 (M + H) | ({3-[((6S,2R)-4-acetyl-2,6-dimethylpiperazinyl)-methyl]-2-fluorophenyl}amino)-N-(6-methyl(3-pyridyl))carboxamide |
| 443 (M + H) | {(5S,3R)-4-[(2-fluoro-3-{[N-(6-methyl(3-pyridyl))carbamoyl]amino}phenyl)methyl]-3,5-dimethylpiperazinyl}-N,N-dimethylcarboxamide |
| 464 (M + H) | [(3-{[(6S,2R)-4-(ethylsulfonyl)-2,6-dimethylpiperazinyl]methyl}-2-fluorophenyl)amino]-N-(6-methyl(3-pyridyl))carboxamide |
| 479 (M + H) | {[3-({(6S,2R)-4-[(dimethylamino)sulfonyl]-2,6-dimethylpiperazinyl}methyl)-2-fluorophenyl]amino}-N-(6-methyl(3-pyridyl))carboxamide |
| 382 (M + H) | N-[2-fluoro-3-(1,2,4-triazolo[3,4-c]piperazin-7-ylmethyl)phenyl][(6-methyl(3-pyridyl))amino]carboxamide |
| 396 (M + H) | N-{2-fluoro-3-[(3-methyl(1,2,4-triazolo[3,4-c]piperazin-7-yl))methyl]phenyl}[(6-methyl(3-pyridyl))-amino]carboxamide |
| 410 (M + H) | N-{3-[(3-ethyl(1,2,4-triazolo[3,4-c]piperazin-7-yl))methyl]-2-fluorophenyl}[(6-methyl(3-pyridyl))amino]carboxamide |
| 408 (M + H) | N-(2-fluoro-3-{[4-(methylsulfonyl)piperazinyl]-methyl}phenyl)(4-pyridylamino)carboxamide |
| 422 (M + H) | N-(3-{[4-(ethylsulfonyl)piperazinyl]methyl}-2-fluorophenyl)(4-pyridylamino)carboxamide |
| 402 (M + H) | methyl 4-[(2-fluoro-3-{[(6-methyl(3-pyridyl))amino]carbonylamino}phenyl)methyl]-piperazinecarboxylate |

EXAMPLE 10

Target Identification Assays

Specificity assays: Specificity towards cardiac myosin is evaluated by comparing the effect of the chemical entity on actin-stimulated ATPase of a panel of myosin isoforms: cardiac, skeletal and smooth muscle, at a single 50 μM concentration or to multiple concentrations of the chemical entity.

EXAMPLE 11

In vitro Models of Dose Dependent Cardiac Myosin ATPase Modulation

Reconstituted Cardiac Sarcomere Assay: Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and ANTIFOAM (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1 \times 10^{-4}$ M to $1 \times 10^{-8}$ M.

The protein components specific to this assay are bovine cardiac myosin subfragment-1 (typically 0.5 μM), bovine cardiac actin (14 μM), bovine cardiac tropomyosin (typically 3 μM), and bovine cardiac troponin (typically 3-8 μM). The exact concentrations of tropomyosin and troponin are determined empirically, by titration to achieve maximal difference in ATPase activity when MEASURED in the presence of 2 mM EGTA versus that measured in the presence of 0.1 mM $CaCl_2$. The exact concentration of myosin in the assay is also determined empirically, by titration to achieve a desired rate of ATP hydrolysis. This varies between protein preparations, due to variations in the fraction of active molecules in each preparation.

Dose responses are typically measured at the calcium concentration corresponding to 25% or 50% of maximal ATPase activity ($pCa_{25}$ or $pCa_{50}$), so a preliminary experiment is performed to test the response of the ATPase activity to free calcium concentrations in the range of $1 \times 10^{-4}$ M to $1 \times 10^{-8}$ M. Subsequently, the assay mixture is adjusted to the $pCa_{50}$ (typically $3\times10^{-7}$ M). Assays are performed by first preparing a dilution series of test compound, each with an assay mixture containing potassium Pipes, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, $MgCl_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top-Bottom)/(1+((EC50/X)^Hill))). The AC1.4 is defined as the concentration at which ATPase activity is 1.4-fold higher than the bottom of the dose curve.

Cardiac Myofibril Assay: To evaluate the effect of chemical entities on the ATPase activity of full-length cardiac myosin in the context of native sarcomere, skinned myofibril assays are performed. Cardiac myofibrils are obtained by homogenizing cardiac tissue in the presence of a non-ionic detergent. Such treatment removes membranes and majority of soluble cytoplasmic proteins but leaves intact cardiac sarcomeric acto-myosin apparatus. Myofibril preparations retain the ability to hydrolyze ATP in a $Ca^{++}$ controlled manner. ATPase activities of such myofibril preparations in the presence and absence of chemical ENTITIES are assayed at $Ca^{++}$ concentrations across the entire calcium response range but with preferred calcium concentrations giving, 25%, 50% and 100% of a maximal rate.

Myofibrils can be prepared from either fresh or flash frozen tissue that has been rapidly thawed. Tissue is minced finely and resuspended in a relaxing buffer containing the following reagents (concentrations expressed are final solution concentrations): Tris-HCl (10 mM), $MgCl_2$ (2 mM), KCl (75 mM), EGTA (2 mM), $NaN_3$ (1 mM), ATP (1 mM), phosphocreatine (4 mM), BDM (50 mM), DTT (1 mM), benzamidine (1 mM), PMSF (0.1 mM), leupeptin (1 ug/ml), pepstatin (1 ug/ml), and triton X-100 (1%). The pH is adjusted to 7.2 at 4° C. by addition of HCl. After addition of EDTA to 10 mM, the tissue is minced by hand at 4° C., in a cold room and homogenized using a large rotor-stator homogenizer (Omni Mixer). After blending for 10s, the material is pelleted by centrifugation (5 minutes, 2000×g max, 4° C.). The myofibrils are then resuspended in a Standard Buffer containing the following reagents (concentrations expressed are final solution concentrations): Tris-HCl (10 mM) pH 7.2 at 4° C., $MgCl_2$ (2 mM), KCl (75 mM), EGTA (2 mM), $NaN_3$ (1 mM), Triton X-100 (1%), using a glass-glass tissue grinder (Kontes) until smooth, usually 4-5 strokes. The myofibril pellets are washed several times by brief homogenization, using the rotor-stator homogenizer in 10 volumes of standard buffer, followed by centrifugation. To remove detergent, the myofibrils are washed several more times with standard buffer lacking Triton X-100. The myofibrils are then subjected to three rounds of gravity filtration using 600, 300, and finally 100 µm nylon mesh (Spectrum Lab Products) to generate homogenous mixtures and pelleted down. Finally, the myofibrils are resuspended in a storage buffer containing the following reagents (concentrations expressed are final solution concentrations): Potassium PIPES (12 mM), $MgCl_2$ (2 mM), and DTT (1 mM). Solid sucrose is added while stirring to 10% (w/v) before drop-freezing in liquid nitrogen and storage at −80° C.

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (0.05 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition OF potassium hydroxide. Calcium levels are controlled by a buffering system containing 0.6 mM EGTA and varying concentrations of calcium, to achieve a free calcium concentration of $1\times10^{-4}$ M to $1\times10^{-8}$ M. The myofibril concentration in the final assay is typically 0.2 to 1 mg/ml.

Dose responses are typically measured at the calcium concentration corresponding to 25%, 50%, or 100% of maximal ATPase activity ($pCa_{25}$, $pCa_{50}$, $pCa_{100}$), so a preliminary experiment is performed to test the response of the ATPase activity to free calcium concentrations in the range of $1\times10^{-4}$ M to $1\times10^{-8}$ M. Subsequently, the assay mixture is adjusted to the $pCa_{50}$ (typically $3\times10^{-7}$ M). Assays are performed by first preparing a dilution series of test compound, each with an assay mixture containing potassium Pipes, $MgCl_2$, BSA, DTT, pyruvate kinase, lactate dehydrogenase, cardiac myofibrils, antifoam, EGTA, $CaCl_2$, and water. The assay is started by adding AN equal volume of solution containing potassium Pipes, $MgCl_2$, BSA, DTT, ATP, NADH, PEP, antifoam, and water. ATP hydrolysis is monitored by absorbance at 340 nm. The resulting dose response curve is fit by the 4 parameter equation y=Bottom+((Top-Bottom)/(1+((EC50/X)^Hill))). The AC1.4 is defined as the concentration at which ATPase activity is 1.4-fold higher than the bottom of the dose curve.

EXAMPLE 12

Myocyte Assays

PREPARATION OF ADULT CARDIAC VENTRICULAR RAT MYOCYTES. Adult male Sprague-Dawley rats are anesthetized with a mixture of isoflurane gas and oxygen. Hearts are quickly excised, rinsed and the ascending aorta cannulated. Continuous retrograde perfusion is initiated on the hearts at a perfusion pressure of 60 cm $H_2O$. Hearts are first perfused with a nominally $Ca^{2+}$ free modified Krebs solution of the following composition: 110 mM NaCl, 2.6 mM KCL, 1.2 mM $KH_2PO_4$ 7 $H_2O$, 1.2 mM $MgSO_4$., 2.1 mM $NaHCO_3$, 11 mM glucose and 4 mM Hepes (all Sigma). This medium is not recirculated and is continually gassed with $O_2$. After approximately 3 minutes the heart is perfused with modified Krebs buffer supplemented with 3.3% collagenase (169 µ/mg activity, Class II, Worthington Biochemical Corp., Freehold, N.J.) and 25 µM final calcium concentration until the heart becomes sufficiently blanched and soft. The heart is removed from the cannulae, the atria and vessels discarded and the ventricles are cut into small pieces. The myocytes are dispersed by gentle agitation of the ventricular tissue in fresh collagenase containing Krebs prior to being gently forced through a 200 µm nylon mesh in a 50 cc tube. The resulting myocytes are resuspended in modified Krebs solution containing 25 µm calcium. Myocytes are made calcium tolerant by addition of a calcium solution (100 mM stock) at 10 minute intervals until 100 µM calcium is achieved. After 30 minutes the supernatant is discarded and 30-50 ml of Tyrode buffer (137 mM NaCL, 3.7 mM KCL, 0.5 mM MgCL, 11 mM glucose, 4 mM Hepes, and 1.2 mM $CaCl_2$, pH 7.4) is added to cells. Cells are kept for 60 min at 37° C. prior to initiating experiments and used within 5 hrs of isolation. Preparations of cells are used only if cells first passed QC criteria by responding to a standard (>150% of basal) and isoproterenol (ISO; >250% of basal). Additionally, only cells whose basal contractility is between 3 and 8% are used in the following experiments.

ADULT VENTRICULAR MYOCYTE CONTRACTILITY EXPERIMENTS. Aliquots of Tyrode buffer containing myocytes are placed in perfusion chambers (series 20 RC-27NE; Warner Instruments) complete with heating platforms. Myocytes are allowed to attach, the chambers heated to 37° C., and the cells then perfused with 37° C. Tyrode buffer. Myocytes are field stimulated at 1 Hz in with platinum electrodes (20% above threshold). Only cells that have clear striations, and are quiescent prior to pacing are used for contractility experiments. To determine basal contractility, myocytes are imaged through a 40× objective and using a variable frame rate (60-240 Hz) charge-coupled device camera, the images are digitized and displayed on a computer screen at a sampling speed of 240 Hz. [Frame grabber, myopacer, acquisition, and analysis software for cell contractility are available from IonOptix (Milton, Mass.).] After a minimum 5 minute basal contractility period, test compounds (0.01-15 µM) are perfused on the myocytes for 5 minutes. After this time, fresh Tyrode buffer is perfused to determine compound washout characteristics. Using edge detection strategy, contractility of the myocytes and contraction and relaxation velocities are continuously recorded.

CONTRACTILITY ANALYSIS: Three or more individual myocytes are tested per chemical entity, using two or more different myocyte preparations. For each cell, twenty or more contractility transients at basal (defined as 1 min prior to infusion of the chemical entity) and after addition of the chemical entity, are averaged and compared. These average transients are analyzed to determine changes in diastolic length, and using the Ionwizard analysis program (IonOptix), fractional shortening (% decrease in the diastolic length), and maximum contraction and relaxation velocities (um/sec) are determined. Analysis of individual cells are combined. Increase in fractional shortening over basal indicates potentiation of myocyte contractility.

CALCIUM TRANSIENT ANALYSIS: Fura loading: Cell permeable Fura-2 (Molecular Probes) is dissolved in equal amounts of pluronic (Mol Probes) and FBS for 10 min at RT. A 1 µM Fura stock solution is made in Tyrode buffer containing 500 in M probenecid (Sigma). To load cells, this solution is added to myocytes at RT. After 10 min. the buffer is removed, the cells washed with Tyrode containing probenecid and incubated at RT for 10 min. This wash and incubation is repeated. Simultaneous contractility and calcium measurements are determined within 40 min. of loading.

Imaging: A test compound is perfused on cells. Simultaneous contractility and calcium transient ratios are determined at baseline and after addition of the compound. Cells are digitally imaged and contractility determined as described above, using that a red filter in the light path to avoid interference with fluorescent calcium measurements. Acquisition, analysis software and hardware for calcium transient analysis are obtained from IonOptix. The instrumentation for fluorescence measurement includes a xenon arc lamp and a Hyperswitch dual excitation light source that alternates between 340 and 380 wavelengths at 100 Hz by a galvo-driven mirror. A liquid filled light guide delivers the dual excitation light to the microscope and the emission fluorescence is determined using a photomultiplier tube (PMT). The fluorescence system interface routes the PMT signal and the ratios are recorded using the IonWizard acquisition program.

Analysis: For each cell, ten or more contractility and calcium ratio transients at basal and after compound addition, where averaged and compared. Contractility average transients are analyzed using the Ionwizard analysis program to determine changes in diastolic length, and fractional shortening (% decrease in the diastolic length). The averaged calcium ratio transients are analyzed using the Ionwizard analysis program to determine changes in diastolic and systolic ratios and the 75% time to baseline ($T_{75}$).

DURABILITY: To determine the durability of response, myocytes are challenged with a test compound for 25 minutes followed by a 2 min. washout period. Contractility response is compared at 5 and 25 min. following compound infusion.

THRESHOLD POTENTIAL: Myocytes are field stimulated at a voltage approximately 20% above threshold. In these experiments the threshold voltage (minimum voltage to pace cell) is empirically determined, the cell paced at that threshold and then the test compound is infused. After the activity is at steady state, the voltage is decreased for 20 seconds and then restarted. Alteration of ion channels corresponds to increasing or lowering the threshold action potential.

Hz FREQUENCY: Contractility of myocytes is determined at 3 Hz as follows: a 1 min. basal time point followed by perfusion of the test compound for 5 min. followed by a 2 min. washout. After the cell contractility has returned completely to baseline the Hz frequency is decreased to 1. After an initial acclimation period the cell is challenged by the same compound. As this species, rat, exhibits a negative force frequency at 1 Hz, at 3 Hz the FS of the cell should be lower, but the cell should still respond by increasing its fractional shortening in the presence of the compound.

ADDITIVE WITH ISOPROTERENOL: To demonstrate that a compound act via a different mechanism than the adrenergic stimulant isoproterenol, cells are loaded with fura-2 and simultaneous measurement of contractility and calcium ratios are determined. The myocytes are sequentially challenged with 5 µm or less of a test compound, buffer, 2 nM isoproterenol, buffer, and a combination of a test compound and isoproterenol.

EXAMPLE 13

In vitro Model of Dose Dependent Cardiac Myosin ATPase Modulation

Bovine and rat cardiac myosins are purified from the respective cardiac tissues. Skeletal and smooth muscle myosins used in the specificity studies are purified from rabbit skeletal muscle and chicken gizzards, respectively. All myosins used in the assays are converted to a single-headed soluble form (S1) by a limited proteolysis with chymotrypsin. Other sarcomeric components: troponin complex, tropomyosin and actin are purified from bovine hearts (cardiac sarcomere) or chicken pectoral muscle (skeletal sarcomere).

Activity of myosins is monitored by measuring the rates of hydrolysis of ATP. Myosin ATPase is very significantly activated by actin filaments. ATP turnover is detected in a coupled enzymatic assay using pyruvate kinase (PK) and lactate dehydrogenase (LDH). In this assay each ADP produced as a result of ATP hydrolysis is recycled to ATP by PK with a simultaneous oxidation of NADH molecule by LDH. NADH oxidation can be conveniently monitored by decrease in absorbance at 340 nm wavelength.

Dose responses are measured using a calcium-buffered, pyruvate kinase and lactate dehydrogenase-coupled ATPase assay containing the following reagents (concentrations expressed are final assay concentrations): Potassium PIPES (12 mM), $MgCl_2$ (2 mM), ATP (1 mM), DTT (1 mM), BSA (0.1 mg/ml), NADH (0.5 mM), PEP (1.5 mM), pyruvate kinase (4 U/ml), lactate dehydrogenase (8 U/ml), and antifoam (90 ppm). The pH is adjusted to 6.80 at 22° C. by addition of potassium hydroxide. Calcium levels are controlled by a buffering system containing 0.6 mM EGTA and varying concentrations of calcium, to achieve a free calcium concentration of $1\times10^{-4}$ M to $1\times10^{-8}$ M.

The protein components specific to this assay are bovine cardiac myosin subfragment-1 (typically 0.5 µM), bovine cardiac actin (14 bovine cardiac tropomyosin (typically 3 µM), and bovine cardiac troponin (typically 3-8 µM). The exact concentrations of tropomyosin and troponin are determined empirically, by titration to achieve maximal difference in ATPase activity when measured in the presence of 1 mM EGTA versus that measured in the presence of 0.2 mM $CaCl_2$. The exact concentration of myosin in the assay is also determined empirically, by titration to achieve a desired rate of ATP hydrolysis. This varies between protein preparations, due to variations in the fraction of active molecules in each preparation.

Compound dose responses are typically measured at the calcium concentration corresponding to 50% of maximal ATPase activity ($pCa_{50}$), so a preliminary experiment is performed to test the response of the ATPase activity to free calcium concentrations in the range of $1\times10^{-4}$ M to $1\times10^{-8}$ M. Subsequently, the assay mixture is adjusted to the $pCa_{50}$ (typically $3\times10^{-7}$M). Assays are performed by first preparing a dilution series of test compound, each with an assay mixture containing potassium Pipes, $MgCl_2$, BSA, DTT, pyruvate kinase, lactate dehydrogenase, myosin subfragment-1, antifoam, EGTA, $CaCl_2$, and water. The assay is started by adding an equal volume of solution containing potassium Pipes, $MgCl_2$, BSA, DTT, ATP, NADH, PEP, actin, tropomyosin, troponin, antifoam, and water. ATP hydrolysis is monitored by absorbance at 340 nm. The resulting dose response curve is fit by the 4 parameter equation y=Bottom+((Top-Bottom)/(1+((EC50/X)^Hill))). The AC1.4 is defined as the concentration at which ATPase activity is 1.4-fold higher than the bottom of the dose curve.

Ability of a compound to activate cardiac myosin is evaluated by the effect of the compound on the actin stimulated ATPase of S1 subfragment. Actin filaments in the assay are decorated with troponin and tropomyosin and Ca++ concentration is adjusted to a value that would result in 50% of maximal activation. S1 ATPase is measured in the presence of a dilution series of the compound. Compound concentration required for 40% activation above the ATPase rate measured in the presence of control (equivalent volume of DMSO) is reported as AC40.

EXAMPLE 14

In vivo Fractional Shortening Assay

ANIMALS Male Sprague Dawley rats from Charles River Laboratories (275-350 g) are used for bolus efficacy and infusion studies. Heart failure animals are described below. They are housed two per cage and have access to food and water ad libitum. There is a minimum three-day acclimation period prior to experiments.

ECHOCARDIOGRAPHY Animals are anesthetized with isoflurane and maintained within a surgical plane throughout the procedure. Core body temperature is maintained at 37° C. by using a heating pad. Once anesthetized, animals are shaven and hair remover is applied to remove all traces of fur from the chest area. The chest area is further prepped with 70% ETOH and ultrasound gel is applied. Using a GE System Vingmed ultrasound system (General Electric Medical Systems), a 10 MHz probe is placed on the chest wall and images are acquired in the short axis view at the level of the papillary muscles. 2-D M-mode images of the left ventricle are taken prior to, and after, compound bolus injection or infusion. In vivo fractional shortening ((end diastolic diameter−end systolic diameter)/end diastolic diameter×100) is determined by analysis of the M-mode images using the GE EchoPak software program.

BOLUS AND INFUSION EFFICACY For bolus and infusion protocols, fractional shortening is determined using echocardiography as described above. For bolus and infusion protocols, five pre-dose M-Mode images are taken at 30 second intervals prior to bolus injection or infusion of compounds. After injection, M-mode images are taken at 1 min and at five minute intervals thereafter up to 30 min. Bolus injection (0.5-5 mg/kg) or infusion is via a tail vein catheter. Infusion parameters are determined from pharmacokinetic profiles of the compounds. For infusion, animals received a 1 minute loading dose immediately followed by a 29 minute infusion dose via a tail vein catheter. The loading dose is calculated by determining the target concentration×the steady state volume of distribution. The maintenance dose concentration is determined by taking the target concentration×the clearance. Compounds are formulated in 25% cavitron vehicle for bolus and infusion protocols. Blood samples are taken to determine the plasma concentration of the compounds.

EXAMPLE 15

Hemodynamics in Normal and Heart Failure Animals

Animals are anesthetized with isoflurane, maintained within a surgical plane, and then shaven in preparation for catheterization. An incision is made in the neck region and the right carotid artery cleared and isolated. A 2 French Millar Micro-tip Pressure Catheter (Millar Instruments, Houston, Tex.) is cannulated into the right carotid artery and threaded past the aorta and into the left ventricle. End diastolic pressure readings, max+/−dp/dt, systolic pressures and heart rate are determined continuously while compound or vehicle is infused. Measurements are recorded and analyzed using a PowerLab and the Chart 4 software program (ADInstruments, Mountain View, Calif.). Hemodynamics measurements are performed at a select infusion concentration. Blood samples are taken to determine the plasma concentration of the compounds.

EXAMPLE 16

Left Coronary Artery Occlusion Model of Congestive Heart Failure

ANIMALS Male Sprague-Dawley CD (220-225 g; Charles River) rats are used in this experiment. Animals are allowed free access to water and commercial rodent diet under standard laboratory conditions. Room temperature is maintained at 20-23° C. and room illumination is on a 12/12-hour light/dark cycle. Animals are acclimatized to the laboratory environment 5 to 7 days prior to the study. The animals are fasted overnight prior to surgery.

OCCLUSION PROCEDURE Animals are anaesthetized with ketamine/xylazine (95 mg/kg and 5 mg/kg) and intubated with a 14-16-gauge modified intravenous catheter. Anesthesia level is checked by toe pinch. Core body temperature is maintained at 37° C. by using a heating blanket. The surgical area is clipped and scrubbed. The animal is placed in right lateral recumbency and initially placed on a ventilator with a peak inspiratory pressure of 10-15 cm $H_2O$ and respiratory rate 60-110 breaths/min. 100% $O_2$ is delivered to the animals by the ventilator. The surgical site is scrubbed with surgical scrub and alcohol. An incision is made over the rib cage at the 4th-5th intercostal space. The underlying muscles are dissected with care to avoid the lateral thoracic vein, to expose the intercostal muscles. The chest cavity is entered through 4th-5th intercostal space, and the incision expanded to allow visualization of the heart. The pericardium is opened to expose the heart. A 6-0 silk suture with a taper needle is passed around the left coronary artery near its origin, which lies in contact with the left margin of the pulmonary cone, at about 1 mm from the insertion of the left auricular appendage. The left coronary artery is ligated by tying the suture around the artery ("LCL"). Sham animals are treated the same, except that the suture is not tied. The incision is closed in three layers. The rat is ventilated until able to ventilate on its own. The rats are extubated and allowed to recover on a heating pad. Animals receive buprenorphine (0.01-0.05 mg/kg SQ) for post operative analgesia. Once awake, they are returned to their cage. Animals are monitored daily for signs of infection or distress. Infected or moribund animals are euthanized. Animals are weighed once a week.

EFFICACY ANALYSIS Approximately eight weeks after infarction surgery, rats are scanned for signs of myocardial infarction using echocardiography. Only those animals with decreased fractional shortening compared to sham rats are utilized further in efficacy experiments. In all experiments, there are four groups, sham+vehicle, sham+compound, LCL+vehicle and LCL+compound. At 10-12 weeks post LCL, rats are infused at a select infusion concentration. As before, five pre-dose M-Mode images are taken at 30 second intervals prior to infusion of compounds and M-mode images are taken at 30 second intervals up to 10 minutes and every minute or at five minute intervals thereafter. Fractional shortening is determined from the M-mode images. Comparisons between the pre-dose fractional shortening and compound treatment are performed by ANOVA and a post-hoc Student-Newman-Keuls. Animals are allowed to recover and within 7-10 days, animals are again infused with compounds using the hemodynamic protocol to determine hemodynamic changes of the compounds in heart failure animals. At the end to the infusion, rats are killed and the heart weights determined.

When tested as described in Examples 10-16, chemical entities described herein are shown to have the desired activity.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the invention. All patents and publications cited above are hereby incorporated by reference.

EXAMPLE 17

Cardiac Contractility In Vitro and In Vivo in a Rat Model of Heart Failure

A myofibril assay is used to identify compounds (myosin activators) that directly activate the cardiac myosin ATPase. The cellular mechanism of action, in vivo cardiac function in Sprague Dawley (SD) rats, and efficacy in SD rats with defined heart failure to active compound is then determined. Cellular contractility was quantified using an edge detection strategy and calcium transient measured using fura-2 loaded adult rat cardiac myocytes. Cellular contractility increased over baseline within 5 minutes of exposure to an active compound (0.2 □M) without altering the calcium transient. Combination of active compound with isoproterenol (□-adrenergic agonist) should result only in an additive increase in contractility with no further change in the calcium transient demonstrating the active compound was not inhibiting the PDE pathway. In vivo contractile function in anesthetized SD rats is quantified using echocardiography (M-mode) and simultaneous pressure measurements. SD rats are infused with vehicle or active compound at 0.25-2.5 mg/kg/hr. The active compound should increase fractional shortening (FS) and ejection fraction (EF) in a dose-dependent manner with no significant change in peripheral blood pressures or heart rate except at the highest dose. Rats with defined heart failure induced by left coronary ligation, or sham treated rats may have similar and significant increases in FS and EF when treated with 0.7-1.2 mg/kg/hr active compound. In summary, the active compound increased cardiac contractility without increasing the calcium transient and was efficacious in a rat model of heart failure, indicating the active compound may be a useful therapeutic in the treatment of human heart failure.

EXAMPLE 18

Pharmacology

The pharmacology of at least one chemical entity described herein is investigated in isolated adult rat cardiac myocytes, anesthetized rats, and in a chronically instrumented canine model of heart failure induced by myocardial infarction combined with rapid ventricular pacing. The active compound increases cardiac myocyte contractility (EC20=0.2 M) but does not increase the magnitude or change the kinetics of the calcium transient at concentrations up to 10 M in Fura-2 loaded myocytes. The active compound (30 M) does not inhibit phosphodiesterase type 3.

In anesthetized rats, the active compound increases echocardiographic fractional shortening from 45 5.1% to 56 4.6% after a 30 minute infusion at 1.5 mg/kg/hr (n=6, p<0.01).

In conscious dogs with heart failure, the active compound (0.5 mg/kg bolus, then 0.5 mg/kg/hr i.v. for 6-8 hours) increases fractional shortening by 74 7%, cardiac output by 45 9%, and stroke volume by 101 19%. Heart rate decreases by 27 4% and left atrial pressure falls from 22 2 mmHg to 10 2 mmHg (p<0.05 for all). In addition, neither mean arterial pressure nor coronary blood flow changes significantly. Diastolic function is not impaired at this dose. There are, no significant changes in a vehicle treated group. The active compound improved cardiac function in a manner that suggests that compounds of this class may be beneficial in patients with heart failure.

EXAMPLE 19

Pharmaceutical Composition

A pharmaceutical composition for intravenous administration is prepared in the following manner.

1 mg/mL (as free base) IV solution with the vehicle being 50 mM citric acid, pH adjusted to 5.0 with NaOH:

| Composition | Unit Formula (mg/mL) |
| --- | --- |
| Active Agent | 1.00 |
| Citric Acid | 10.51 |
| Sodium Hydroxide | qs to pH 5.0 |
| Water for Injection (WFI) | q.s. to 1 mL |

*All components other than the active compound are USP/Ph. Eur. compliant

A suitable compounding vessel is filled with WFI to approximately 5% of the bulk solution volume. The citric acid (10.51 g) is weighed, added to the compounding vessel and stirred to produce 1 M citric acid. The active agent (1.00 g) is weighed and dissolved in the 1 M citric acid solution. The resulting solution is transferred to a larger suitable compounding vessel and WFT is added to approximately 85% of the bulk solution volume. The pH of the bulk solution is measured and adjusted to 5.0 with 1 N NaOH. The solution is brought to its final volume (1 liter) with WFI.

What is claimed is:

1. A compound of the following formula and/or a pharmaceutically acceptable salt thereof

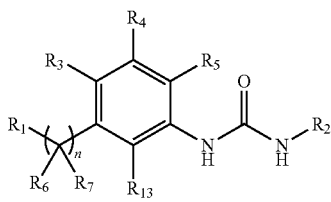

wherein n is one, two, or three;

$R_1$ is optionally substituted 2-oxo-imidazolidin-1-yl;

$R_2$ is optionally substituted aryl, optionally substituted aralkyl; optionally substituted cycloalkyl, optionally substituted heteroaryl, optionally substituted heteroaralkyl or optionally substituted heterocycloalkyl;

$R_3$ is hydrogen, halo, cyano, optionally substituted alkyl, optionally substituted heterocycloalkyl, or optionally substituted heteroaryl;

$R_4$ is hydrogen, halo, cyano, optionally substituted alkyl, optionally substituted heterocycloalkyl, or optionally substituted heteroaryl;

$R_5$ is hydrogen, halo, cyano, optionally substituted alkyl, optionally substituted heterocycloalkyl, or optionally substituted heteroaryl;

each $R_6$ and $R_7$ is independently selected from hydrogen, aminocarbonyl, alkoxycarbonyl, optionally substituted alkyl, and optionally substituted alkoxy, or $R_6$ and $R_7$, taken together with the carbon to which they are attached, form an optionally substituted 3- to 7-membered ring which optionally incorporates one or two additional heteroatoms, selected from N, O, and S in the ring; and $R_{13}$ is hydrogen, halo, cyano, hydroxyl, optionally substituted alkyl, optionally substituted heterocycloalkyl, or optionally substituted heteroaryl.

2. A compound of claim 1 and/or a pharmaceutically acceptable salt thereof, wherein $R_2$ is optionally substituted phenyl, optionally substituted naphthyl, optionally substituted pyrrolyl, optionally substituted thiazolyl, optionally substituted isooxazolyl, optionally substituted pyrazolyl, optionally substituted oxazolyl, optionally substituted 1,3,4-oxadiazolyl, optionally substituted pyridinyl, optionally substituted pyrazinyl, optionally substituted pyrimidinyl, or optionally substituted pyridazinyl.

3. A compound of claim 1 and/or a pharmaceutically acceptable salt thereof, wherein $R_2$ is pyridin-3-yl, pyridin-4-yl, pyridin-1-oxide, phenyl, pyrimidin-5-yl, or isoxazol-3-yl, wherein each of the pyridin-3-yl, pyridin-4-yl, pyridin-1-oxide, phenyl, pyrimidin-5-yl, and isoxazol-3-yl is optionally substituted with lower alkyl, lower alkoxy, halo, cyano or acetyl.

4. A compound of claim 3 and/or a pharmaceutically acceptable salt thereof, wherein $R_2$ is pyridin-3-yl which is optionally substituted with lower alkyl; $R_2$ is pyridin-4-yl which is optionally substituted with lower alkyl; phenyl which is optionally substituted with halo; optionally substituted pyrimidin-5-yl; or optionally substituted isoxazol-3-yl.

5. A compound of claim 1 and/or a pharmaceutically acceptable salt thereof, wherein the compound is chosen from compounds of the following formula

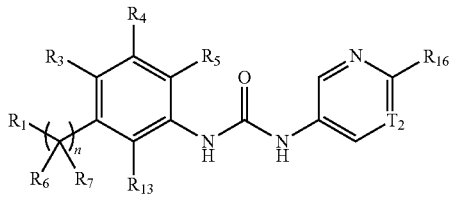

wherein $T_2$ is —C= or —N=; and $R_{16}$ is selected from hydrogen, halo, cyano, optionally substituted alkyl, and optionally substituted alkoxy.

6. A compound of claim 5 and/or a pharmaceutically acceptable salt thereof, wherein $T_2$ is —C=.

7. A compound of claim 5 and/or a pharmaceutically acceptable salt thereof, wherein $T_2$ is —N=.

8. A compound of claim 5 and/or a pharmaceutically acceptable salt thereof, wherein $R_{16}$ is selected from hydrogen, methyl, fluoro, cyano, methoxy, and acetyl.

9. A compound of claim 8, and/or a pharmaceutically acceptable salt thereof, wherein $R_{16}$ is hydrogen or methyl.

10. A compound of claim 1 and/or a pharmaceutically acceptable salt thereof, wherein $R_3$ is hydrogen, cyano, fluoro, chloro, or methyl.

11. A compound of claim 10 and/or a pharmaceutically acceptable salt thereof, wherein $R_3$ is hydrogen or fluoro.

12. A compound of claim 1 and/or a pharmaceutically acceptable salt thereof, wherein each $R_4$ and $R_5$ is independently selected from hydrogen, pyridinyl, halo and optionally substituted lower alkyl.

13. A compound of claim 12 and/or a pharmaceutically acceptable salt thereof, wherein $R_4$ is hydrogen, pyridinyl, trifluoromethyl, or fluoro.

14. A compound of claim 12 and/or a pharmaceutically acceptable salt thereof, wherein $R_5$ is hydrogen, chloro, fluoro, methyl, or trifluoromethyl.

15. A compound of claim 1 and/or a pharmaceutically acceptable salt thereof, wherein $R_{13}$ is hydrogen, halo, hydroxyl, or lower alkyl.

16. A compound of claim 15 and/or a pharmaceutically acceptable salt thereof, wherein $R_{13}$ is hydrogen or fluoro.

17. A compound of claim 1 and/or a pharmaceutically acceptable salt thereof, wherein n is one.

18. A compound of claim 1 and/or a pharmaceutically acceptable salt thereof, wherein n is two.

19. A compound of claim 1 and/or a pharmaceutically acceptable salt thereof, wherein n is three.

20. A compound of claim 1 and/or a pharmaceutically acceptable salt thereof, wherein each $R_6$ and $R_7$ is independently selected from hydrogen and methyl.

21. A compound of claim 1 and/or a pharmaceutically acceptable salt thereof, wherein $R_6$ and $R_7$ are hydrogen.

22. A compound of claim 17 and/or a pharmaceutically acceptable salt thereof, wherein $R_6$ is methyl and $R_7$ is hydrogen.

23. A compound of claim 1 and/or a pharmaceutically acceptable salt thereof, wherein $R_3$, $R_4$, $R_5$, and $R_{13}$ are hydrogen.

24. A compound of claim 1 and/or a pharmaceutically acceptable salt thereof, wherein one of $R_3$, $R_4$, $R_5$, and $R_{13}$ is halo, methyl or cyano and the others are hydrogen.

25. A compound of claim 1 and/or a pharmaceutically acceptable salt thereof, wherein two of $R_3$, $R_4$, $R_5$, and $R_{13}$ are independently halo or cyano and the others are hydrogen.

26. A compound of claim 1 and/or a pharmaceutically acceptable salt thereof, wherein $R_2$ is pyridin-3-yl which is optionally substituted with lower alkyl; phenyl which is optionally substituted with halo; optionally substituted pyrimidin-5-yl; or optionally substituted isoxazol-3-yl;

$R_3$ is hydrogen or fluoro;

$R_4$ is hydrogen, pyridinyl or fluoro;

$R_5$ is hydrogen or fluoro;

each $R_6$ and $R_7$ is independently selected from hydrogen and methyl; and $R_{13}$ is hydrogen or fluoro.

27. A compound of claim 1 and/or a pharmaceutically acceptable salt thereof, wherein $R_2$ is pyridin-3-yl which is optionally substituted with lower alkyl; phenyl which is optionally substituted with halo; optionally substituted pyrimidin-5-yl; or optionally substituted isoxazol-3-yl;

$R_3$ is hydrogen or fluoro;

$R_4$ is hydrogen, pyridinyl or fluoro;

$R_5$ is hydrogen or fluoro;

each $R_6$ and $R_7$ is independently selected from hydrogen and methyl; and $R_{13}$ is hydrogen or fluoro, wherein one of $R_3$, $R_4$, and $R_5$ is not hydrogen.

28. A compound of claim 1 and/or a pharmaceutically acceptable salt thereof, wherein the compound is selected from N-{5-fluoro-3-[(3-methyl-2-oxoimidazolidinyl)methyl]phenyl}(3-pyridylamino)carboxamide; and N-{5-fluoro-3-[(3-methyl-2-oxoimidazolidinyl)methyl]phenyl}[(6-methyl(3-pyridyl))amino]carboxamide.

29. A pharmaceutical composition comprising a pharmaceutically acceptable excipient, carrier or adjuvant and a compound of claim 1 and/or a pharmaceutically acceptable salt thereof.

30. A pharmaceutical composition of claim 29, wherein the composition is formulated in a form chosen from injectable fluids, aerosols, tablets, pills, capsules, syrups, creams, gels, and transdermal patches.

31. A packaged pharmaceutical composition, comprising a pharmaceutical composition of claim 29 and instructions for using the composition to treat a patient suffering from a heart disease.

32. The packaged pharmaceutical composition of claim 31 wherein the heart disease is heart failure.

* * * * *